(12) United States Patent
Fu

(10) Patent No.: US 9,234,232 B2
(45) Date of Patent: Jan. 12, 2016

(54) MULTIPLEX AMPLIFICATION AND DETECTION

(75) Inventor: Guoliang Fu, Abingdon (GB)

(73) Assignee: OXITEC LIMITED, Abingdon, Oxfordshire (GB)

(*) Notice: Subject to any disclaimer, the term of this patent is extended or adjusted under 35 U.S.C. 154(b) by 1293 days.

(21) Appl. No.: 13/056,422

(22) PCT Filed: Jul. 30, 2009

(86) PCT No.: PCT/GB2009/001897
§ 371 (c)(1),
(2), (4) Date: Apr. 18, 2011

(87) PCT Pub. No.: WO2010/013017
PCT Pub. Date: Feb. 4, 2010

(65) Prior Publication Data
US 2011/0207131 A1      Aug. 25, 2011

(30) Foreign Application Priority Data

Jul. 31, 2008 (GB) .................................. 0814002.2
Sep. 26, 2008 (GB) .................................. 0817706.5
Jun. 1, 2009 (GB) .................................. 0909333.7

(51) Int. Cl.
*C12Q 1/68* (2006.01)

(52) U.S. Cl.
CPC ............ *C12Q 1/6818* (2013.01); *C12Q 1/6823* (2013.01); *C12Q 1/6851* (2013.01); *C12Q 1/6853* (2013.01)

(58) Field of Classification Search
None
See application file for complete search history.

(56) References Cited

U.S. PATENT DOCUMENTS

| 6,472,156 B1 | 10/2002 | Wittwer et al. |
| 2005/0053950 A1 | 3/2005 | Zudaire Ubani et al. |
| 2008/0064033 A1* | 3/2008 | Haner et al. ............... 435/6 |

FOREIGN PATENT DOCUMENTS

WO    2008/044129    4/2008

OTHER PUBLICATIONS

Huang, S. et al., "Thermodynamically modulated partially double-stranded linear DNA probe design for homogeneous real-time PCR," Nucl. Acids Res. (2007) 35(16):e101, 12 pages.
Li, Q. et al., "A new class of homogeneous nucleic acid probes based on specific displacement hybridization," Nucl. Acids Res. (2002) 30(2):e5, 9 pages.
Luk, K-C. et al., "Partially double-stranded linear DNA probes: novel design for sensitive detection of genetically polymorphic targets," J. Virol. Meth. (2007) 144:1-11.
International Search Report and Written Opinion for Application No. PCT/GB2009/001897 dated Sep. 28, 2009 (10 pages).

* cited by examiner

*Primary Examiner* — Samuel Woolwine
(74) *Attorney, Agent, or Firm* — Michael Best & Friedrich LLP

(57) ABSTRACT

The invention relates to the field of multiplex amplification. In particular, the invention relates to methods for assaying a sample for one or more nucleic acid targets in a single reaction based on the distinct melting temperatures or melting profiles of primers and/or probes. The invention also provides probes and kits for use in such methods.

21 Claims, 26 Drawing Sheets

Before amplification, probe has a melting profile

Or

Amplification

Probe is consumed

After amplification, the remaining probe has a different melting profile

Or

Before amplification, a mix of probe 1 and probe 2 has a melting profile

After amplification, the mix of remaining probes has a different melting profile Before amplification, a mix of probe 1 and probe 2 has a melting profile Amplification Collection of florescence cycle by cycle Target 1 is present    Target 2 is present    Both target 1 and 2 are present Combination of primers and probes Detection
(measuring Tm and/or melting profile for each target)

Combination of primers and probes

Detection
(measuring Tm and/or melting profile for each target)

A

Tm    45° C      50° C      55° C      60 ° C

B

WT template

Variant template

E

F

G

H

I

J

SEQUENCE LISTING

```
<160> NUMBER OF SEQ ID NOS: 21

<210> SEQ ID NO 1
<211> LENGTH: 31
<212> TYPE: DNA
<213> ORGANISM: Artificial
<220> FEATURE:
<223> OTHER INFORMATION: K10 dervied PCR primer

<400> SEQUENCE: 1
gttcaattgg gtttcaccgc gcttagttac a                           31

<210> SEQ ID NO 2
<211> LENGTH: 22
<212> TYPE: DNA
<213> ORGANISM: Artificial
<220> FEATURE:
<223> OTHER INFORMATION: K10 dervied PCR primer

<400> SEQUENCE: 2
gcgcggtgaa acccaattga ac                                     22

<210> SEQ ID NO 3
<211> LENGTH: 31
<212> TYPE: DNA
<213> ORGANISM: Artificial
<220> FEATURE:
<223> OTHER INFORMATION: SV40 derived PCR primer

<400> SEQUENCE: 3
```

```
atcagccata ccacatttgt agaggtttta c                              31
```

```
<210> SEQ ID NO 4
<211> LENGTH: 19
<212> TYPE: DNA
<213> ORGANISM: Artificial
<220> FEATURE:
<223> OTHER INFORMATION: SV40 derived PCR primer

<400> SEQUENCE: 4
caaatgtggt atggctgat                                            19

<210> SEQ ID NO 5
<211> LENGTH: 26
<212> TYPE: DNA
<213> ORGANISM: Artificial
<220> FEATURE:
<223> OTHER INFORMATION: K10 dervied PCR primer

<400> SEQUENCE: 5
ctctgctgac ttcaaaacga gaagag                                    26

<210> SEQ ID NO 6
<211> LENGTH: 32
<212> TYPE: DNA
<213> ORGANISM: Artificial
<220> FEATURE:
<223> OTHER INFORMATION: SV40 derived PCR primer

<400> SEQUENCE: 6
ccattataag ctgcaataaa caagttaaca ac                             32

<210> SEQ ID NO 7
<211> LENGTH: 31
<212> TYPE: DNA
<213> ORGANISM: Artificial
<220> FEATURE:
<223> OTHER INFORMATION: K10 dervied PCR primer

<400> SEQUENCE: 7
gttcaattgg gtttcaccgc gcttagttac a                              31

<210> SEQ ID NO 8
<211> LENGTH: 25
<212> TYPE: DNA
<213> ORGANISM: Artificial
<220> FEATURE:
<223> OTHER INFORMATION: SV40 derived PCR primer

<400> SEQUENCE: 8
gtaagatcca ccggatctag ataac                                     25

<210> SEQ ID NO 9
<211> LENGTH: 25
<212> TYPE: DNA
<213> ORGANISM: Artificial
<220> FEATURE:
<223> OTHER INFORMATION: SV40 dervied PCR primer

<400> SEQUENCE: 9
gggaggtgtg ggaggttttt taaag                                     25

<210> SEQ ID NO 10
<211> LENGTH: 31
<212> TYPE: DNA
<213> ORGANISM: Artificial
```

```
<220> FEATURE:
<223> OTHER INFORMATION: SV40 dervied PCR primer

<400> SEQUENCE: 10
atcagccata ccacatttgt agaggtttta c                              31

<210> SEQ ID NO 11
<211> LENGTH: 27
<212> TYPE: DNA
<213> ORGANISM: Artificial
<220> FEATURE:
<223> OTHER INFORMATION: Jak2 derived PCR primer

<400> SEQUENCE: 11
aacagatgct ctgagaaagg cattaga                                   27

<210> SEQ ID NO 12
<211> LENGTH: 15
<212> TYPE: DNA
<213> ORGANISM: Artificial
<220> FEATURE:
<223> OTHER INFORMATION: Jak2 derived PCR primer

<400> SEQUENCE: 12
ctcagagcat ctgtt                                                15

<210> SEQ ID NO 13
<211> LENGTH: 24
<212> TYPE: DNA
<213> ORGANISM: Artificial
<220> FEATURE:
<223> OTHER INFORMATION: Jak2 dervied PCR primer

<400> SEQUENCE: 13
gcatctttat tatggcagag agaa                                      24

<210> SEQ ID NO 14
<211> LENGTH: 27
<212> TYPE: DNA
<213> ORGANISM: Artificial
<220> FEATURE:
<223> OTHER INFORMATION: Jak2 dervied PCR primer

<400> SEQUENCE: 14
gtggagacga gagtaagtaa aactaca                                   27

<210> SEQ ID NO 15
<211> LENGTH: 29
<212> TYPE: DNA
<213> ORGANISM: Artificial
<220> FEATURE:
<223> OTHER INFORMATION: Jak2 derived PCR primer

<400> SEQUENCE: 15
ctcctgttaa attatagttt acactgaca                                 29

<210> SEQ ID NO 16
<211> LENGTH: 27
<212> TYPE: DNA
<213> ORGANISM: Artificial
<220> FEATURE:
<223> OTHER INFORMATION: Jak2 derived PCR primer

<400> SEQUENCE: 16
aacagatgct ctgagaaagg cattaga                                   27
```

```
<210> SEQ ID NO 17
<211> LENGTH: 34
<212> TYPE: DNA
<213> ORGANISM: Artificial
<220> FEATURE:
<223> OTHER INFORMATION: Kras derived PCR primer

<400> SEQUENCE: 17
gtcacatttt cattattttt attataaggc ctgc                                34

<210> SEQ ID NO 18
<211> LENGTH: 26
<212> TYPE: DNA
<213> ORGANISM: Artificial
<220> FEATURE:
<223> OTHER INFORMATION: Kras derived PCR primer

<400> SEQUENCE: 18
gatcatattc gtccacaaaa tgattc                                         26

<210> SEQ ID NO 19
<211> LENGTH: 29
<212> TYPE: DNA
<213> ORGANISM: Artificial
<220> FEATURE:
<223> OTHER INFORMATION: Kras derived PCR primer

<400> SEQUENCE: 19
gaatataaac ttgtggtagt tggagctgt                                      29

<210> SEQ ID NO 20
<211> LENGTH: 15
<212> TYPE: DNA
<213> ORGANISM: Artificial
<220> FEATURE:
<223> OTHER INFORMATION: Kras derived PCR primer

<400> SEQUENCE: 20
cacaagttta tattc                                                     15

<210> SEQ ID NO 21
<211> LENGTH: 26
<212> TYPE: DNA
<213> ORGANISM: Artificial
<220> FEATURE:
<223> OTHER INFORMATION: K10 derived PCR primer

<400> SEQUENCE: 21
cctgagggtt aaatcttccc cattga                                         26
```

MULTIPLEX AMPLIFICATION AND DETECTION

CROSS-REFERENCE TO RELATED APPLICATIONS

This patent application is a national stage filing under 35 U.S.C. 371 of International Application No. PCT/GB2009/001897, filed on Jul. 30, 2009, which claims foreign priority benefits to United Kingdom Patent Application No. 0814002.2, filed Jul. 31, 2008, United Kingdom Patent Application No. 0817706.5, filed Sep. 26, 2008 and United Kingdom Patent Application No. 0909333.7, filed Jun. 1, 2009, which are incorporated herein by reference in their entireties.

The present invention relates to the field of multiplex detection. In particular, the invention relates to methods for assaying a sample for one or more nucleic acid targets in a single reaction based on the distinct melting temperatures or melting profiles of probes. The invention also provides probes and kits for use in such methods.

Multiplex PCR, which uses multiple pairs of primers to simultaneously amplify multiple target sequences in a single PCR reaction, is a more efficient approach to PCR than standard single primer-pair PCR. The simultaneous amplification of various targets reduces both the cost and turn-around time of PCR analysis, minimizes experimental variations and the risk of cross-contamination, and increases the reliability of end results. Multiplex PCR has been used in many areas of DNA testing including identification of micro-organisms, gene expression analysis, mutation and polymorphism analysis, genotyping and DNA array analysis, and RNA detection.

Real-time PCR has been developed to quantify amplified products during PCR reactions. Real-time PCR is based on the principles that emission of fluorescence from dyes directly or indirectly associated with the formation of newly-synthesized amplicons or the annealing of primers with DNA templates can be detected and is proportional to the amount of amplicons in each PCR cycle. Real-time PCR is carried out in a closed-tube format and it is quantitative. Several methods are currently available for performing real-time PCR, such as utilising TaqMan probes (U.S. Pat. Nos. 5,210,015 and 5,487,972, and Lee et al., Nucleic Acids Res. 21:3761-6, 1993), molecular beacons (U.S. Pat. Nos. 5,925,517 and 6,103,476, and Tyagi and Kramer, Nat. Biotechnol. 14:303-8, 1996), self-probing amplicons (scorpions) (U.S. Pat. No. 6,326,145, and Whitcombe et al., Nat. Biotechnol. 17:804-7, 1999), Amplisensor (Chen et al., Appl. Environ. Microbiol. 64:4210-6, 1998), Amplifluor (U.S. Pat. No. 6,117,635, and Nazarenko et al., Nucleic Acids Res. 25:2516-21, 1997, displacement hybridization probes (Li et al., Nucleic Acids Res. 30:E5, 2002); DzyNA-PCR (Todd et al., Clin. Chem. 46:625-30, 2000), fluorescent restriction enzyme detection (Cairns et al. Biochem. Biophys. Res. Commun. 318:684-90, 2004) and adjacent hybridization probes (U.S. Pat. No. 6,174,670 and Wittwer et al., Biotechniques 22:130-1, 134-8, 1997). Most of these probes consist of a pair of dyes (a reporter dye and an acceptor dye) that are involved in fluorescence resonance energy transfer (FRET), whereby the acceptor dye quenches the emission of the reporter dye. In general, the fluorescence-labelled probes increase the specificity of amplicon quantification.

Another form of probe used in PCR is a double-stranded linear probe which has two complementary oligonucleotides. The probes described in the prior art have been of equal length, in which at least one of the oligonucleotides acts as a probe for a target sequence in a single-stranded conformation. The 5' end of one of the oligonucleotides is labelled with a fluorophore and the 3' end of the other oligonucleotide is labelled with a quencher, e.g., an acceptor fluorophore, or vice versa. When these two oligonucleotides are annealed to each other, the two labels are close to one another, thereby quenching fluorescence. Target nucleic acids, however, compete for binding to the probe, resulting in a less than proportional increase of probe fluorescence with increasing target nucleic acid concentration (Morrison L. et al., Anal. Biochem., Vol. 183, pages 231-244 (1989); U.S. Pat. No. 5,928,862).

Double-stranded linear probes modified by shortening one of the two complementary oligonucleotides by a few bases to make a partially double-stranded linear probe, are also known in the art. In such double-stranded linear probes in the prior art, the longer oligonucleotide has been end-labelled with a fluorophore and the slightly shorter oligonucleotide has been end-labelled with a quencher. In the double-stranded form, the probe is less fluorescent due to the close proximity of the fluorophore and the quencher. In the presence of a target, however, the shorter quencher oligonucleotide is displaced by the target. As a result, the longer oligonucleotide (in the form of probe-target hybrid) becomes substantially more fluorescent (Li et al., Nucleic Acids Research, Vol. 30, No. 2, e5 (2002)).

US 2005/0227257 describes a slightly modified double stranded linear nucleic acid probe. The probe described in this patent application is modified by shortening one of the two complementary oligonucleotides by more bases, compared to the above, to make a partially double-stranded linear probe.

Fluorescent hybridisation probes have also been used in other fields. For example, methods for multiplex genotyping using fluorescent hybridisation probes have been described (e.g. U.S. Pat. No. 6,140,054) which use the melting temperature of fluorescent hybridization probes that hybridize to a PCR amplified targeted region of genome/nucleic acid sequence to identify mutations and polymorphisms.

The advent of high-throughput genetic testing has necessitated both qualitative and quantitative analysis of multiple genes and has led to the convergence of multiplex PCR and real-time PCR into multiplex real-time PCR. Since double-stranded DNA intercalating dyes are not suitable for multiplexing due to their non-specificity, fluorescence-labelled probes have made multiplex real-time PCR possible. However, multiplex real-time PCR is limited by the availability of fluorescence dye combinations. Currently, only up to four or five fluorescence dyes can be detected and quantified simultaneously in real-time PCR.

US2005/0053950 describes a protocol for quantifying multiplex real-time polymerase chain reactions (PCR). The methods quantify multiple PCR products or amplicons in a single real-time PCR reaction based on the different melting temperatures ($T_m$) of each amplicon and the emission changes of double-stranded DNA dyes such as SYBR Green I when amplicons are in duplex or in separation. For a specific amplicon with a $T_m$, the emission difference between the emission reading taken at a temperature below the $T_m$ and the emission reading taken at a temperature above the $T_m$ corresponds to the emission value of the amplicon in duplex. Accordingly, the emission difference of each amplicon in a single PCR reaction can be used to quantify each amplicon. However, the multiplexity and sensitivity of such methods can be relatively low. For example, the difference in melting temperatures between amplicons of the order of 100-150 nucleotides in length is small. Therefore, these techniques require the use of amplicons with large differences in their sizes in order to be able to distinguish between them.

There is a need, however, to develop other methods of amplifying and quantifying multiple target sequences in a single PCR reaction for multiplex real-time PCR with greater levels of multiplexity and sensitivity.

The method of the present invention differs from prior art technologies. Firstly, the method is based on the different melting properties ($T_m$ or melting profile) of each probe and the emission changes of labels on the probe when the probe's internal double-stranded portions are in duplex or in separation. The probe of present invention comprises a double-stranded portion which can be formed by a first oligonucleotide and a second oligonucleotide; the double stranded portion has a distinct $T_m$ for each probe which distinguishes different probes within a set of probes comprising the same or similar labels. Secondly, the first oligonucleotide may or may not comprise one or more labels and it is the first oligonucleotide which is consumed during the amplification reaction. The emission difference between the emission readings at two different temperatures corresponds to the emission value of the probe after some probe being consumed. Thirdly, measuring melting profiles of unconsumed probes provide an indication of the presence or amount of target nucleic acids presented in a sample.

To facilitate understanding of the invention, a number of terms are defined below.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence; i.e., a linear order of nucleotides. A "polynucleotide", as used herein, is a nucleic acid containing a sequence that is greater than about 200 nucleotides in length. An "oligonucleotide", as used herein, is a short polynucleotide or a portion of a polynucleotide. An oligonucleotide typically contains a sequence of about two to about one hundred bases. "Nucleic acid", "DNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

As used herein, the terms "target sequence", "target nucleic acid", "target nucleic acid sequence" and "nucleic acids of interest" are used interchangeably and refer to a desired region which is to be either amplified, detected or both. The target sequence, which is the object of amplification and detection, can be any nucleic acid. The target sequence can be RNA, cDNA, genomic DNA, or DNA or RNA, for example from a disease-causing micro-organism or virus. The target sequence can also be DNA treated by chemical reagents, various enzymes and physical exposure. A target nucleic acid sequence of interest in a sample may appear as single-stranded DNA or RNA such as cDNA, mRNA, other RNA or as separated complementary strands. Separating complementary strands of target nucleic acid may be accomplished by physical, chemical or enzymatic means. For the ease of description and understanding, references to nucleic acids of interest or targets refer both to these moieties as found in a test sample and to amplified copies of portions of theses nucleic acids, unless specifically noted to the contrary.

"Primer" as used herein refers to an oligonucleotide, whether occurring naturally or produced synthetically, which is capable of acting as a point of initiation of synthesis when placed under conditions in which synthesis of a primer extension product which is complementary to a nucleic acid strand is induced i.e., in the presence of nucleotides and an agent for polymerization such as DNA polymerase and at a suitable temperature and buffer. The primers herein are selected to be substantially complementary to the different strands of each specific sequence to be amplified. This means that the primers must be sufficiently complementary to hybridize with their respective strands. A non-complementary nucleotide fragment may be attached to the 5'-end of the primer, with the remainder of the primer sequence being complementary to the diagnostic section of the target base sequence. Commonly, the primers are complementary except when non-complementary nucleotides may be present at a predetermined primer terminus as described.

The term "complementary to" is used herein in relation to a nucleotide that will base pair with another specific nucleotide. Thus adenosine is complementary to uridine or thymidine and guanosine is complementary to cytidine. It is appreciated that whilst thymidine and guanosine may base pair under certain circumstances they are not regarded as complementary for the purposes of this specification. For purposes of the present invention, the term "substantially complementary" means that equal or more than 70%, preferably more than 80%, more preferably more than 90% and most preferably more than 95% or 99% of nucleobases on one strand of the probe finds its Watson-Crick binding partner on the other strand of the probe (or in the nucleic acid of interest) in an alignment such that the corresponding nucleotides can hybridize to each other. Methods to determine identity and similarity are codified in publicly available computer programs. Preferred computer program methods to determine identity and similarity between two sequences include, but are not limited to: the GCG Pileup program found in the GCG program package, using the Needleman and Wunsch algorithm with their standard default values of gap creation penalty=12 and gap extension penalty=4 (Devereux et al., Nucleic Acids Res. 12: 387-395 (1984)), BLASTP, BLASTN, and FASTA (Pearson et al., Proc. Natl. Acad. Sci. USA 85: 2444-2448 (1988)). The BLASTX program is publicly available from NCBI and other sources (BLAST Manual, Altschul et al., Natl. Cent. Biotechnol. Inf., Natl. Library Med. (NCBI NLM) NIH, Bethesda, Md.; Altschul et al., J. Mol. Biol. 215: 403-410 (1990); Altschul et al., Nucleic Acids Res. 25: 3389-3402 (1997)).

The terms "duplex" and "double-stranded" are interchangeable, mean one strand of oligo-poly-nucleotides hybridises to the complementary oligo-poly-nucleotides.

The term "identical" means that two nucleic acid sequences have the same sequence or a complementary sequence.

The term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration. Preferably the region of identity is greater than about 5 bp, more preferably the region of identity is greater than 10 bp.

As used herein, "continuous monitoring" and similar terms refer to monitoring multiple times during a cycle of PCR, preferably during temperature transitions, and more preferably obtaining at least one data point in each temperature transition.

As used herein, "cycle-by-cycle" monitoring means monitoring the PCR reaction once each cycle.

The term "Actual Consumed Amount" (ACA) means the amount of probe being consumed in a reaction as reflected by fluorescence measuring.

"Amplification" as used herein denotes the use of any amplification procedures to increase the concentration of a particular nucleic acid sequence within a mixture of nucleic acid sequences.

The term "sample" as used herein is used in its broadest sense. A biological sample suspected of containing nucleic acid can comprise, but is not limited to, genomic DNA, cDNA (in solution or bound to a solid support), and the like.

The term "label" as used herein refers to any atom or molecule which can be used to provide or aid to provided a detectable (preferably quantifiable) signal, and which can be attached to a nucleic acid or protein. Labels may provide signals detectable by fluorescence, radioactivity, colorimetry, gravimetry, magnetism, enzymatic activity and the like.

The term "adjacent" or "substantially adjacent" as used herein refers to the positioning of two oligonucleotides on its complementary strand of the template nucleic acid. The two template regions hybridised by oligonucleotides may be contiguous, i.e. there is no gap between the two template regions. Alternatively, the two template regions hybridised by the oligonucleotides may be separated by 1 to about 40 nucleotides, more preferably, about 1 to 10 nucleotides.

The term "thermally cycling," "thermal cycling", "thermal cycles" or "thermal cycle" refers to repeated cycles of temperature changes from a total denaturing temperature, to an annealing (or hybridising) temperature, to an extension temperature and back to the total denaturing temperature. The terms also refer to repeated cycles of a denaturing temperature and an extension temperature, where the annealing and extension temperatures are combined into one temperature. A total denaturing temperature unwinds all double stranded fragments into single strands. An annealing temperature allows a primer to hybridize or anneal to the complementary sequence of a separated strand of a nucleic acid template. The extension temperature allows the synthesis of a nascent DNA strand of the amplicon.

The term "reaction" as used herein refers to hybridisation reaction, extension reaction or amplification reaction or other biological, chemical reactions.

The terms "amplification mixture" or "PCR mixture" as used herein refer to a mixture of components necessary to detect target nucleic acid from nucleic acid templates. The mixture may comprise nucleotides (dNTPs), probes, a thermostable polymerase, primers, and a plurality of nucleic acid templates. The mixture may further comprise a Tris buffer, a monovalent salt, and $Mg^{2+}$. The concentration of each component is well known in the art and can be further optimized by an ordinary skilled artisan.

The terms "amplified product" or "amplicon" refers to a fragment of DNA amplified by a polymerase using a pair of primers in an amplification method such as PCR The term "melting profile" refers to a collection of measurements of an oligo(or poly)nucleotide and its complement which indicate the oligo(or poly)nucleotide molecule's transition from double-stranded to single-stranded nucleic acid (or vice-versa). The transition of a nucleic acid from double-stranded to single-stranded form is often described in the art as the "melting" of that nucleic acid molecule. The transition may also be described as the "denaturation" or "dissociation" of the nucleic acid. Accordingly, a melting profile of the present invention may also be referred to as a "dissociation profile", a "denaturation profile", a "melting curve", a "dissociation curve", a "hybridisation/dissociation profile" etc.

The "melting temperature" or "$T_m$" of a nucleic acid molecule generally refers to the temperature at which a polynucleotide dissociates from its complementary sequence. Generally, the $T_m$ may be defined as the temperature at which one-half of the Watson-Crick base pairs in duplex nucleic acid molecules are broken or dissociated (i.e., are "melted") while the other half of the Watson-Crick base pairs remain intact in a double stranded conformation. In preferred embodiments where duplex nucleic acid molecules are oligonucleotides and in other embodiments where the duplex nucleic acids dissociate in a two-state fashion, the $T_m$ of a nucleic acid may also be defined as the temperature at which one-half of the nucleic acid molecules in a sample are in a single-stranded conformation while the other half of the nucleic acid molecules in that sample are in a double-stranded conformation. $T_m$, therefore defines a midpoint in the transition from double-stranded to single-stranded nucleic acid molecules (or, conversely, in the transition from single-stranded to double-stranded nucleic acid molecules). It is well appreciated in the art that the transition from double-stranded to single-stranded nucleic acid molecules does not occur at a single temperature but, rather, over a range of temperatures. Nevertheless, the $T_m$ provides a convenient measurement for approximating whether nucleic acid molecules in a sample exist in a single-stranded or double-stranded conformation. As such, the melting temperature of a nucleic acid sample may be readily obtained by simply evaluating a melting profile for that sample.

The term "consumed" or "consumption" means that the amount of free labeled probes is decreased at a temperature at which the labeled probe is normally intact, in other words at particular temperatures the probe's double-stranded portion remains double-stranded. In particular, the decrease of the amount of free labeled probe may be result of no availability of at least one strand of the probe, which is either the first oligonucleotide of the probe or second oligonucleotide of the probe or both. The no availability of at least one strand of the probe means the first oligonucleotide of the probe, the second oligonucleotide of the probe or both oligonucleotides of the probe are hybridised with target nucleic acid. The hybridisation of the first oligonucleotide of the probe, the second oligonucleotide of the probe or both oligonucleotides of the probe with the target nucleic acid may be followed by extension of the oligonucleotides of the probe which act as primer, or by degradation of the oligonucleotides of the probe.

The present invention describes methods that allow the essentially simultaneous amplification and detection of a large number of different target nucleic acid sequences.

In a first aspect, the invention provides a method for assaying a sample for one or more target nucleic acids, said method comprising:

(a) contacting a sample comprising one or more target nucleic acids with a reaction mixture comprising:
  two or more probes, wherein each probe comprises
    a first oligonucleotide which comprises a first region which is substantially complementary to part of one target nucleic acid and a second region, and at least one second oligonucleotide which comprises a region which is substantially complementary to the second region of the first oligonucleotide, such that the first and second oligonucleotides are capable of forming a double-stranded portion,
  wherein each probe comprises a detectable label or detectable combination of labels which is/are capable of producing a changeable signal which is characteristic of the presence or absence of a double-stranded portion between the first and second oligonucleotides of that probe, and
  wherein at least two of the probes comprise the same detectable label or different detectable labels with undistinguishable emission spectra and wherein the melting characteristics (melting temperature $T_m$) of the double-stranded portions between the first and second oligonucleotides of each of such probes are different, and are distinguishable in a melting profile analysis;

(b) performing the reaction on the sample/reaction mixture, wherein the reaction is a primer extension reaction under extension conditions, wherein, when a target nucleic acid is present, the first oligonucleotides of the corresponding probe which are extendable primers, are hybridised with target sequence, therefore are consumed during the primer extension reaction, wherein the consumed oligonucleotides of probes are no longer available to participate in forming double stranded portion (the duplex) of the probe; and (c) measuring, at least once, the melting profile of the double-stranded portions between the first and second oligonucleotides of the unconsumed probes in the reaction mixture by detecting the signal(s) from the labels in those probes as a function of temperature, wherein the melting profile provides an indication of whether or not at least one target nucleic acid is present in said sample.

In this embodiment, the first oligonucleotides of probes act as primers. In a primer extension reaction, a mixture of probes is added into the reaction mixture containing all ingredients for extension under extension conditions. If a particular target nucleic acid is present in the reaction, the oligonucleotides of the corresponding probe are hybridised with target sequence, followed by extension and incorporation into the primer extension product, therefore are consumed. The consumed oligonucleotides are no longer available to participate in forming the double stranded portion of the probe. In the melting profile analysis, the consumed probe can be seen as a peak reduced or missing.

In another aspect, the invention provides a method for assaying a sample for one or more target nucleic acids, said method comprising:

(a) contacting a sample comprising one or more target nucleic acids with a hybridisation reaction mixture comprising:
  two or more probes, wherein each probe comprises
    a first oligonucleotide which comprises a first region which is substantially complementary to part of one target nucleic acid and a second region, and at least one second oligonucleotide which comprises a region which is substantially complementary to the second region of the first oligonucleotide, such that the first and second oligonucleotides are capable of forming a double-stranded portion,
  wherein each probe comprises a detectable label or detectable combination of labels which is/are capable of producing a changeable signal which is characteristic of the presence or absence of a double-stranded portion between the first and second oligonucleotides of that probe, and
  wherein at least two of the probes comprise the same detectable label or different detectable labels with undistinguishable emission spectra and wherein the melting characteristics of the double-stranded portions between the first and second oligonucleotides of each of such probes are different and are distinguishable in a melting profile analysis;

(b) performing the hybridisation reaction on the sample/reaction mixture under hybridisation conditions, wherein, when a target nucleic acid is present, the first oligonucleotides of probes which are substantially complementary to part of that target nucleic acid are hybridised with target sequence, therefore are consumed during the reaction, wherein the consumed oligonucleotides of probes are no longer available to participate in forming double stranded portion (the duplex) of the probe; and (c) measuring, at least once, the melting profile of the double-stranded portions between the first and second oligonucleotides of unconsumed probes in the reaction mixture by detecting the signal(s) from the labels in those probes as a function of temperature, wherein the melting profile provides an indication of whether or not at least one target nucleic acid is present in said sample.

In this embodiment, the first oligonucleotides of probes may act as hybridisation probe. In a hybridisation reaction, a mixture of probes is added into the reaction mixture containing all hybridisation ingredients under hybridisation conditions. If a particular target nucleic acid is present in the reaction, the oligonucleotides of the corresponding probe are hybridised to the target sequence, therefore are consumed. The consumed oligonucleotides are no longer available to participate in forming the double stranded portion of the probe. In the melting profile analysis, the consumed probe can be seen as a peak reduced or missing.

In another aspect, the invention provides a method for assaying a sample for one or more target nucleic acids, said method comprising:

(a) contacting a sample comprising one or more target nucleic acids with an amplification reaction mixture comprising:
  (i) one or more pairs of forward/reverse oligonucleotide primers, wherein the primer pairs are capable of amplifying one or more target nucleic acids, if present in the sample,
  (ii) two or more probes, wherein each probe comprises
    a first oligonucleotide which comprises a first region which is substantially complementary to part of one target nucleic acid and a second region, and at least one second oligonucleotide which comprises a region which is substantially complementary to the second region of the first oligonucleotide, such that the first and second oligonucleotides are capable of forming a double-stranded portion,
  wherein each probe comprises a detectable label or detectable combination of labels which is/are capable of producing a changeable signal which is characteristic of the presence or absence of a double-stranded portion between the first and second oligonucleotides of that probe, and
  wherein at least two of the probes comprise the same detectable label or different detectable labels with undistinguishable emissions spectra
  wherein the melting characteristics of the double-stranded portions between the first and second oligonucleotides of each of such probes are different, and are distinguishable in a melting profile analysis;

(b) performing an amplification reaction on the sample/amplification reaction mixture wherein, when a target nucleic acid is present, the first oligonucleotides which are substantially complementary to part of that target nucleic acid are hybridised with target sequence, therefore are consumed during the amplification reaction;

(c) measuring, at least once, the melting profile of the double-stranded portions between the first and second oligonucleotides of unconsumed probes by detecting the signal(s) from the labels in those probes as a function of temperature, wherein the melting profile provides an indication of whether or not at least one target nucleic acid has been amplified in said sample/amplification reaction mixture.

wherein a first probe of said at least two of the probes has a melting temperature $T_m1$ in terms of its double-stranded portion, wherein a second probe of said at least two of the probes has a melting temperature $T_m2$ in terms of its double-stranded portion, wherein $T_m1 > T_m2$, wherein the same labels are independently attached to the first and second probes, wherein a reduction of any melting peak at $T_m1$ and/or $T_m2$ provides indication of consumption of the first and/or second probe(s).

Preferably, the above method includes step (d):
(i) comparing at least two melting profiles obtained in (c) and/or
(ii) comparing a melting profile obtained in step (c)
  with a previously-obtained melting profile of the same probes or
  with a melting profile of the same probes obtained in parallel at the same time in control reactions, or
  with a theoretical melting profile of the same probes
wherein a change in the melting profile provides an indication of whether or not at least one target nucleic acid has been amplified in said sample/amplification reaction mixture.

The amplification reaction can be any amplification method, such as PCR, SDA, NASBA, LAMP, 3SR, ICAN, TMA, Helicase-dependent isothermal DNA amplification and the like. PCR is a preferred amplification method.

The amplification reaction mixture will comprise standard amplification reagents. Amplification reagents can conveniently be classified into four classes of components: (i) an aqueous buffer, often including without limitation a magnesium salt, (ii) amplification substrates, such as DNA or RNA, (iii) one or more oligonucleotide primers (normally two primers for each target sequence, the sequences defining the 5' ends of the two complementary strands of the double-stranded target sequence when PCR is employed), and (iv) an amplification enzyme such as a polynucleotide polymerase (for example, Taq polymerase for PCR or RNA polymerase for TMA), or a ligase. Appropriate nucleoside triphosphates will also generally be required. Additional reagents or additives can also be included at the discretion of the skilled artisan and selection of these reagents is within the skill of the ordinary artisan. Of course, when the amplification reagents are used to cause both reverse transcription and amplification, then reverse transcription reagents are also included in the amplification reagents. Selection of amplification reagents, according to the method of amplification reaction used, is within the skill of the ordinary artisan.

In the methods described herein, a sample is provided which is suspected to contain the target nucleic acid or the nucleotide variant of interest. The target nucleic acid contained in the sample may be double-stranded genomic DNA or cDNA if necessary, which is then denatured, using any suitable denaturing method including physical, chemical, or enzymatic means that are known to those of skill in the art. A preferred physical means for strand separation involves heating the nucleic acid until it is completely (>99%) denatured. Typical heat denaturation involves temperatures ranging from about 80° C. to about 105° C., for times ranging from a few seconds to minutes. As an alternative to denaturation, the target nucleic acid may exist in a single-stranded form in the sample, such as single-stranded RNA or DNA viruses.

The denatured nucleic acid strands are then incubated with oligonucleotide primers and probes under hybridisation conditions, i.e. conditions that enable the binding of the primers or probes to the single nucleic acid strands. In some embodiments of the invention the annealed primers and/or probes are extended by a polymerizing agent. Template-dependent extension of the oligonucleotide primer(s) is catalyzed by a polymerizing agent in the presence of adequate amounts of the four deoxyribonucleoside triphosphates (dATP, dGTP, dCTP, and dTTP), or analogues of these as discussed above, in a reaction medium comprised of the appropriate salts, metal cations and pH buffering system. Suitable polymerizing agents are enzymes known to catalyze primer- and template-dependent DNA synthesis. The reaction conditions for catalyzing DNA synthesis with these DNA polymerases are well known in the art. Probes are consumed during amplification.

An amplification primer can be a target-specific primer, which comprises a 3' priming portion which is complementary to a desired region of target nucleic acid. An amplification primer can also be a universal primer, which has a sequence which is identical or substantially identical to a 5' universal portion of target-specific primers. A reaction may contain multiple primers for amplification of multiple target sequences. The 5' universal portions of the multiple primers may have essentially the same sequence composition which is identical or substantially identical to the 3' priming portion of the universal amplification primer. Preferably, the primers are DNA primers, particularly those suitable for PCR amplification.

For SNP genotyping or detecting variant nucleotides, the amplification primer may be an allele-specific primer, wherein a terminal nucleotide of the primer is selected to be either complementary to the suspected variant nucleotide or to the corresponding normal nucleotide such that an extension product of the primer is synthesised when the primer anneals to the diagnostic region containing a particular nucleotide, but no such extension product is synthesised when the primer anneals to the diagnostic region containing no particular nucleotide of the target nucleic acid sequence.

Primer pairs of forward and reverse primers are included in the amplification reaction mixture such that, if a target nucleic acid is present in the sample, the primer pairs are capable of amplifying that target nucleic acid, preferably in an exponential manner.

In some embodiments, there will be 1-50, 1-25, 1-20 or 1-10 primer pairs in the reaction mixture. In other embodiments there will be 5-50, 5-25, 5-20 or 5-10 primer pairs in the reaction mixture. As mentioned above, the forward or reverse primer in a particular primer pair might be a universal primer which is common to more than one primer pair.

The amplification reaction mixture comprises two or more probes. Each probe comprises
  a first oligonucleotide which comprises a first region which is substantially complementary to part of one target nucleic acid and a second region, and
  a second oligonucleotide which comprises a region which is substantially complementary to the second region of the first oligonucleotide,
  such that the first and second oligonucleotides are capable of forming a double-stranded portion.

The first oligonucleotide must be capable of binding, under appropriate hybridisation conditions, to part of at least one of the target nucleic acids. Preferably, each first oligonucleotide is specific to part of only one of the target nucleic acids. The first oligonucleotide will have a first region whose nucleotide sequence is complementary or substantially complementary to the nucleotide sequence of part of one of the target nucleic acids. The length of this first complementary region is preferably 6-100 nucleotides, more preferably 15-30 nucleotides.

The overall length of the first oligonucleotide is preferably 15-150 nucleotides, more preferably 17 to 100 nucleotides, and most preferably 20-80 nucleotides.

In some embodiments, where the reaction involves primer extension or amplification, the part of the target nucleic acid to which the first oligonucleotide is complementary must fall within or overlap with the sequence to be amplified by the forward and reverse primers. Alternatively, the first oligonucleotide can be one of the amplification primers, for example, either the forward or reverse primer. In some embodiments, the first and/or second oligonucleotide is not a forward or reverse primer.

The second oligonucleotide comprises a region which is substantially complementary to a second region of the first oligonucleotide. The length of this second region is preferably 4-100 nucleotides, more preferably 15-30 nucleotides. The second region of the first oligonucleotide may or may not overlap with the first region of the first oligonucleotide.

The overall length of the second oligonucleotide is preferably 6-150 nucleotides, more preferably 10 to 100 nucleotides, and most preferably 12-80 nucleotides.

The first and second oligonucleotides may comprise 1-5 or 1-10 or more nucleotides that are not complementary to the target nucleic acid or to the first oligonucleotide, respectively, at the 5' or the 3' end.

The oligonucleotide probe may comprise nucleotides, nucleotide derivatives, nucleotide analogs, and/or non-nucleotide chemical moieties. Modifications of the probe that may facilitate probe binding include, but are not limited to, the incorporation of positively charged or neutral phosphodiester linkages in the probe to decrease the repulsion of the polyanionic backbones of the probe and target (see Letsinger et al., 1988, J. Amer. Chem. Soc. 110:4470); the incorporation of alkylated or halogenated bases, such as 5-bromouridine, in the probe to increase base stacking; the incorporation of ribonucleotides into the probe to force the probe:target duplex into an "A" structure, which has increased base stacking; and the substitution of 2,6-diaminopurine (amino adenosine) for some or all of the adenosines in the probe; the incorporation of nucleotide derivatives such as LNA (locked nucleic acid), PNA (peptide nucleic acid) or the like.

Generally the 3' terminus of the probe will be "blocked" to prohibit incorporation of the probe into a primer extension product. But in some preferred embodiments of the present invention, some probes are also working as primers and therefore are not blocked at the 3' terminus. "Blocking" can be achieved by using non-complementary bases or by adding a chemical moiety such as biotin or a phosphate group to the 3' hydroxyl of the last nucleotide, which may, depending upon the selected moiety, serve a dual purpose by also acting as a label for subsequent detection or capture of the nucleic acid attached to the label. Blocking can also be achieved by removing the 3'-OH or by using a nucleotide that lacks a 3'-OH such as a dideoxynucleotide.

It will be readily understood that the term "probe" refers to a plurality of that type of probes, i.e. the reaction mixture does not comprise merely a single molecule of that probe.

In some embodiments of the invention, the first region of said first oligonucleotide does not overlap or does not substantially overlap with the second region of said first oligonucleotide.

In other embodiments of the invention, the first region of the first oligonucleotide is substantially overlapping with the second region of said first oligonucleotide or the second region is embedded within the first region. In such embodiments, the $T_m$ of the duplex of said first oligonucleotide hybridised with the target sequence is preferably higher than the $T_m$ of the duplex of said first oligonucleotide hybridised with the second oligonucleotide such that if a target is present, the first oligonucleotide forms stronger hybrids with the target and consequently melts at a higher temperature than the first/second oligonucleotide duplex.

Preferably, said $T_m$ of the duplex of said first oligonucleotide hybridised with the target sequence is at least 2 degrees or at least 5 degrees higher than the $T_m$ of the duplex of said first oligonucleotide hybridised with the second oligonucleotide.

In other embodiments, the first oligonucleotide may comprise a third region which is identical or substantially identical to the sequence of a primer which is used in the amplification.

The probe of the present invention is capable of forming a double-stranded portion. Because of this double-stranded portion, the probe has a melting temperatures $T_m$ and a signature melting profile. In particular, a mixture of multiple probes of the present invention also has a signature melting profile.

The melting temperature ($T_m$) is affected by a number of factors, including but not limited to, salt concentration, DNA concentration, and the presence of denaturants, nucleic acid sequence, GC content, and length. Typically, each probe of double stranded nucleic acids has a unique $T_m$. At a temperature below a given $T_m$ at least 50% of nucleic acid duplex remains in duplex form. By contrast, at a temperature above a given $T_m$, over 50% of nucleic acid duplexes are expected to unwind into two single stranded oligonucleotide chains.

The $T_m$ of any given DNA fragment can be determined by methods well known in the art. For example, one method in the art to determine a $T_m$ of a DNA fragment is to use a thermostatic cell in an ultraviolet spectrophotometer and to measure absorbance at 268 nm as the temperature slowly rises. The absorbance versus temperature is plotted, presenting an S-shape curve with two plateaus. (See FIG. 1, for example). The absorbance reading half way between the two plateaus corresponds to the $T_m$ of the fragment. Alternatively, the first negative derivative of the absorbance versus temperature is plotted, presenting a normal distribution curve. The peak of the normal curve corresponds to the $T_m$ of the fragment.

The $T_m$ of a probe or $T_m$s of a mixture of multiple probes can also be determined by the nearest neighbour method and fine-tuned or accurately determined in the presence of a double stranded DNA dye or labels on the probe in a single reaction. For example, a reaction mixture containing a probe and appropriate buffer is heated from a hybridising temperature to the total denaturing temperature at a rate of 0.01° C. to 3° C. per second. At the same time, the mixture is illuminated with light at a wavelength absorbed by the dye (label) and the dye's (label's) emission is detected and recorded as an emission reading. The first negative derivative of the emission reading with respect to temperature is plotted against temperature to form a number of normal curves, and each peak of the curve corresponds to the actual $T_m$ of the probe. The curve is also know as "melting profile" or "hybridisation/dissociation profile". The $T_m$ or melting profile of a probe can also be estimated by a computer program based on theory well known in the art.

For a multiplex detection, sets of multiple probes for multiple target sequences are included in a reaction. In one embodiment, the different probes in a set of probes can comprise the same labels or labels with undistinguishable emission spectra. Each probe in such a set should have different $T_m$s, therefore enabling the individual melting profiles to be distinguished from one another. While the individual probe has a melting profile, the mixture of the multiple probes in the set also has melting profile which is characteristics for the set of the probes.

In accordance with the present invention, multiple loci of a target nucleic acid sequence can be analyzed in a single vessel by designing sets of probes that hybridize to different genetic loci and probes have different melting temperatures in terms of the probe's internal duplexes. If a target sequence is present, its corresponding probe is consumed. The sequence of the target loci can then be determined based on the comparison of the melting profile of the remaining probes with the melting profile of probes before the reaction. Advantageously, the different probes in a set can be attached with the same label, allowing for monitoring at a single emission wavelength. In one embodiment each probe in the set is attached with the same labels, for example a fluorescent energy transfer pair or contact quenching pair, and more particularly, a first label which is a fluorophore and a second label which is a quencher. On the other hand, the multiple sets of probes can be attached with different label pairs so that the sets of probes can be distinguished from one another based on the distinguishable emission spectra.

In accordance with one embodiment, the method of analysing multiple targets uses a mixture of probes that are attached with different labels that have distinguishable emission spectra as well as probes that are attached with labels that have overlapping emission spectra, but are distinguishable based on differences in melting temperatures of the internal double stranded portions of the probes.

The probe comprises a first oligonucleotide, wherein said first oligonucleotide comprises a first region substantially complementary to a target nucleic acid (see for example, FIG. 4). In one embodiment, the probe comprises a first oligonucleotide and at least one second oligonucleotide (see for example, FIG. 4A-J). The first oligonucleotide comprises a first region which is substantially complementary to a target nucleic acid, and second region which is substantially complementary to a second oligonucleotide(s) such that the first oligonucleotide and second oligonucleotide(s) can bind together to form a double-stranded portion. The first region and second region can arranged in any order, such as 5' to 3' or 3' to 5' (see for example FIG. 4A) or one embodied within one another (see for example FIG. 4B). It is preferred that if the first oligonucleotide serves as primer, the first region and second region are arranged in an order as 3' to 5' (see for example FIG. 4A).

In one aspect, the first region of said first oligonucleotide is not overlapping or not substantially overlapping with second region of said first oligonucleotide (see for example FIG. 4A). In other words, the first region is complementary to a target sequence, while the second region may not be complementary to the target sequence. When the second region is not complementary to the target sequence, different probes may have the identical or substantially identical second region sequence and the same second oligonucleotide may be shared between different probes in the set of probes. While the second oligonucleotides may be the same among the set of probes, the second regions of first oligonucleotides of different probes in the set may have the length and/or nucleotide sequence difference such that the $T_m$ and the melting profile of the probes are different.

In another aspect, the first region of said first oligonucleotide is substantially overlapping with the second region of said first oligonucleotide or the second region is embedded in the first region (see for example, FIG. 4B), wherein $T_m$ of the duplex of said first oligonucleotide hybridised with the target sequence is higher than the $T_m$ of the duplex of said first oligonucleotide hybridised with the second oligonucleotide such that if a target is present, the target forms stronger hybrids with the first oligonucleotide of the probe and consequently the duplex of the target/first oligonucleotide melts at a higher temperature than the duplex of second oligonucleotide/first oligonucleotide. In this aspect, the first region may be longer than the second region or the second region may comprise mismatch nucleotides when hybridised with the second oligonucleotide. Binding of the first oligonucleotide to the target nucleic acid prevents the second oligonucleotide from binding to the first oligonucleotide of the probe. It is preferred that the $T_m$ of the hybrid of said first oligonucleotide and the target sequence is at least 2 degrees higher than the $T_m$ of the hybrid of said first oligonucleotide and the second oligonucleotide. It is more preferred that $T_m$ of the hybrid of said first oligonucleotide and the target sequence is at least 5 degrees higher than the $T_m$ of the hybrid of said first oligonucleotide and the second oligonucleotide.

In yet another aspect, the first oligonucleotide comprises a third region which is identical or substantially identical to a primer sequence (see for example, FIGS. 4C and E). The third region may be complementary or not complementary to the target sequence. Multiple probes in a set of probes may comprise the same third region sequence. The primer identical to the third region sequence may act as a universal amplification primer. When the target specific probe (acting as primer) is running low at several cycles of amplification, the universal primer can take over and proceed to following cycles of amplification.

In some embodiments of the invention, the first and second oligonucleotides are linked by a linker moiety. This linker moiety may comprise nucleotides, nucleotide derivatives, nucleotide analogs or a non-nucleotide chemical linkage, i.e. the first and second oligonucleotides might be a single stretch of contiguous oligonucleotides (FIG. 4K). In this embodiment, the probe can be understood as comprises a first oligonucleotide only (see for example, FIG. 4K), which comprises self-complementary regions capable of forming stem-loop structure, wherein said self-complementary regions are substantially complementary to each other which form the double-stranded portion of the probe. The stem part can be located any part of oligonucleotide and has a length of 4 to 20 nucleotides. The 3' part of the oligonucleotide is preferably complementary to the target sequence. It can have a blunt end, or 3' protruding end or 5' protruding end. Blunt end, or 3' protruding end is preferred form.

The first oligonucleotide of the probe is capable of being consumed during amplification. Alternatively, both the first and second oligonucleotides are capable of being consumed during amplification. It is preferred that the first oligonucleotide is designed to be consumed, while the second oligonucleotide may remain unchanged in a reaction.

The first oligonucleotide of the probe may be extendable, thereby acting as a primer. Alternatively, the first oligonucleotide is blocked at the 3' end and second oligonucleotide is blocked at the 3' end, thereby being non-extendable.

Each probe comprises a detectable label which is capable of producing a changeable signal which is characteristic of the presence or absence of a double-stranded portion between the first and second oligonucleotides of that probe.

Furthermore, at least two of the probes comprise the same detectable label(s) or different detectable labels(s) with undistinguishable emission spectra.

The label on the probe may be a fluorophore, or the probe may comprise an interactive pair of labels, for example fluorophores and/or non-fluorophore dyes. One example of such interactive labels is a fluorophore-quencher pair. The label on the probe can be located anywhere as long as it interacts with other labels or other entities such as G nucleotides.

In some embodiments, the first oligonucleotide comprises a first label and the second oligonucleotide comprises second label. Preferably, the first label is a fluorophore and the second label is a quencher, or vice versa.

In other embodiments, the probe comprises two labels, the labels being a FRET pair. Preferably one label is on the first oligonucleotide and the second label is on the second oligonucleotide.

Additionally, both the first and second oligonucleotides can also comprise a plurality of label moieties. For example, both the first oligonucleotide and the second oligonucleotide may comprise both a fluorophore and a quencher.

Typically, the fluorophore and the quencher are attached to the oligonucleotides such that when the first oligonucleotide is bound to an unlabelled template sequence (e.g., a target), the fluorophore and the quencher are separated.

Alternatively, the fluorophore and the quencher are attached to the oligonucleotides such that when the first oligonucleotide is bound to an unlabelled template sequence (e.g., a target), the fluorophore and the quencher are brought into close proximity and hence the fluorophore is quenched.

"Fluorophore" as used herein to refer to a moiety that absorbs light energy at a defined excitation wavelength and emits light energy at a different defined wavelength.

Examples of fluorescence labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red and Texas Red-X.

As used herein, the term "quencher" includes any moiety that is capable of absorbing the energy of an excited fluorescent label when it is located in close proximity to the fluorescent label and capable of dissipating that energy. A quencher can be a fluorescent quencher or a non-fluorescent quencher, which is also referred to as a dark quencher. The fluorophores listed above can play a quencher role if brought into proximity to another fluorophore, wherein either FRET quenching or contact quenching can occur. It is preferred that a dark quencher which does not emit any visible light is used. Examples of dark quenchers include, but are not limited to, DABCYL (4-(4'-dimethylaminophenylazo) benzoic acid) succinimidyl ester, diarylrhodamine carboxylic acid, succinimidyl ester (QSY-7), and 4',5'-dinitrofluorescein carboxylic acid, succinimidyl ester (QSY-33), quencherl, or "Black hole quenchers" (BHQ-1, BHQ-2 and BHQ-3), nucleotide analogs, nucleotide G residues, nanoparticles, and gold particles.

The interactive label pair can form either FRET or a contact quenching relationship. It is preferred that for effective contact quenching, the fluorophores and quencher are at a distance of about 0-10 nucleotides. It is more preferred that the fluorophores and quencher are at a distance of about 0-5 nucleotides. It is most preferred that the fluorophores and quencher are at a distance of about 0-2 nucleotides. The quencher is preferably a non-fluorescent entity. The quencher may be a nanoparticle. A nanoparticle may be a gold nanoparticle. It is also possible that the quencher is a G residue or multiple G residues.

The label or combination of labels on each probe are capable of producing a changeable signal which is characteristic of the presence or absence of a double-stranded portion between the first and second oligonucleotides of that probe. It can be seen therefore that the function of the label is to facilitate the determination of whether the first oligonucleotide is bound to the second oligonucleotide or to the target nucleic acid, and in particular whether or not the first oligonucleotide is bound to the second oligonucleotide.

At least one label is attached to the first oligonucleotide or to the second oligonucleotide. The label either increases or decreases fluorescence emission when the first oligonucleotide is bound to the second oligonucleotide.

Preferably, the probe comprises a first label and a second label, wherein at least one label is capable of producing a detectable signal and wherein the signal strength is affected by the proximity of the two labels.

In some embodiments of the invention, the first label is attached to one strand of the double stranded portion and the second label is attached to the opposite strand of the double stranded portion of the probe such that said first label and second label are in close proximity when the probe's internal duplex is formed.

In other embodiments, the first label is attached to the first oligonucleotide, and the second label is attached to the second oligonucleotide such that said first label and second label are in close proximity when the probe's internal duplex is formed.

In some embodiments of the invention, the first oligonucleotide does not comprise a label. In other embodiments, the second oligonucleotide comprises a single label which is capable of changing fluorescence emission when hybridised with the first oligonucleotide.

In some embodiments, the first label is attached to the first oligonucleotide and the second label is attached to the second oligonucleotide such that said first label and second label are in close proximity when the probe's internal duplex is formed. Preferably, the first label is attached to the second region of the first oligonucleotide and the second label is attached to the region of the second oligonucleotide which is complementary to the second region of the first oligonucleotide such that the first and second labels are brought into close proximity upon formation of the probe's internal duplex. Examples of such embodiments are shown in FIGS. 4A, 4B and 4C.

In some aspects of the invention, the first oligonucleotide of the probe does not comprise a label, but the second oligonucleotide of the probe comprises at least one, preferably two, labels.

In one embodiment of this aspect, the second oligonucleotide comprises a first label and a second label. The first label is attached at or near one end of second oligonucleotide and the second label is attached at or near the other end of the second oligonucleotide, whereby when the second oligonucleotide is not hybridised with the first oligonucleotide, the second oligonucleotide is in a random-coiled or a stem-loop structure which brings the first label and second label in close proximity. When the second oligonucleotide is hybridised with the first oligonucleotide, the two labels are held away from each other. Examples of such embodiments are shown in FIGS. 4D, 4E and 4F.

As is known in the prior art, a double-labelled oligonucleotide (equivalent to the second oligonucleotide in this invention) can form a random-coiled structure when it is in single-stranded form and at certain permissive temperatures. This kind of linear oligonucleotide probes in solution behaves like a random coil: its two ends occasionally come close to one another, resulting in a measurable change in energy transfer. However, when the probe binds to its template, the probe-template hybrid forces the two ends of the probe apart, disrupting the interaction between the two terminal moieties, and thus causing a fluorescence emission change.

A double-labelled oligonucleotide can also form a stem-loop structure known as molecular beacon. Molecular beacon probes are single-stranded oligonucleic acid probes that can form a hairpin structure in which a fluorophore and a quencher are usually placed on the opposite ends of the oligonucleotide. At either end of the probe short complementary sequences allow for the formation of an intramolecular stem, which enables the fluorophore and the quencher to come into close proximity. The loop portion of the molecular beacon is complementary to a target nucleic acid of interest. Binding of this probe to its target nucleic acid of interest forms a hybrid that forces the stem apart. This causes a conformation change that moves the fluorophore and the quencher away from each other and leads to a more intense fluorescent signal (Tyagi S, and Kramer F. R., Nature Biotechnology, Vol. 14, pages 303-308 (1996); Tyagi et al., Nature Biotechnology, Vol. 16, pages 49-53 (1998); Piatek et al., Nature Biotechnology, Vol. 16, pages 359-363 (1998); Marras S. et al., Genetic Analysis: Biomolecular Engineering, Vol. 14, pages 151-156 (1999); Tpp I. et al, BioTechniques, Vol 28, pages 732-738 (2000)).

In the present invention, one type of the second oligonucleotides, which can be a molecular beacon-like oligonucleotide, is part of a double-stranded portion of a probe. The differences of the present invention from the prior art technologies are that the second oligonucleotide may not hybridise to the target sequence, but to the second region of the first oligonucleotide which may be unrelated to the target sequence. The second oligonucleotide may be capable of hybridising to the target sequence, but it is designed that it may not be able to hybridise to the target sequence in a real amplification reaction. The second oligonucleotide may contain sequence which is incapable of binding a target sequence strongly. During an extension and annealing step of amplification, the temperature may be too high for the second oligonucleotide to hybridise to the target sequence. While during the signal collection step, which often is carried out after an extension step, the temperature may be low, but the target sequence may be unavailable for the second oligonucleotide to hybridise, as the target sequence to be amplified may become double-stranded due to the extension of amplification primer already take place. Therefore, during signal collection step, the second oligonucleotide may only be able to hybridise to the unconsumed first oligonucleotide of the probe.

In another aspect, the first oligonucleotide does not comprise a label and the second oligonucleotide comprises a label. When the second oligonucleotide hybridises to the first oligonucleotide to form the double-stranded portion of the probe, the label changes its detectable signal emission relative to the emission of the label when in the single-stranded form of the second oligonucleotide. This may be because either the label is brought into close proximity with a nucleotide or nucleotides in the first oligonucleotide, or the label is held away with a nucleotide or nucleotides in the second oligonucleotide.

It is known in the prior art that the emission of a fluorescence dye can be changed when in close proximity to certain nucleotides, for example a G nucleotide.

In other embodiments, the first oligonucleotide of the probe does not comprises a label and the probe comprises two second oligonucleotides which are capable of hybridising adjacently or substantially adjacently to different parts of the second region of the first oligonucleotide, wherein one of the second oligonucleotides is attached with a first label, and the other second oligonucleotide is attached with a second label, such that when the two second oligonucleotides are hybridised to the first oligonucleotide, the two labels are brought in close proximity and one label affects the signal from the other.

This close proximity may, for example, cause either FRET or contact quenching relationship. The two second oligonucleotides that hybridise to the first oligonucleotide are part of the probe. The two labelled second oligonucleotides are designed to not hybridise to amplified target sequence, but to hybridise to the unconsumed first oligonucleotide. Examples of such embodiments are given in FIGS. 4I and 4J.

In yet other embodiments, the first and second oligonucleotides of a probe are joined by a linker moiety which comprises nucleotides or a non-nucleotide chemical linker, allowing the first oligonucleotide and second oligonucleotide to form a stem-loop structure, wherein the first and second oligonucleotides are each labelled such that, when the probe forms an internal stem-loop structure, the labels are brought into close proximity and one label affects the signal from the other.

The linker may, for example, be a simple moiety of formula $(CH_2)_n$ or a linker which is functionally equivalent thereto. (n is preferably 1-100 or 1-50). Preferably, the linker is an oligonucleotide which is contiguous with the first and second oligonucleotides.

At least two of the probes in the amplification reaction mixture comprise the same detectable label or a different detectable label with undistinguishable emission spectra.

In multiplex reactions, two or more probes are used to assay for the presence of two or more target nucleic acids. This does not necessary mean, however, that different distinguishable labels are needed for each of the different probes. Each probe will have a characteristic melting profile which will be dependent on the features of its internal duplex. Therefore, provided that two or more probes have distinguishable melting characteristics, the same label(s) can be used for those probes. In other words, different probes which are labelled with the same labels or labels having undistinguishable emission spectra must have different melting characteristics, preferably different melting temperatures ($T_m$). These different melting characteristics will allow the individual probes to be identified and/or quantified in step (c).

As used herein, the term "melting characteristics" includes the melting profile of a probe (preferably measured by detecting the signal from the label(s) on that probe as function of temperature) and/or the melting temperature ($T_m$) of a probe.

When the melting characteristics of probes are said to be "different", it will be understood that the differences are to be measured under the same or control conditions.

In some embodiments of the invention, two or more probes are labelled with the same detectable label. For example, the first oligonucleotides of at least 2, 3, 4, 5, 6, 7, 8, 9, 10, 20 or 30 or more different probes may all be labelled with the same label and/or the second oligonucleotides of at least 2, 3, 4, 5, 6, 7, 8, 9, 10, 20 or 30 or more different probes may all be labelled with the same label.

In step (b), an amplification reaction is performed on the sample/amplification reaction mixture wherein, when a target nucleic acid is present, the first oligonucleotides which are substantially complementary to part of that target nucleic acid are consumed during the amplification reaction.

The amplification reaction can be carried out under conditions known in the art such that the first oligonucleotides which are substantially complementary to part of the target nucleic acid are consumed.

Preferably, the amplification comprises at least one denaturing step, at least one annealing step and at least one primer extension step.

More preferably, the amplification is a thermal cycling amplification comprising two or more denaturing, annealing, and primer extension steps.

Preferred amplification reactions include PCR, SDA, NASBA, LAMP, 3SR, ICAN, TMA, Helicase-dependent isothermal DNA amplification and the like. PCR is a preferred amplification method. If the amplification is PCR, the conditions comprise thermally cycling the reaction.

When a target nucleic is present in the sample, at least some of the first oligonucleotides which are complementary to part of the target nucleic acids will hybridise thereto under appropriate reaction conditions. The first oligonucleotides will therefore be consumed.

The consumption of the probes is achieved through hybridisation of the probe to the target sequence, which may be followed by incorporation of the probe into the amplified product or/and degradation of the probe during the amplification step. In other words, after consumption, the first oligonucleotide is no longer able to reconstitute the probe of which it previously formed a part.

In an amplification reaction, the probe of the present invention can be constituted by adding the first and second oligonucleotides in the reaction at any ratio of the second oligonucleotide to the first oligonucleotide, for example preferably more than 1, or may be more than 0.1 and less than 1. Thus the first and second oligonucleotides may be added to the amplification reaction mixture independently.

Depending on the type of assay and the type of label that is actually used, the signal from the probe (e.g. fluorescence emission) may either increase or decrease when the first oligonucleotide is consumed. Reference is made, for example, to the embodiments shown in FIG. 4. In FIGS. 4A-4C, the consumption of the probe leads to an increase in fluorescence because the quencher attached to the first oligonucleotide is consumed, thus allowing the fluorophore which is attached to the second oligonucleotide to emit its signal. On the contrary, in FIGS. 4D-4F, the consumption of the first oligonucleotide releases the dual end-labelled second oligonucleotide allowing the fluorophore and quencher to juxtapose one another, thus leading to a reduction in signal from the fluorophore.

In one embodiment, the first oligonucleotide of the probe is extendable and acts as the forward or reverse primer. The first oligonucleotide of the probe may be one of the amplification primers, which is capable of being incorporated into an amplified product, thereby being consumed (see for example FIG. 6). In a PCR, the first oligonucleotide of the probe pairs with another amplification primer for the opposite strand to perform the amplification. During signal collection step, or the step of measuring the melting profile of the probe, the incorporated first oligonucleotide of the probe is not available to form the duplex of the probe's internal double stranded portion. The amount of unconsumed first oligonucleotide of the probe which is able to form the probe duplex can be measured and determined, and the signal can be transformed to the amount of the first oligonucleotide being consumed, thereby determining which or how much of the target sequence is present in a sample. When the first oligonucleotide acts as a primer, the second oligonucleotide preferably does not act as a primer.

In another embodiment of the present invention, the first oligonucleotide of the probe is degraded during amplification. The first oligonucleotide may, for example, comprise nucleotides or non-nucleotide chemicals which are sensitive to a digestion agent. In a further example, upon hybridising to the target sequence the first oligonucleotide can be degraded by the digestion agent. For example, the first oligonucleotide can comprise RNA nucleotides. When the first oligonucleotide hybridises to the target sequence, it can be degraded by enzymes with the RNase H activity. It can be designed such that the first oligonucleotide is not able to be degraded when hybridised to the second oligonucleotide to form the double stranded portion of the probe. The first oligonucleotide can also be degraded by an exonuclease. For example, the 3' nucleotide of the first oligonucleotide can be degraded by the 3' exonuclease activity of a polymerase. The first oligonucleotide can also be degraded by an endonuclease, for example by a restriction enzyme upon hybridisation to a target nucleic acid.

It is preferred that the first oligonucleotide of the probe is degraded by the 5' exonuclease activity of a DNA polymerase, such as Taq DNA polymerase. In this embodiment, the first oligonucleotide of the probe may be blocked at the 3' end, and hence is therefore non-extendable. The first oligonucleotide hybridises to the target sequence in the region bounded by the forward and reverse primers and can be degraded by a nuclease activity, such as 5' exonuclease activity of Taq polymerase during PCR amplification (see for example FIG. 8). Alternatively, the first oligonucleotide of the probe is not blocked at the 3' end, and hence is therefore extendable. The first oligonucleotide hybridises to the target sequence and can be extended by a polymerase. An amplification primer upstream of the first oligonucleotide is also extended. When the extension of the amplification primer encounter the extension strand of the first oligonucleotide, the entire extension strand of the first oligonucleotide can be degraded by a nuclease activity, such as 5' exonuclease activity of Taq polymerase during PCR amplification (see for example, FIG. 7).

In yet another embodiment of the present invention, the consumption of the first oligonucleotide of the probe can simply be the hybridisation of the first oligonucleotide to the target sequence, whereby the hybridised first oligonucleotide is not available to form double stranded duplex of the probe (see, for example, FIG. 5). It is preferred that amplification is designed to produce a single-stranded product so that the first oligonucleotide of the probe can hybridise to the target sequence during the annealing step and/or after the extension step. The methods to produce single-stranded products can be asymmetric PCR, or a method described in PCDR (PCT/GB2007/003793). The single-stranded amplification strand can form a strong hybrid with the first oligonucleotide; therefore the first oligonucleotide can be regarded as consumed, as it is not readily available to form the internal probe hybrid.

In yet another embodiment of the present invention, the first oligonucleotide of the probe plays a role as a nested inner amplification primer. The first oligonucleotide and an outer amplification primer anneal to the same strand of the target nucleic acid. The outer amplification primer and the first oligonucleotide may be both extended upon hybridisation to the target nucleic acid. The extension strand of the first oligonucleotide may be displaced during the extension of the outer primer if the DNA polymerase comprises a displacement activity. The extension strand of the first oligonucleotide may be degraded during the extension of the outer primer if the DNA polymerase comprises a 5' exonuclease activity.

In some embodiments, an amplification condition can be designed such that at some stages of the amplification, even when the target is present, the probe is not consumed, whereas at other stages of the amplification the probe is consumed. For example, if the amplification is PCR, in the some thermal cycles of amplification, the probe may not be consumed, because the annealing and extension temperature are set too high for the probe to bind. The amplification thermal condition can be designed such that the probes can be consumed at some stages, or the last cycle of the amplification. For example, after thermal cycling the PCR vessels are incubated at a temperature which is set lower than either annealing and extension temperatures of the thermal cycling. This low temperature allows the probe to hybridise to the target nucleic acids, resulting in either extension or degradation of the hybridised probe.

Step (b) may further comprise the step (b1) of measuring cycle by cycle fluorescence emissions (FEs) at various measuring temperatures (MTs). The measuring temperatures (MTs) refers to the temperature at which an emission reading of the label in the probe is taken cycle by cycle to determine the emission amount of a probe.

The emission of a label on the probe is preferably obtained, detected and/or recorded in each cycle in a reaction after the reaction mixture is illuminated or excited by light with a wavelength absorbed by the label. The term "cycle by cycle" refers to measurement in each cycle. The emission reading at a measuring temperature is taken to calculate the emission amount of a remaining probe in a cycle. Emission can be detected, recorded, or obtained continuously or intermittently.

In a continuous recording process, the emission of the probe is monitored and recorded, for example, every 50 ms, every 100 ms, every 200 ms or every 1 s, in each cycle of, for example, a PCR reaction. A three dimensional plot of time, temperature and emission can be formed. In any given cycle, the emission reading at a time point that corresponds to a desired MT is taken to determine the emission amount of the probe in the cycle. In an intermittent recording process, the emission reading is taken only when the reaction temperature reaches a desired MT in each cycle.

For the first oligonucleotides of the probe which are consumed by incorporating into the amplified product or being degraded by a digestion agent, the obtaining of the cycle by cycle fluorescence emissions (FE) is preferably performed after the completion of the extension step at each cycle. For the first oligonucleotides of the probe which are consumed by being hybridised to the target sequence, the obtaining of the cycle by cycle fluorescence emissions (FE) may be performed before the completion of the extension step at each cycle.

Fluorescence emissions (FE) is used herein to refer to baseline corrected fluorescence (dR). Normally, for each well (reaction) and each optical path the raw fluorescence data are fitted over the specified range of cycles using a linear least mean squares algorithm (or other such algorithm) to produce a baseline. The value of the baseline function is calculated for every cycle and subtracted from the raw fluorescence to produce the baseline corrected fluorescence (dR).

The fluorescence intensity data (amplification plots) can be described as a two-component function: a linear component or background and an exponential component that contains the relevant information. To isolate the exponential component, the linear contribution to the fluorescence can be estimated and subtracted. It is a three-step process that is carried out for each amplification plot (i.e. each reaction and each label):

1. Identify the range of cycles during which all contributions to the fluorescence are strictly linear (no exponential increase in fluorescence).
2. Using the fluorescence intensity values during the cycles determined above, fit the data to a straight line (a function predicting the contribution of the linear components throughout the reaction).
3. Subtract the predicted background fluorescence intensity during each cycle. The resulting curve corresponds to the change in fluorescence due to DNA amplification.

When the amplification reaction mixture comprises "n" probes for multiplex detection of "n" nucleic acid targets, first probe has a melting temperature of $T_m1$, the second probe has a melting temperature of $T_m2$, the third probe has a melting temperature of $T_m3$, the k-th probe has a melting temperature $T_mk$, and the n-th probe has a melting temperature of $T_mn$, wherein $T_m1 > T_m2 > T_m3 > \ldots T_mk \ldots > T_mn$, wherein n and k are positive integers, $1 \leq k \leq n$, and $n \geq 2$.

The percentage of a probe's double-stranded form out of the total amount of probes at a particular temperature or at series temperatures may be determined experimentally or predicted which can be done by a computer program. Since the first negative derivative of a probe's melting emission with respect to temperature is plotted to form a normal distribution curve, an ordinary person skilled in the field of statistics could readily define a MT at which a percentage of the total number of a given probe is in duplex form or in single-stranded (i.e. separated) form. Accordingly, a measuring temperature is a temperature at which no more than 20%, for example, of a probe is in single-stranded form. A table may be created listing percentages of double-stranded (ds) and single-stranded forms(s) of each probe at each temperature.

A first fluorescence emission FEa can be obtained at a measuring temperature MTa, at which more than 50% of first probe is in duplex form; second fluorescence emission FEb can be obtained at a measuring temperature MTb, at which more than 50% of second probe is in duplex form; k-th fluorescence emission FEk can be obtained at a measuring temperature MTk, at which more than 50% of k-th probe is in duplex form; n−1 fluorescence emissions FE(n−1) can be obtained at a measuring temperature MT(n−1), at which more than 50% of (n−1)-th probe is in duplex form, n-th fluorescence emission FEn can be obtained at a measuring temperature MTn, at which more than 50% of n-th probe is in duplex form, and optionally a fluorescence emission FE0 can be obtained at a measuring temperature MT0, at which no more than 10% of first probe is in duplex form.

Although the above-mentioned 50% is a preferred amount of probe in the duplex form, it should be appreciated that any percentage can be used, such as 40%, 55%, 70% or 80%. It is preferred that in the step obtaining cycle by cycle a fluorescence emission FEk at a measuring temperature MTk, at which no more than 30% of (k−1)-th probe is in the probe's internal duplex form. It is even preferred that in the step obtaining cycle by cycle a fluorescence emission FEk at a measuring temperature MTk, at which no more than 20% of (k−1)-th probe is in the probe's internal duplex form.

The step (b) may further comprise the step (b2) determining cycle by cycle Actual Consumed Amount of fluorescence emission from consumed probe for each probe, wherein the Actual Consumed Amount of fluorescence emission t of k-th probe is depicted as $ACA_k$. At a particular measuring temperature (MTa), where a probe has certain percentage (dska)% in ds (double-strand) form, the fluorescence emission FE at this measuring temperature MTa contributed by first probe will be $(ds1a)\%*(ACA_1)$, contributed by the second probe will be $(ds2a)\%*(ACA_2)$, contributed by the k-th probe will be $(dska)\%*(ACA_k)$. For example, at 60° C. 70% of probe 1 is in ds form; at 50° C. 80% in ds. The FE contributed by the probe 1 at 60° C. will be $70\%*(ACA_1)$; FE contributed by the probe 1 at 50° C. will be $80\%*(ACA_1)$. If multiple probes are present, the FE will be the total amount contributed by consumed probes of all probes. The calculation of Actual Consumed Amount (ACA) can use the following formula:

At temperature a, the total fluorescence emission will be $$FEa=(ACA1)*(ds1a)\%+(ACA2)*(ds2a)\%+(ACA3)*(ds3a)\% \ldots +(ACAn)*(dsna)\%$$

At temperature b, the total fluorescence emission will be $$FEb=(ACA1)*(ds1b)\%+(ACA2)*(ds2b)\%+(ACA3)*(ds3b)\% \ldots +(ACAn)*(dsna)\%$$

At temperature c, the total fluorescence emission will be $$FEc=(ACA1)*(ds1c)\%+(ACA2)*(ds2c)\%+(ACA3)*(ds3c)\% \ldots +(ACAn)*(dsna)\%$$

And so on. The individual ACA can be calculated from the above formulas.

"*" denotes "multiply by".

It is preferred that the Actual Consumed Amount of each probe is obtained though a computer program which performs the above calculation. Alternatively, the calculation can be done manually.

For example, in an amplification reaction, there are three probes for three target sequences. At temperature 65° C., 5% of the first probe is in duplex form, 0% of the second probe and 0% of third probe is in duplex form. At 60° C., 60% of the first probe is in duplex form, 5% of second probe is in duplex form, 0% of the third probe is in duplex form. At 55° C., 90% of the first probe is in duplex form, 55% of second probe is in duplex form, 5% of third probe is in duplex form. At 45° C., more than 95% of all probes are in duplex form. The first fluorescence emission is collected at 60° C., which is FE60, the second fluorescence emission is collected at 55° C., which is FE55, the third fluorescence emission is collected at 45° C., which is FE45. Optionally before the first fluorescence emission is collected, a fluorescence emission is collected at 65° C. or above, which is FE65. The FE contributed by the actual consumed amount ACA from individual probe is calculated as ds %*(ACA). See the table below:

The individual ACA can be calculated from the above formulas. If we assume 5%*ACA can be neglected. The approximate ACA can be calculated from (1), (2) and (3), where $$ACA1=(EF60)/0.6$$

$$ACA2=((EF55)-0.9/0.6*(EF60))/0.55$$

$$ACA3=(EF45)/0.95-(EF60)/0.6-(EF55-(0.9/0.6)*(EF60))/0.55$$

As a PCR mixture undergoes thermal cycling, the fluorescence emission and actual consumed amount (ACA) are recorded (calculated) and plotted over the number of cycles to form an emission versus cycle plot. In the initial cycles, there is little change in the emission amount which appears as a baseline or a plateau in the plot. As thermal cycling continues, an increase in emission amount above the baseline may be expected to be observed, which indicates that the amplified product (or consumed probes) has accumulated to the extent that fluorescence emission of a probe in the presence of the amplified product (or consumed probe) exceeds the detection threshold of a PCR instrument. An exponential increase in emission amount initiates the exponential phase and eventually reaches another plateau when one of the components in the PCR mixture becomes limiting. The plot usually produces an S-shape curve with two plateaus at both ends and an exponential phase in the middle. In the exponential phase, the emission amount of the probe is increasing by (1+E) fold over the previous amount of each cycle, wherein E is the efficiency of amplification, which ideally should be 100% or 1. It is commonly known that the higher the starting amount of the nucleic acid template from which a product is amplified, the earlier an increase over baseline is observed. As is well known in the art, the emission versus cycle plot provides significant information for attaining the initial copy number or amount of the nucleic acid template.

As is known in the field of real-time PCR, the unknown amount of a nucleic acid template may be quantified by comparing the emission versus cycle plot of the template with standardized plots.

In one embodiment of the present invention, when a plurality of nucleic acid templates are amplified to form a plurality of amplified products, each product is preferably compared with a standard curve formed by the same product. A single product per dilution per PCR mixture can be used to form the standard curve. Preferably, at each dilution, a plurality of products are placed in a single PCR mixture and emission readings of each probe can be measured and plotted to form a standard curve based on methods described in the present invention.

The starting amount of a nucleic acid template in a sample can also be determined by normalizing the template to a

|  | probe1 | | probe2 | | probe3 | | fluorescence |
| --- | --- | --- | --- | --- | --- | --- | --- |
|  | ds % | ACA1 | ds % | ACA2 | ds % | ACA3 | emission |
| 65° C. | 5 | 5% ACA1 | 0 | 0% ACA2 | 0 | 0% ACA3 | FE65 |
| 60° C. | 60 | 60% ACA1 | 5 | 5% ACA2 | 0 | 0% ACA3 | FE60 |
| 55° C. | 90 | 90% ACA1 | 55 | 55% ACA2 | 5 | 5% ACA3 | FE55 |
| 45° C. | 95 | 95% ACA1 | 95 | 95% ACA2 | 95 | 95% ACA3 | FE45 |

FE65 = 5%*ACA1 + 0%*ACA2 + 0%*ACA3 ≈ 0
FE60 = 60%*ACA1 + 5%*ACA2 + 0%*ACA3 (1)
FE55 = 90%*ACA1 + 55%*ACA2 + 5%*ACA3 (2)
FE45 = 95%*ACA1 + 95%*ACA2 + 95%*ACA3 (3)

house-keeping gene or a normalizer in relative relationship to a calibrator without using a standard curve. For example, GAPDH (glyceraldehyde 3-phosphate dehydrogenase) and β-actin are commonly regarded a suitable house-keeping nucleic acid templates or normalizer templates due to their abundance and constant levels of expression in cells. The calibrator can be an untreated sample or a specific cell, tissue or organ used for the normalization of treated samples or targeted cells.

In one embodiment of the present invention, a plurality of nucleic acid templates of interest are amplified and quantified in a single PCR mixture. The starting amount of each nucleic acid template can simultaneously be calculated and normalized to a normalizer. It is also contemplated that a plurality of nucleic acid templates and a normalizer template can be monitored and amplified in the same PCR reaction. It is further contemplated that more than one housekeeping template or normalizer can be amplified along with multiple nucleic acid templates in a single PCR reaction. It is further contemplated that the relative amount among these templates or the ratios between or among these templates can be determined from a single PCR mixture.

Step (c) comprises measuring, at least once, the melting profile of the double-stranded portions between the first and second oligonucleotides of unconsumed probes by detecting the signals from the labels in those probes as a function of temperature,
wherein the melting profile provides an indication of whether or not at least one target nucleic acid has been amplified in said sample/amplification reaction mixture.

To determine the melting (profile) curve for each probe or each set of probes, the reaction mixture is illuminated with light that is absorbed by the labels of the probes and the fluorescence of the reaction is monitored as a function of temperature. More particularly, the fluorescence of the labels is measured as the temperature of the sample is raised (or decreased) until a baseline level of fluorescence is achieved.

The data may be presented as fluorescence vs. temperature plots or as first derivative plots of fluorescence vs. temperature, for example. The two plots are interchangeable, but each focuses the viewer's attention on different aspects of the data. The melting peak (or $T_m$) is best viewed on derivative plots. However, the broadening of the transition and appearance of low melting transitions are easier to observe on fluorescence vs. temperature plots. The point at which there is a shift in the rate of decrease or increase of fluorescence can be more easily identified by viewing a plot of the first derivative of the fluorescence vs. temperature. The point of maximum rate of change is considered the melting temperature of the probe duplex. If one probe has a higher $T_m$, it forms a stronger probe duplex and will consequently melt at a higher temperature than another probe. The distinctly different melting temperatures of different probes allow identification of which probe is consumed during amplification (if the probes have the same label).

In some methods of this invention, fluorescence is monitored as a function of a denaturing gradient. Independent from the type of gradient, however, what is actually monitored is the change in fluorescence caused by the dissociation of the two strands of the double-stranded portion of the probe. The denaturing gradient may be a thermal gradient. In other words, the invention is illustratively directed to a method, characterized in that during or subsequent to the (preferably PCR) amplification, temperature dependent fluorescence is monitored. It is often desirable, however, if the monitoring of temperature-dependent fluorescence is part of a homogeneous assay format such that (PCR) amplification and monitoring temperature dependent fluorescence are carried out in the same reaction vessel without intermediate opening of the reaction chamber.

Melting profile analysis may be obtained by monitoring temperature-dependent fluorescence during melting or hybridisation. Usually, melting curve analyses are performed as slowly as possible in order to generate precise and highly reproducible data, in order to obtain an exact determination of the melting point, which is defined as the maximum of the first derivative of a temperature versus fluorescence plot. However, if the selected time parameters are comparatively short, certain advantages may be seen.

A melting profile may be measured after completion of amplification (post-amplification melting profile), and/or may be measured during amplification at each cycle or at selected cycles (mid-amplification melting profile).

In one embodiment, the temperature-dependent fluorescence is monitored after completion of a PCR reaction. In an alternative embodiment, the temperature-dependent fluorescence is monitored in real-time during a PCR reaction.

In one embodiment during said measuring, the amplified product (amplicon) remains double stranded, thereby involving little, if any, or no detectable change of signals. While in other embodiment, the measuring melting profile may be performed when some of the amplified product is in single-stranded form.

The skilled person will be able to determine, merely from the melting profile after amplification (and without comparing the melting profile with any other melting profiles) whether or not at least one target nucleic acid has been amplified. For example, FIGS. 1 and 2 illustrate the "flatter" curves obtained after amplification, as compared to the more "S" shaped curves which are characteristic of unconsumed probes.

The method of the invention may further comprise a step (d)
(i) comparing at least two melting profiles obtained in (c) and/or
(ii) comparing a melting profile obtained in step (c)
  with a previously-obtained melting profile of the same probes or
  with a melting profile of the same probes obtained in parallel at the same time in control reactions, or
  with a theoretical melting profile of the same probes,
wherein a change in the melting profile provides an indication of whether or not at least one target nucleic acid has been amplified in said sample/amplification reaction mixture.

The melting profile may be measured before amplification takes place (pre-amplification melting profile), and/or is measured after completion of amplification (post-amplification melting profile), and/or is measured during amplification at each cycle or selected cycles (mid-amplification melting profile), A pre-amplification melting profile of the probes may be measured in the same reaction vessel before the start of amplification, or may be measured in a separate reaction vessel where no amplification takes place due to that the reaction mixture lacking one or more ingredients necessary for the amplification. Examples of such ingredients include a dNTP, a polymerase or a target nucleic acid.

It should be noted that the method of the invention does not necessarily require the pre-amplification melting profile to be measured as part of the method of the invention. This profile might be one which is characteristic of the probe or combination of probes in question and which might have been measured previously and/or stored in a retrievable manner, for example in a computer-readable format.

Each probe in the reaction mixture will be specific for a particular target nucleic acid. Different probes are used which are labelled with the same label or labels having undistinguishable emission spectra, and the probes are selected so as to have different melting characteristics, for example different melting profiles or different melting temperatures ($T_m$s).

The melting profile which is obtained in step (c) will be an amalgamation of the melting profiles of the probes which are present in the amplification reaction mixture. Due to the fact that different probes are selected so as to have different melting profiles, the individual contributions made by each probe to the combined melting profile will be separable by those skilled in the art, either manually or preferably by computer-implemented means. In this way, the presence or absence of particular probes, and hence the presence or absence of particular target nucleic acids in the sample, can be distinguished from one another.

Comparison of the pre- and post-amplification melting profiles of each probe may identify which feature of the curve that is a signature for a particular probe has disappeared or has been reduced, therefore indicating that that particular probe is consumed during amplification and further indicating that the corresponding target is present in the sample.

It is preferred that the comparison of the melting profiles of probes before amplification taking place and after completion of amplification or after some cycles of amplification is done by a computer program. The computer program determines which probe or how much the probe is consumed, which is indicative of which target or how much of the corresponding target is present in a sample.

The melting temperatures ($T_m$) of probes with the same label(s) or different label(s) with indistinguishable emission spectra will generally be different from the melting temperatures of each other similarly-labelled probe. In one embodiment, multiple probes in a set are each labelled with the same label (or different label(s) with indistinguishable emission spectra) and each probe has a distinct melting temperature range. In a multiplex assay, when a reaction temperature rises from the hybridising temperature to a denaturing temperature, the probe duplex with the lowest $T_m$ unwinds first, the probe duplex with the next highest $T_m$ separates next, and the probe duplex with the highest $T_m$ denatures last. Concurrently, the fluorescent emission of the label attached to the probe changes in proportion to the rising reaction temperature due to the incremental melting of the probe duplex, hence allowing each probe to be distinguished in the combined melting profile. The shape and position of a melting curve is a function of GC/AT ratio, length, and the sequence of the double-stranded portion of the probe.

Preferably, the $T_m$s of probes with the same label(s) or different label(s) with indistinguishable emission spectra are at least 2° C., preferably at least 3° C., 4° C. or 5° C. different from other similarly-labelled probes.

In one aspect of the present invention, real time fluorescence monitoring of a PCR reaction is used to acquire a probe's melting curves during the PCR reaction. The temperature cycles of PCR that drive amplification alternately denature the accumulating product and the labelled probes at a high temperature, and anneal the primers and at least one strand of the probe to the product at a lower temperature, thereby consuming some probes. Plotting fluorescence as a function of temperature as the sample is heated through the dissociation temperature of probe's internal double stranded portion of the remaining (unconsumed) probe gives a probe's melting curve. Thus continuous monitoring of fluorescence during a PCR reaction provides a system for detecting changes of probe concentrations by probe melting profiles.

Such a system, particularly a HRM-PCR system, can be used to differentiate the remaining probes separated by less than 2° C. in melting temperature.

The invention also provides a method for monitoring a PCR amplification of at least two nucleic acid targets, said method comprising:
(a) contacting a sample comprising one or more target nucleic acids with an amplification reaction mixture comprising:
    (i) one or more pairs of forward/reverse oligonucleotide primers, wherein the primer pairs are capable of amplifying one or more target nucleic acids, if present in the sample, and a nucleic acid polymerase,
    (ii) two or more probes, wherein each probe comprises
        a first oligonucleotide which comprises a first region which is substantially complementary to part of one target nucleic acid and a second region, and at least one second oligonucleotide which comprises a region which is substantially complementary to a second region of the first oligonucleotide, such that the first and second oligonucleotides are capable of forming a double-stranded portion,
    wherein each probe comprises a detectable label which is capable of producing a changeable signal which is characteristic of the presence or absence of a double-stranded portion between the first and second oligonucleotides of that probe, and
    wherein the at least two of the probes comprise the same detectable label or different detectable labels with undistinguishable emissions spectra
    wherein the melting characteristics of the double-stranded portions between the first and second oligonucleotides of each of such probes are different;
(b) performing an amplification reaction on the sample/amplification reaction mixture wherein, when a target nucleic acid is present, the first oligonucleotides which are substantially complementary to part of that target nucleic acid are consumed during the amplification reaction; and
    wherein the step (b) further comprises the step (b1) obtaining cycle by cycle fluorescence emissions (FE) at various measuring temperatures (MT), wherein said fluorescence emissions (FE) are baseline corrected fluorescence (dR),
    wherein when said amplification reaction mixture comprises "n" probes for multiplex detection of "n" nucleic acid targets, wherein first probe has a melting temperature of $T_m1$, second probe has a melting temperature of $T_m2$, third probe has a melting temperature of $T_m3$, n-th probe has a melting temperature of $T_mn$, wherein $T_m1 > T_m2 > T_m3 \ldots > T_mn$, wherein the percentages of the double-stranded form of each probe at a particular temperature or different temperatures are determined experimentally or are calculated in theory by a computer program, wherein a first fluorescence emission FEa is obtained at a measuring temperature MTa, at which more than 50% of first probe is in duplex form, second fluorescence emission FEb is obtained at a measuring temperature Mtb, at which more than 50% of second probe is in duplex form, n−1 fluorescence emission FE(n−1) is obtained at a measuring temperature MT(n−1), at which more than 50% of (n−1)th probe is in duplex form, n-th fluorescence emission FEn is obtained at a measuring temperature MTn, at which more than 80% of n-th probe is in duplex form, and optionally a fluorescence emission FE0 is obtained at a measuring temperature MT0, at which no more than 10% of first probe is in duplex form, wherein n is a positive integer and n≥2,
    wherein the step (b) may further comprise the step (b2) determining cycle by cycle Actual Consumed Amount of fluorescence emission from consumed probe for each probe, wherein the Actual Consumed Amount of fluorescence emission t of k-th probe is depicted as $ACA_k$. At a particular measuring temperature (MTa), wherein a probe has certain percentage (dska)% in ds (double-strand) form, the fluorescence emission FE at this measuring temperature MT contributed by first probe will be $(ds1)\%*(ACA_k)$, contributed by the second probe will be $(ds2a)\%*(ACA_2)$, contributed by the k-th probe will be $(dska)\%*(ACA_k)$. For example, at 60° C. 70% of probe 1 is in ds form; at 50° C. 80% in ds form. At 60° C. the FE contributed by the probe 1 will be $70\%*(ACA_1)$; at 50° C. FE contributed by the probe 1 will be $80\%*(ACA_1)$. If multiple probes are present, the FE will be the total amount contributed by consumed probes of all probes. The calculation of Actual Consumed Amount (ACA) can use the following formula:

At temperature "a", the total fluorescence emission will be $$FEa=(ACA1)*(ds1a)\%+(ACA2)*(ds2a)\%+(ACA3)*(ds3a)\% \ldots +(ACAn)*(dsna)\%$$

At temperature "b", the total fluorescence emission will be $$FEb=(ACA1)*(ds1b)\%+(ACA2)*(ds2b)\%+(ACA3)*(ds3b)\% \ldots +(ACAn)*(dsna)\%$$

At temperature "c", the total fluorescence emission will be $$FEc=(ACA1)*(ds1c)\%+(ACA2)*(ds2c)\%+(ACA3)*(ds3c)\% \ldots +(ACAn)*(dsna)\%$$

And so on. The individual ACA can be calculated from the above formulas.

wherein the emission amount of each probe is obtained though a computer program or is done manually.

The invention also provides a computer software product for use with the method of the invention adapted, when run on suitable data processing means, for comparing melting profiles of probes and/or quantifying a real time PCR amplification of multiplex targets which performs the calculation of the florescence emission and Actual Consumed Amount (ACA).

Generally, ACA can be calculated manually once the emission values are acquired through a PCR instrument and the percentages of the double stranded form of each probe at each temperature are known. However, it is frequently desirable to automate the calculation through the use of a computer system.

In a further embodiment, the invention relates to a computer system comprising a computer memory having a computer software program stored therein, wherein the computer software program, when executed by a processor or in a computer, performs methods according to the present invention. In a preferred embodiment, a computer program product comprises a computer memory having a computer software program stored therein, wherein the computer software program performs a method comprising the step of calculating the ACA and/or determination of features of melting profiles during amplification or at the end amplification.

As will be appreciated by those skilled in the art, a computer program product of the present invention, or a computer software program of the present invention, may be stored on and/or executed in a PCR instrument and used to calculate the amount of each probe.

The invention further provides a kit for assaying for one or more nucleic acid targets, which kit comprises a probe comprising:
  a first oligonucleotide of 15-150 nucleotides which comprises a first region which is substantially complementary to part of one target nucleic acid and a second region, and
  at least one second oligonucleotide of 4-150 nucleotides which comprises a region which is substantially complementary to the second region of the first oligonucleotide, such that the first and second oligonucleotides are capable of forming a double-stranded portion,
  wherein each probe comprises a detectable label or detectable combination of labels which is/are capable of producing a changeable signal which is characteristic of the presence or absence of a double-stranded portion between the first and second oligonucleotides of that probe,
and wherein
  (a) the first oligonucleotide of the probe does not comprise a label, the second oligonucleotide comprises a first label and a second label, wherein the first label is attached at or near one end of second oligonucleotide and the second label is attached at or near the other end of the second oligonucleotide, whereby when the second oligonucleotide is not hybridised with the first oligonucleotide, the second oligonucleotide is in a random-coiled or a stem-loop structure which brings the first label and second label in close proximity and wherein when the second oligonucleotide is hybridised with the first oligonucleotide, the two labels are held away from each other; or
  (b) the first oligonucleotide does not comprise a label and the second oligonucleotide comprises a label, wherein when the second oligonucleotide hybridises to the first oligonucleotide to form the double-stranded portion of the probe, the label is capable of changing its detectable signal emission relative to the emission of the label when in the single-stranded form of the second oligonucleotide; or
  (c) the first oligonucleotide of the probe does not comprises a label, the probe comprises two second oligonucleotides which are capable of hybridising adjacently or substantially adjacently to different parts of the second region of the first oligonucleotide, wherein one of the second oligonucleotides is attached with a first label, and the other second oligonucleotide is attached with a second label, such that when the two second oligonucleotides are hybridised to the first oligonucleotide, the two labels are brought in close proximity and one label affects the signal from the other.

The invention also provides the use of a probe as defined in (a)-(d) above in a method of the invention.

The invention also provides the use of a probe comprising
  a first oligonucleotide of 15-150 nucleotides which comprises a first region which is substantially complementary to part of one target nucleic acid and a second region, and at least one second oligonucleotide of 4-150 nucleotides which comprises a region which is substantially complementary to the second region of the first oligonucleotide, such that the first and second oligonucleotides are capable of forming a double-stranded portion,
  wherein each probe comprises a detectable label or detectable combination of labels which is/are capable of producing a changeable signal which is characteristic of the presence or absence of a double-stranded portion between the first and second oligonucleotides of that probe,
and wherein
  (a) the first label is attached to the second region of the first oligonucleotide and the second label is attached to the region of the second oligonucleotide which is complementary to the second region of the first oligonucleotide such that the first and second labels are brought into close proximity upon formation of the probe's internal duplex, or
  (b) the first and second oligonucleotides of the probe are joined by a linker moiety which comprises nucleotides or a non-nucleotide chemical linker, allowing the first oligonucleotide and second oligonucleotide to form a stem-loop structure, wherein the first and second oligonucleotides are each labelled such that, when the probe forms an internal stem-loop structure, the labels are brought into close proximity and one label affects the signal from the other,
in a method as disclosed herein.

Another aspect of the invention is directed to a method for assaying a sample for one or more variant nucleotides on the target nucleic acids, said method comprising:
(a) contacting a sample comprising target nucleic acids with an amplification reaction mixture comprising:
 (i) one or more pairs of forward/reverse oligonucleotide primers, wherein the primer pairs are capable of amplifying one or more target nucleic acids, if present in the sample,
 (ii) at least one pair of probes, wherein first probe in the pair comprises sequence complementary to the wild-type target nucleic acid sequence (the normal sequence), second probe in the pair comprises sequence complementary to the target nucleic acid sequence containing variant nucleotides (for example, SNP, mutated nucleotides etc), wherein each probe in the pair comprises
  a first oligonucleotide which comprises a first region which is substantially complementary to part of one target nucleic acid and a second region, and at least one second oligonucleotide which comprises a region which is substantially complementary to the second region of the first oligonucleotide, such that the first and second oligonucleotides are capable of forming a double-stranded portion,
  wherein each probe in the pair comprise the same second oligonucleotide,
 wherein each probe comprises a detectable label or detectable combination of labels which is/are capable of producing a changeable signal which is characteristic of the presence or absence of a double-stranded portion between the first and second oligonucleotides of that probe, and
 wherein at least two of the probes comprise the same detectable label or different detectable labels with undistinguishable emission spectra and wherein the melting characteristics of the double-stranded portions between the first and second oligonucleotides of each of such probes are different;
(b) performing an amplification reaction on the sample/amplification reaction mixture wherein, when a target nucleic acid is present, the first oligonucleotides of probes which are substantially complementary to part of that target nucleic acid are consumed during the amplification reaction; and
(c) measuring, at least once, the melting profile of any double-stranded portions between the first and second oligonucleotides of any unconsumed probes by detecting the signal(s) from the labels in those probes as a function of temperature, wherein the melting profile provides an indication of whether or not at least one target nucleic acid has been amplified in said sample/amplification reaction mixture.

The same second oligonucleotide in the pair of the probe may comprise universal base or Inosine which corresponds to the variant nucleotide in the target nucleic acid sequence. The universal base may be 3-nitropyrrole 2'-deoxynucleoside, 5-nitroindole, pyrimidine analog or purine analog. Inosine occurs naturally in the wobble position of the anticodon of some transfer RNAs and is known to form base pairs with A, C and U during the translation process (FIG. 17).

For scanning multiple mutations or SNPs in a target sequence, multiple first oligonucleotides of different probes hybridising to different sites of the same amplified product may be included in a reaction. The probes may contain a competing pair of probes, the first probe in the pair hybridises to the wild-type (normal nucleotide) sequence; the second probe in the pair hybridises to target sequence containing the variant (mutated) nucleotides. When the wild-type target sequence is present, the probe complementary to the wild-type target sequence is consumed. When the target sequence having the variant nucleotide is present, the probe complementary to the variant target sequence is consumed. The multiple first oligonucleotides may hybridise to the same strand of target nucleic acid sequence adjacent to each other or with some overlapping region between adjacent first oligonucleotides (FIG. 17).

Another aspect of the invention is directed to a combination of primers/probes for monitoring, detecting or quantifying a plurality of nucleic acid templates in a single amplification reaction based on the properties of the melting profile of the primer or probe hybridised with the primer extension product which are amplified from the nucleic acid templates (FIG. 14).

The combination of primers and probes may comprise: first primers, second primers and first probes (FIG. 14A),
 wherein said second primer comprises, in 3' to 5' order, a 3' target specific priming portion substantially complementary to a sequence of a target nucleic acid, a probe-complementary portion comprising a sequence capable of hybridising to the first probe, and 5' universal portion comprising sequence identical or substantially identical to the sequence of the first primer,
 wherein the first probe capable of hybridising to the second primer comprises a first label, the first primer comprises a second label such that the first label and second label are capable of interacting when the two labels are brought into proximity,
 wherein the first primer is capable of extending on the template complementary to the extension strand of the second primer,
 wherein upon hybridisation of the first probe to the first primer extension product, the two labels are brought into proximity, thereby generating detectable signal.

In one embodiment, in the combination of primers and probes, the first primer is an universal primer, the first probe is an universal probe, the second primers constitute a set of primers in which each second primer is attached with the same label or labels with undistinguishable emission spectra. In the set of second primers, the 3' target specific priming portion of each second primer is capable of hybridising to each target specifically, wherein the first probe hybridises to each second primer or the extension strands of the first primer with different $T_m$ or melting profile specific for each target. The different $T_m$s or different melting profiles of the first probe for each target are distinguishable from one another such that the distinct $T_m$ or melting profile will provide the information if a target is present in a sample (FIG. 14B).

In another embodiment, the probe-complementary portion and the 3' target specific priming portion of the second primer are not substantially overlapping, wherein the probe-complementary portion comprises sequence which may not be related to the target sequence.

In a further embodiment, the probe-complementary portion is substantially overlapping with the 3' target specific priming portion of the second primer, or the probe-complementary portion is embedded in the 3' target specific priming portion of the second primer (FIG. 14A), wherein $T_m$ of the duplex of said second primer hybridised with the target sequence is higher than the $T_m$ of the duplex of said second primer hybridised with the first probe such that if a target is present, the second primer forms stronger hybrids with the target.

One of the labels can be either a quencher or a fluorophore. The hybridisation of the first probe with the extension strand of the first primer brings two labels in contact quencher relationship or FRET relationship.

Another aspect of the invention is directed to a method for monitoring, detecting or quantifying a plurality of nucleic acid templates in a single amplification reaction.

The method for detecting/quantifying a target nucleic acid or multiple target nucleic acids in a nucleic acid population, said method comprising:
(a) treating the nucleic acid population with a combination of primers and probes, or a set of combinations of primers and probes, as described above, under amplification conditions, wherein second primer anneal to the target nucleic acid, and is extended, the extension strand of the second primer is separated from template and participates in the another cycle of primer annealing, and extension,
wherein the concentration of second primer is lower than the concentration of first primer in the reaction mixture, the first primer participates in the amplification when the second primer is running low or running out, whereby the first primer is incorporated into the amplification product;
(b) detecting signal emissions from the hybridisation of the first probe with the extension product of the first primers at each cycle;
(c) measuring melting profile of the duplex of the first probe and the extension product of the first primer, wherein said melting profile is measured by illuminating the reaction mixture and monitoring the fluorescence as a function of temperature, wherein a signature Tm or melting profile is an indicative of the presence of a target sequence.

It is preferred that the amplification is an asymmetric amplification, wherein the single stranded first primer extension strands are accumulated during amplification. This can be achieved by using different ratio of forward primer and reverse primer.

Another aspect of the invention is directed to a kit for monitoring, detecting or quantifying a plurality of nucleic acid templates in a single amplification reaction.

The kit for detecting/quantifying a target nucleic acid or multiple target nucleic acids in a nucleic acid population, said kit comprises: a combination of primers and probes, or a set of combinations of primers and probes, as described above, wherein said combination of primers and probes comprises: first primers, second primers and first probes,
wherein said second primer comprises, in 3' to 5' order, a 3' target specific priming portion substantially complementary to a sequence of a target nucleic acid, a probe-complementary portion comprising a sequence capable of hybridising to the first probe, and 5' universal portion comprising sequence identical or substantially identical to the sequence of the first primer,
wherein the first probe capable of hybridising to the second primer comprises a first label, the first primer comprises a second label such that the first label and second label are capable of interacting when the two labels are brought into proximity,
wherein the first primer is capable of extending on the template complementary to the extension strand of the second primer,
wherein upon hybridisation of the first probe to the first primer extension product, the two labels are brought into proximity, thereby generating detectable signal.

The first probe capable of hybridising to the extension strand of the first primer can contain target specific sequence or arbitrary sequence and can have any length. Generally, it may be 4 to 60 nucleotides long, preferably 5 to 25 nucleotides long.

The probe-complementary portion of the second primer comprises sequence capable of hybridising to the first probe. It is designed that the duplex of probe-complementary portion and the first probe has distinct Tm or melting profile for each target sequence.

The 5' universal portion of the second primer comprises sequence identical or substantially identical to the 3' priming portion of the first primer or the whole sequence of the first primer. It is designed that the first primer can anneal to the template generated by the second primer replication product and initiate prime extension.

In one embodiment, the first primer is a target specific primer, which comprises the 3' priming portion which is complementary to a region of target nucleic acid. In this embodiment, the first probe included in a reaction comprises sequence capable of hybridising to the extension strand of the first primer and being adjacent to the first primer.

In a preferred embodiment, the first primer is an universal primer, the first probe is an universal probe, the second primers constitute a set of multiple primers, in which the 3' target specific priming portion of each second primer is capable of hybridising to each target specifically and priming amplification of each target, wherein the probe-complementary portion of each second primer comprises sequence capable of hybridising with the first probe with distinct hybridisation/dissociation property for each second primer.

For SNP genotyping or detecting variant nucleotide, the second primer may be allele-specific primer, wherein a terminal nucleotide of the second primer is selected to be either complementary to the suspected variant nucleotide or to the corresponding normal nucleotide such that an extension product of the second primer is synthesised when the second primer anneals to the diagnostic region containing a particular nucleotide, but no such extension product is synthesised when the second primer anneals to the diagnostic region containing no particular nucleotide of the target nucleic acid sequence. The allele specific second primers may differ by the probe-complementary portions so that the hybridisation/dissociation profiles can be distinguished among different alleles.

Alternatively, the first primer and first probe may be linked by a linker (FIG. 16). The linked first primer/probe may be arranged as, in 5' to 3' order, first probe-linker-first primer, wherein the first probe part may be referred to as 5' tail portion of the first primer. The linker may be natural nucleotides or any other chemical moiety. The linker may contain blocking moiety. If the blocking moiety is present, the replication of the first probe part is blocked. The blocking moiety may be hydrocarbon arm, an HEG, non-nucleotide linkage, a basic ribose, nucleotide derivatives or a dye.

In some embodiments of the invention, the set of multiple second primers used in amplification may be nested primers. Nested primers for use in the amplification are oligonucleotides having sequence complementary to a region on a target sequence between priming sites of the outside primer pair.

The first probe may be attached with first label. When the first probe hybridise to the extended part of the first primer extension product, the hybridisation/dissociation of the first probe generate detectable signal and/or distinct melting profile. More preferably, the 3' priming portion of the first primer may be attached with second label. The first label and second label are interactive label pair. When the first probe hybridises to the extended part of the first primer extension product, the hybridisation bring two labels in close proximity, whereby the melting profile of the first probe is indicative of presence or amount of target nucleic acid in a sample (FIGS. 15 and 16).

Upon hybridisation of labelled primer/probe to the first primer extension product, the two labels are in fluorescence resonance energy transfer relationship (FRET) or contact quenching relationship. The label on the primer (or probe) can be located anywhere as long as it interacts with the label on the other probe (or primer).

A method for assaying a sample for a target nucleic acid or multiple target nucleic acids in a nucleic acid population, said method comprising:
(a) providing template nucleic acids which are derived from target nucleic acids in a nucleic acid population, wherein said template nucleic acids are capable of hybridising with first primers;
(b) treating the template nucleic acids with a first primer or multiple first primers, wherein each first primer anneals to its nucleic acid template under hybridisation conditions, wherein each first primer comprise a 3' priming portion substantially complementary to the first region of the template nucleic acid and 5' tail portion capable of hybridising to an extended part of an extension product of the first primer,
  alternatively, treating the template nucleic acids with a first primer or multiple first primers, and first probe(s), wherein each first primer anneals to its nucleic acid template under hybridisation conditions, wherein each first primer comprise a 3' priming portion substantially complementary to the first region of the template nucleic acid, wherein the first probe is capable of hybridising to an extended part of the first primer extension product adjacent to the first primer;
(c) maintaining the mixture of step (a) under extension conditions, which comprise appropriate nucleoside triphosphates and a nucleic acid polymerase to extend the annealed first primers to synthesize extension products of the first primers;
(d) separating the extension products from the templates; and
(e) maintaining the mixture of step (c) under appropriate conditions, which comprises buffer and an appropriate temperature or a range of temperatures, wherein the first probe or the 5' tail portion of the first primer hybridise to or dissociate from the extended part of the first primer extension product, wherein the process of hybridisation and/or dissociation of the 5' tail portion or the first probe generate detectable signal or distinct melting profile.

The method may further comprise repeating steps (a) and (e) in an amplification method. Any amplification system can be used to include these steps, such as PCR, SDA, LAMP, 3SR and the like. PCR is a preferred amplification method to incorporate these steps.

In the method described herein, a sample is provided which is suspected to contain the target nucleic acid or the nucleotide variant of interest. The target nucleic acid contained in the sample may be double-stranded genomic DNA or cDNA if necessary, which is then denatured, using any suitable denaturing method including physical, chemical, or enzymatic means that are known to those of skill in the art. A preferred physical means for strand separation involves heating the nucleic acid until it is completely (>99%) denatured. Typical heat denaturation involves temperatures ranging from about 80° C. to about 105° C., for times ranging from a few seconds to minutes. As an alternative to denaturation, the target nucleic acid may exist in a single-stranded form in the sample, such as single-stranded RNA or DNA viruses.

The denatured nucleic acid strands are then incubated with oligonucleotide primers under hybridisation conditions; conditions that enable the binding of the primers to the single nucleic acid strands. In one embodiment, the template nucleic acid is provided as the denatured target nucleic acids which are capable of hybridising with first primers. In this embodiment, the first primers are target specific primers, wherein each first primer in a set of multiple primers comprises a 3' priming portion capable of hybridising each target specifically and priming extension. In one instance, each first primer comprises a 5' tail portion capable of hybridising to an extended part of the extension product of the first primer. In another instance, the first primer does not comprise a 5' tail portion, but the reaction comprises a first probe which is capable of hybridising to an extended part of the first primer extension product adjacent to the first primer.

The annealed first primers are extended by a polymerizing agent. Template-dependent extension of the oligonucleotide primer(s) is catalyzed by a polymerizing agent in the presence of adequate amounts of the four deoxyribonucleoside triphosphates (dATP, dGTP, dCTP, and dTTP), or analogues of these as discussed above, in a reaction medium comprised of the appropriate salts, metal cations and pH buffering system. Suitable polymerizing agents are enzymes known to catalyze primer- and template-dependent DNA synthesis. The reaction conditions for catalyzing DNA synthesis with these DNA polymerases are well known in the art.

Separating the extension products from the templates can be carried out by heating. For example, extension products can be separated by heating at 95° C. Alternatively, extension products can be separated from their respective template by strand displacement.

After the first extension product is separated from templates, the reaction mixture is maintained under appropriate conditions, which comprises buffer and an appropriate temperature or a range of temperatures, wherein the first probe or the 5' tail portion of the first primer hybridise to or dissociate from the extended part of the first primer extension product, wherein the process of hybridisation and/or dissociation of the first probe or the 5' tail portion generate detectable signal or distinct profile.

Measuring Tm or monitoring melting curve profile of amplicon or probe duplex are known in the art. In this invention, the detection of multiple targets can be achieved through using label pair and hybridisation/dissociation profile analysis of the first probe hybridising to the extended part of the first primer extension product.

In another embodiment, the first primer is a universal primer; the first probe is a universal probe. Multiple targets can be detected via melting profile analysis of a universal first probe hybridised with multiple different targets through a single fluorescence detection channel.

In this embodiment, the step (a) providing template nucleic acids comprises: i) treating the nucleic acid population with second primers, which are a set of target specific primers, under hybridisation conditions, wherein each second primer anneals to its target nucleic acid, wherein a second primer comprise, in 3' to 5' order, a 3' target specific portion substantially complementary to a region of the target nucleic acid; a tail-probe complementary portion capable of hybridising to the first probe or the 5' tail sequence of the first primer, and 5' universal portion comprising sequence identical or substantially identical to the 3' priming portion of the first primer; ii) maintaining the above mixture under extension conditions, which comprise appropriate nucleoside triphosphates and a nucleic acid polymerase to extend the annealed second primers to synthesize extension products; iii) separating the extension products from the templates; iv) annealing another amplification primer (third primer) or a set of third amplification primers to the single-stranded extension products above and extending the annealed third primers; and v) separating the double-stranded extension products to single-stranded form which includes template nucleic acids, whereby the single-stranded template nucleic acids are capable of hybridising to the first primer (FIG. 15).

The third primer may be one of the amplification primers. The amplification primers are selected so that their relative positions along a duplex sequence are such that an extension product synthesized from the one amplification primer, when the extension product is separated from its template (complement), serves as a template for the extension of the another amplification primer.

The universal first primer may be present in the reaction at a concentration of least 3 times more than the concentration of the second primers. Preferably, the first primer may be present in the reaction at a concentration of at least 6 times more than the concentration of the second primers.

EXAMPLES

Figure 1:
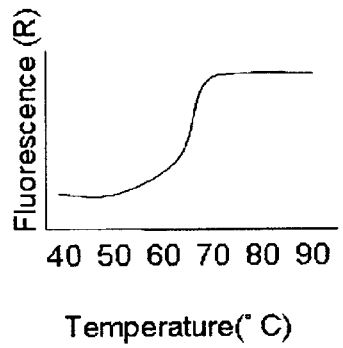
FIG. 1 graphically presents the melting profile of a nucleic acid probe of the present invention before amplification and after amplification in which the probe is consumed.
Figure 1:
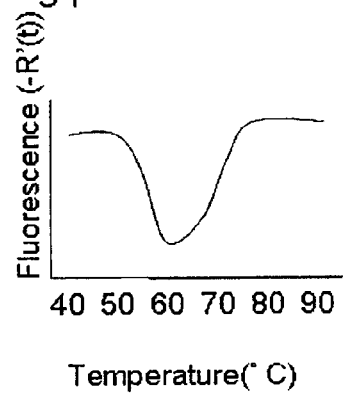
Figure 1:
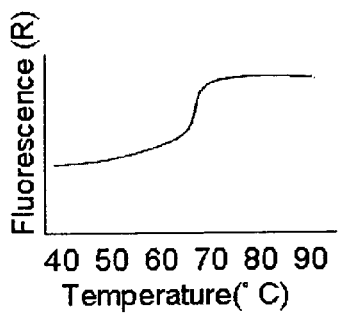
Figure 1:
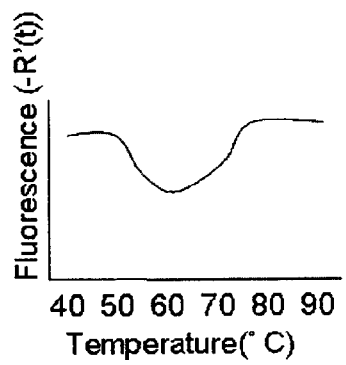
Figure 2:
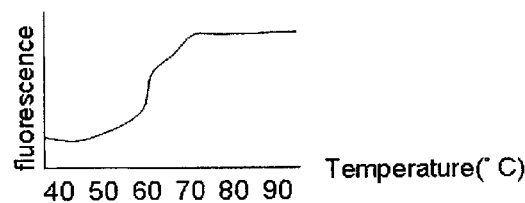
FIG. 2 graphically presents a melting profile of a mixture of nucleic acid probes (probe 1 and 2) of the present invention before amplification and after amplification in which one or both of the probes are consumed.
Figure 2:
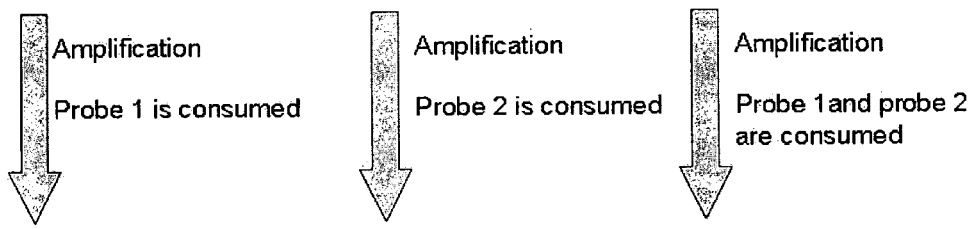
Figure 2:
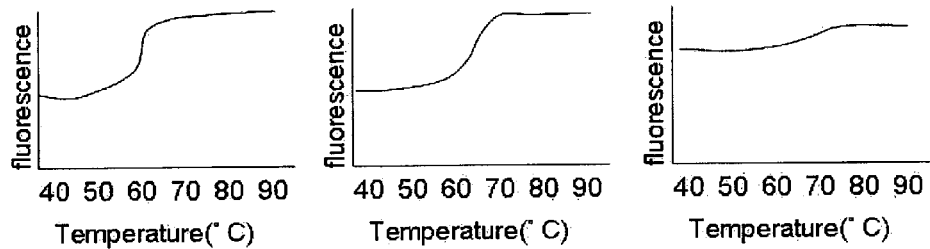
Figure 3:
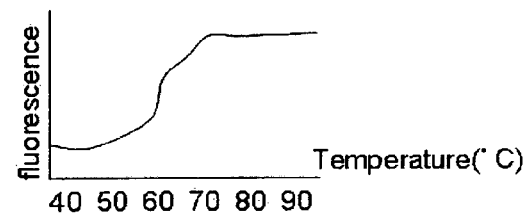
FIG. 3 graphically presents a real-time measurement of an amplicon synthesis at different temperatures.
Figure 3:
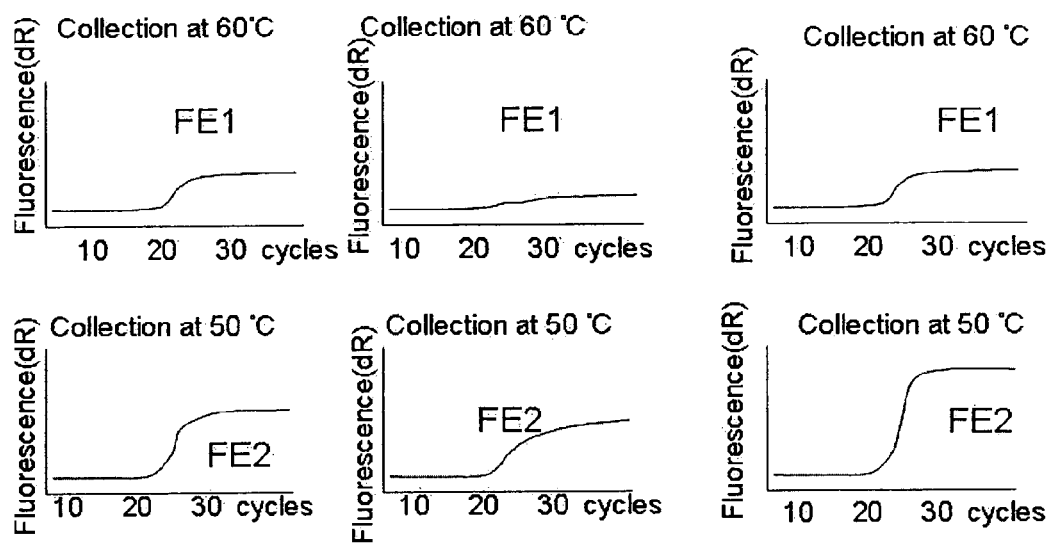
Figure 4:
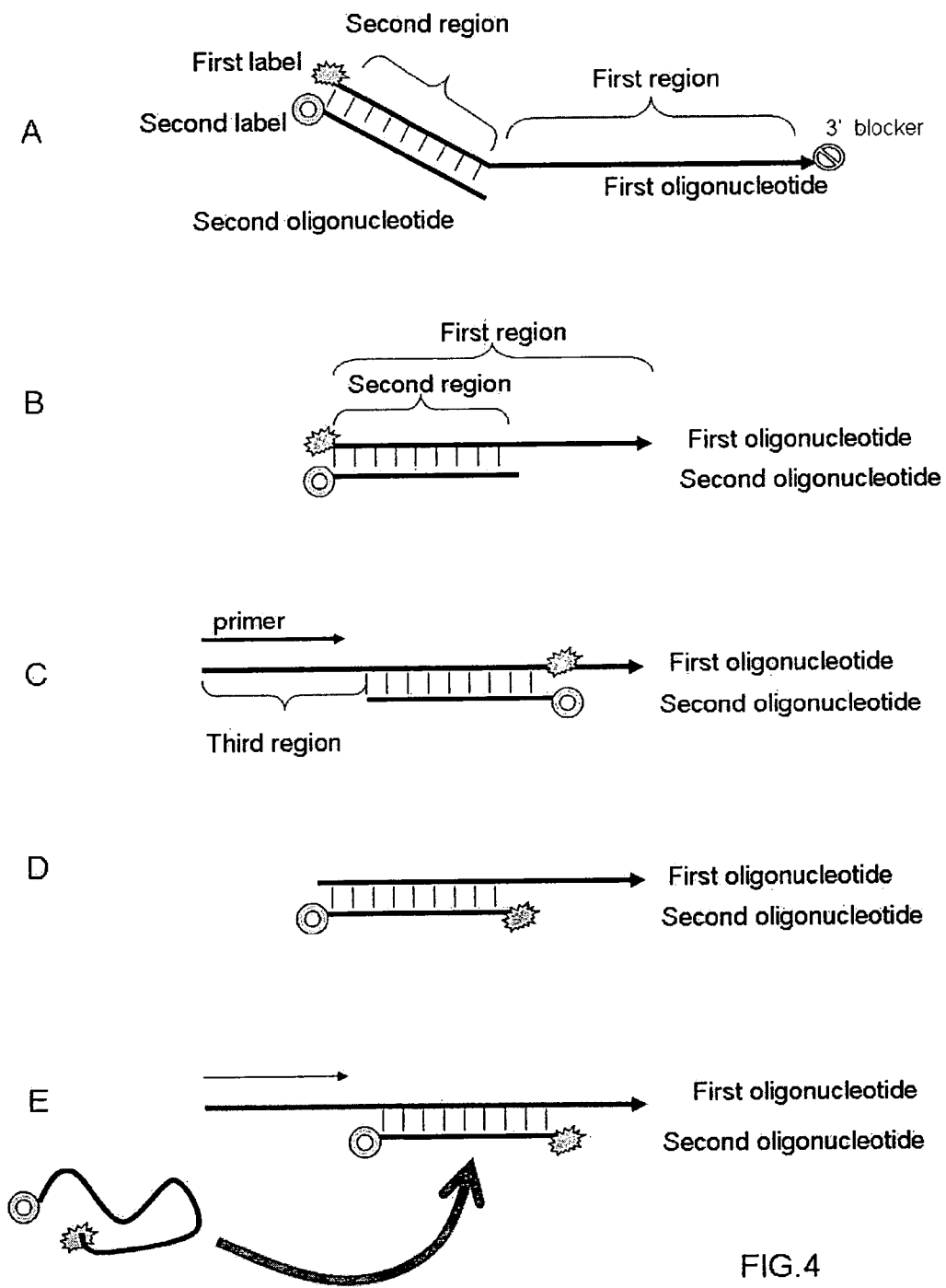
FIG. 4 illustrates examples of different probes which may be used in the present invention.
Figure 4:
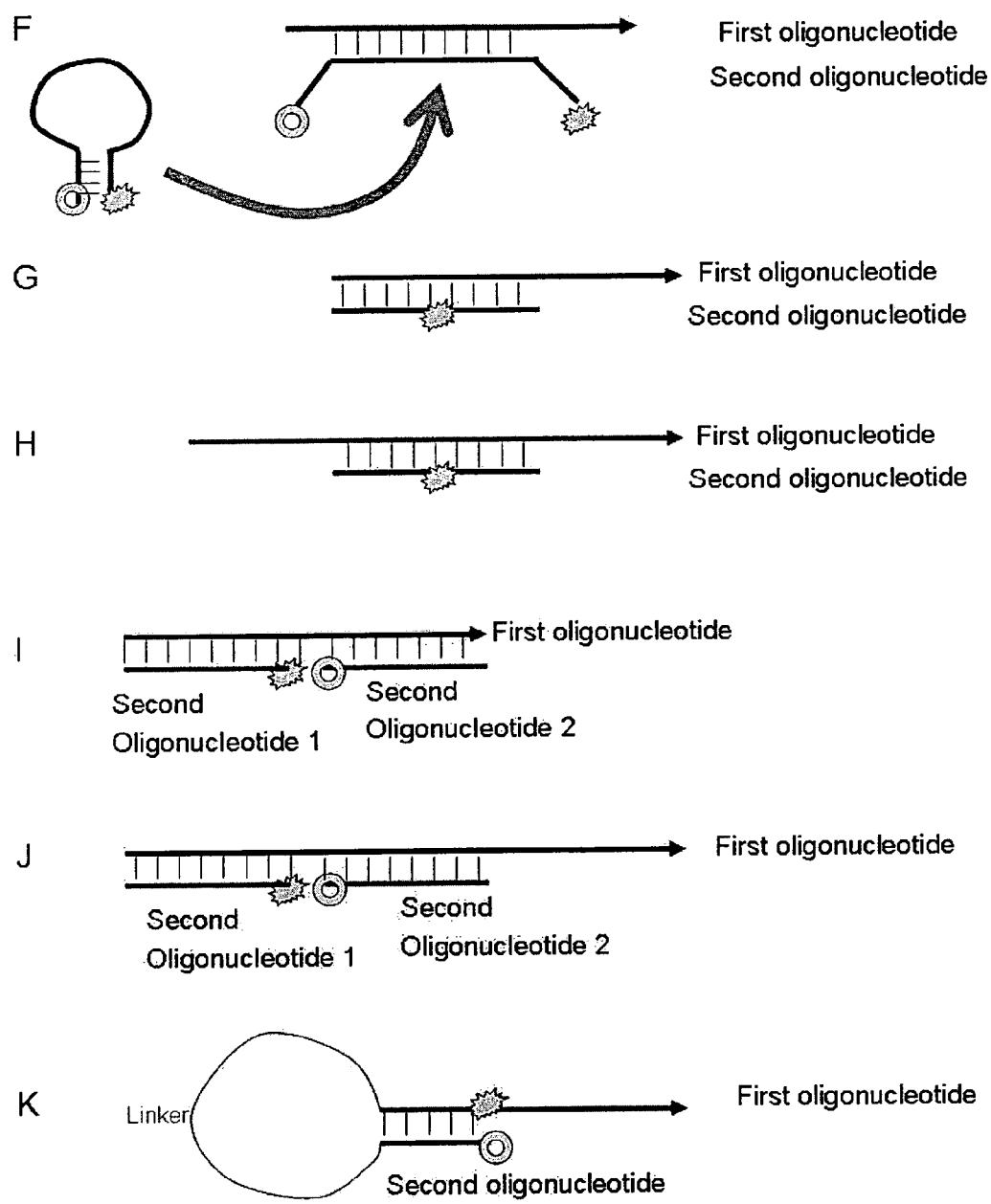
Figure 5:
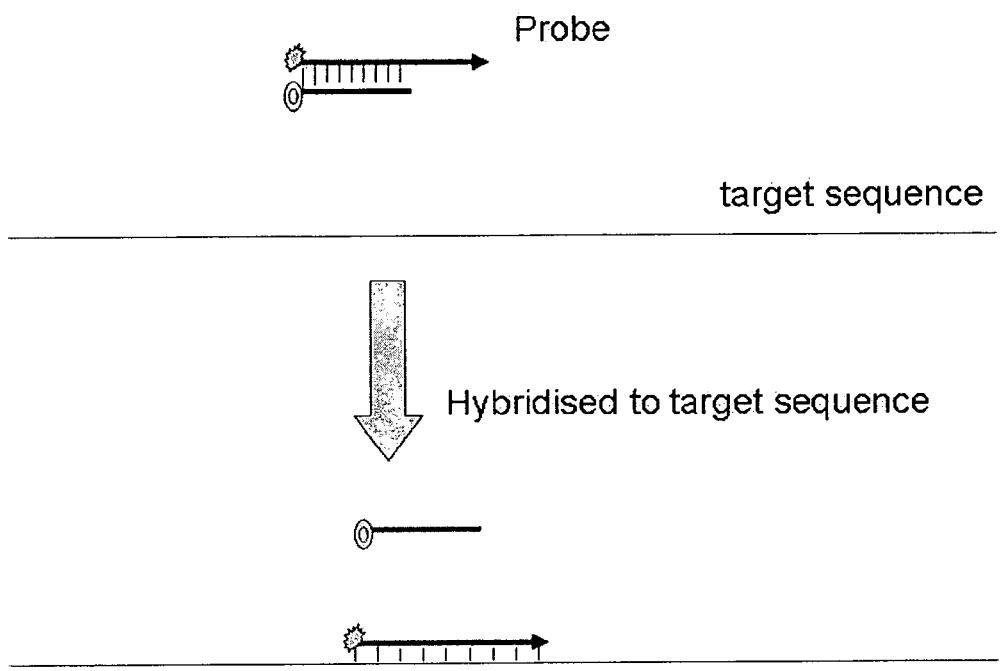
FIG. 5 illustrates an example of a method of the present invention, where the first oligonucleotide of the probe is hybridised with a target nucleic acid sequence.
Figure 6:
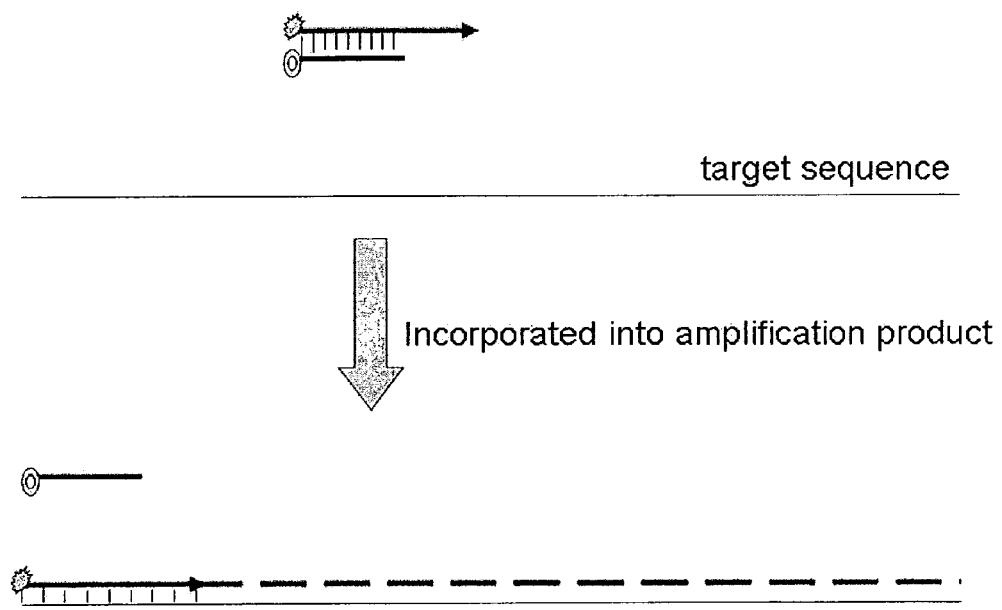
FIG. 6 illustrates an example of a method of the present invention, where the first oligonucleotide of the probe is incorporated into the amplified product.
Figure 7:
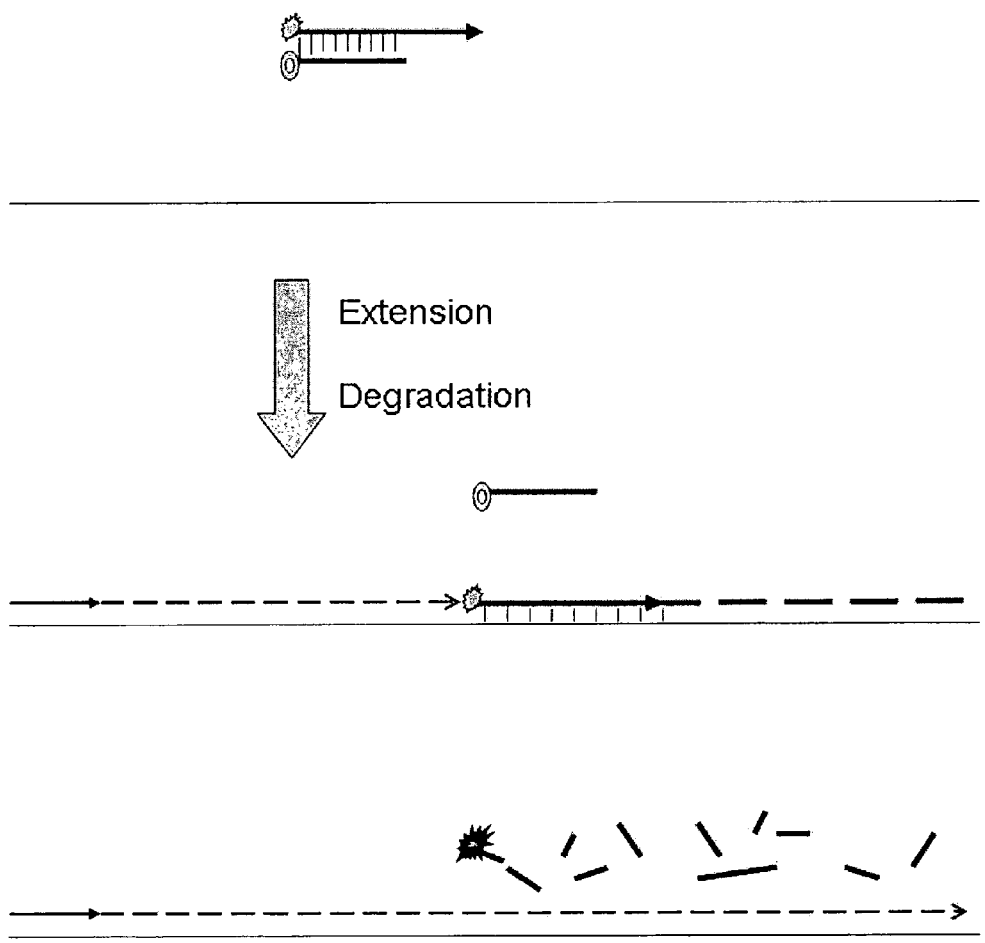
FIG. 7 illustrates an example of a method of the present invention, where the first oligonucleotide of the probe is extended and degraded during the amplification.
Figure 8:
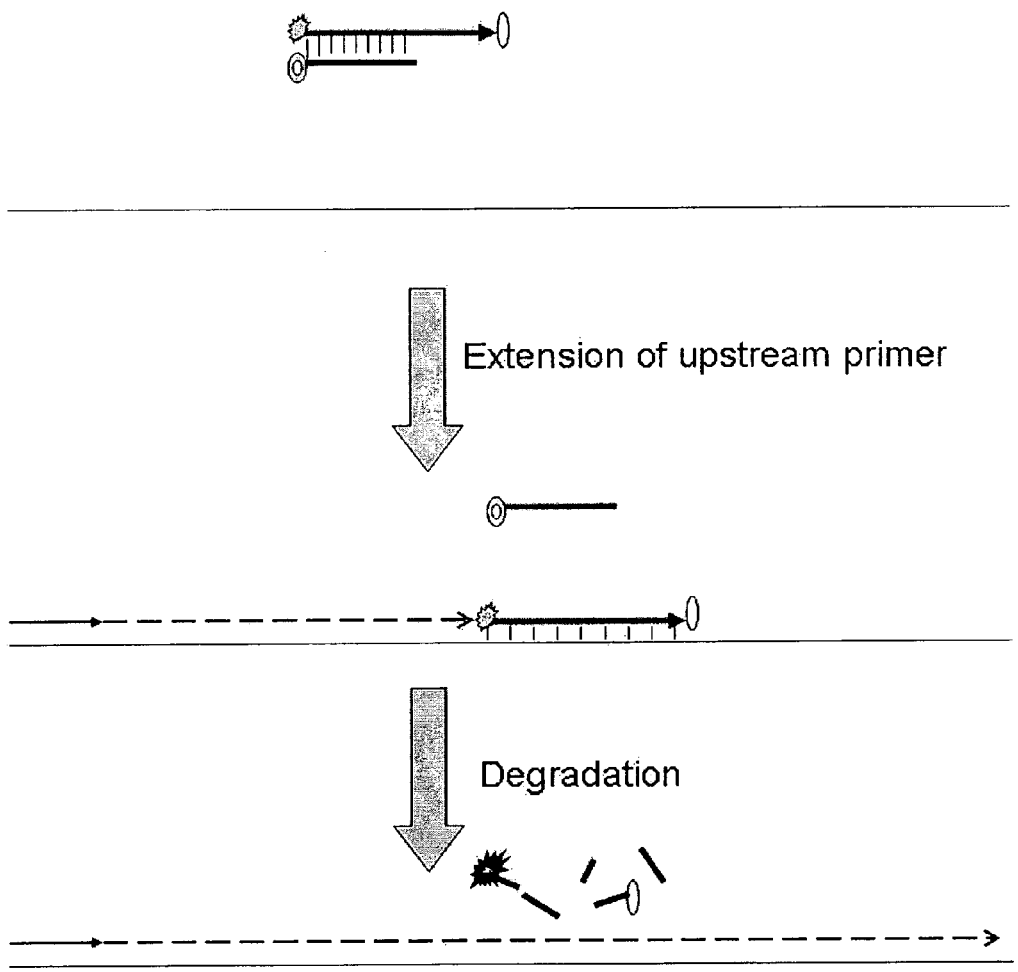
FIG. 8 illustrates an example of a method of the present invention, where the first oligonucleotide of the probe is degraded during the amplification.

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

All primers used in the subsequent experiments were synthesized by EUROGENTEC. Amplification primers and probe are:

```
K10R266Fam
                                                 (SEQ ID NO: 1)
GttcaATTGGGTTTCACCGCGCTTAGTTACA;

K10R266Dab
                                                 (SEQ ID NO: 2)
GCGCGGTGAAACCCAATTGAAC;

SV40R1F3FAM
                                                 (SEQ ID NO: 3)
ATCAGCCATACCACATTTGTAGAGGTTTTAC;

SV40R1F3Dab
                                                 (SEQ ID NO: 4)
CAAATGTGGTATGGCTGAT;

K10F155
                                                 (SEQ ID NO: 5)
CTCTGCTGACTTCAAAACGAGAAGAG;

SV40RealR
                                                 (SEQ ID NO: 6)
CCATTATAAGCTGCAATAAACAAGTTAACAAC
```

Primer/probe K10R266Fam (the first oligonucleotide) is labelled at the 5' end with FAM. K10R266Dab (the second oligonucleotide) contains DABCYL at the 3' end. K10R266Fam and K10R266Dab can form double-stranded portion as:

```
Fam-
                                                 (SEQ ID NO: 1)
5'GTTCAATTGGGTTTCACCGCGCTTAGTTACA3'

DABCYL-
                                                 (SEQ ID NO: 2)
3'CAAGTTAACCCAAAGTGGCGCG5'
```

The above hybrid is referred to as probe K10R266. Primer/probe SV40R1F3FAM (the first oligonucleotide) is labelled at the 5' end with FAM. SV40R1F3Dab (the second oligonucleotide) contains DABCYL at the 3' end. SV40R1F3FAM and SV40R1F3Dab can form double-stranded portion as:

```
Fam-
                                                 (SEQ ID NO: 3)
5'ATCAGCCATACCACATTTGTAGAGGTTTTAC3'

DABCYL-
                                                 (SEQ ID NO: 4)
3'TAGTCGGTATGGTGTAAAC5'
```

This hybrid is referred to as probe SV40R1F3.

The first oligonucleotide and the second oligonucleotide were combined at various ratios, typically 1:3 to form a partially double-stranded linear DNA probe. In the absence of target, the formation of the first and the second oligonucleotide hybrid brings the quencher and the fluorophore into close proximity, efficiently quenching the fluorescent signal. In the presence of the target, the first oligonucleotide preferentially hybridises to the target sequence and incorporates into the amplicon. As a result, the quencher is separated from the fluorophore resulting in an increase in fluorescence emission.

Primer pair K10R266Fam and K10F155 amplifies a 110 bp product in the presence of a K10 target sequence. SV40R1F3FAM and SV40RealR amplifies a 125 bp product in the presence of an SV40 target sequence.

Example 2

Melting profile experiments were performed as follows: The thermal stability of the probes was characterized in melting profile experiments where fluorescence emission was measured at temperatures ranging from 40 to 90° C. Melting temperature $T_m$ is defined as the characteristic temperature where the first and the second oligonucleotide duplex dissociate.

Each melting profile was measured in a tube in a 20 μl reaction containing PCR buffer (1× ThermoPol reaction buffer, New England BioLabs). Thermal cycling was performed in an Mx3005p quantitative PCR system (Stratagene) with the following cycling conditions: 1 cycle of denaturation at 90° C. for 3 min; 50 cycles of 30 second holding at a range of temperatures from 40 to 90° C. with a 1° C. increment per cycle. Fluorescence measurements were recorded during each 30 second hold of the 50 cycles.

Figure 9:
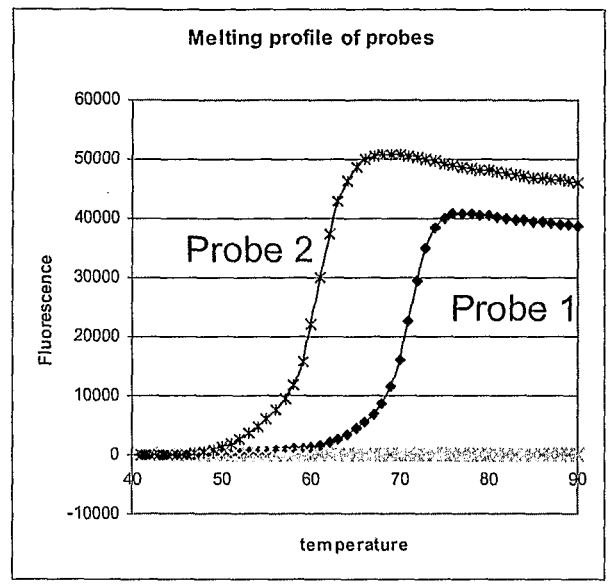
FIG. 9A graphically presents a melting profile of probe 1 and 2 of the present invention before amplification.
FIG. 9B presents a melting profile of a mixture of probes 1 and 2 at different ratios.
Figure 9:
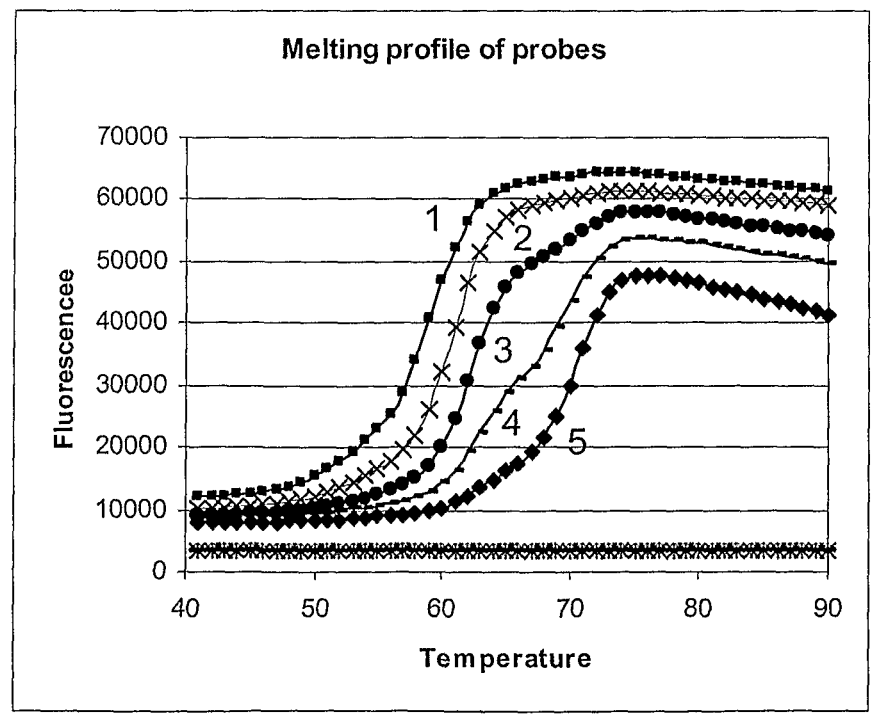

Melting profiles were determined for probe K10R266 (probe 1) and probe SV40R1F3 (probe 2) by monitoring fluorescence at temperatures ranging from 90 to 40° C. K10R266 has a $T_m$ of 72° C.; SV40R1F3 has a $T_m$ of 62° C. (FIG. 9A).

Melting profiles were determined for a series of mixtures of probe K10R266 and probe SV40R1F3:

Sample 1 contains 0.5 μM of K10R266 and 0.5 μM of SV40R1F3.

Sample 2 contains 0.5 μM of K10R266 and 0.25 μM of SV40R1F3.

Sample 3 contains 0.5 μM of K10R266 and 0.125 μM of SV40R1F3.

Sample 4 contains 0.5 μM of K10R266 and 0.0625 μM of SV40R1F3.

Sample 5 contains 0.5 μM of K10R266 and 0.003125 μM of SV40R1F3.

The profiles are shown in FIG. 9B.

A combination of probes K10R266 and SV40R1F3 were tested in real-time PCR assays using plasmids DNA containing K10 and SV40 sequence as templates.

A master reaction mixture was made containing 0.5 μM of K10R266 and 0.5 μM of SV40R1F3 (combination of first oligonucleotide and second nucleotide in 1:3 ratio mix) and standard PCR ingredients (NEB). Amplification reactions were performed in Stratagene Mx3005 real-time PCR system with the following cycling conditions:

1. Before amplification, melting profile: 50 cycles of 30 second holding at a range of temperatures from 90 to 40° C. with a 1° C. decrement per cycle, fluorescence measurements were recorded during each 30 second hold of the 50 cycles.
2. Amplification: 30 cycles of 94° C. 20 s; 63° C. 30 s; 51° C. 30 s; 72° C. 30 s; fluorescence measurements were recoded during the read steps 63° C., 51° C. and 72° C.
3. Post-amplification melting profile: 50 cycles of 30 second holding at a range of temperatures from 40 to 90° C. with a 1° C. increment per cycle, fluorescence measurements were recorded during each 30 second hold of the 50 cycles.

Four reactions were set up: reaction 1 contains K10 template; reaction 2 contains SV40 template; reaction 3 contains both K10 and SV40 templates; reaction 4 contains no template.

Figure 10:
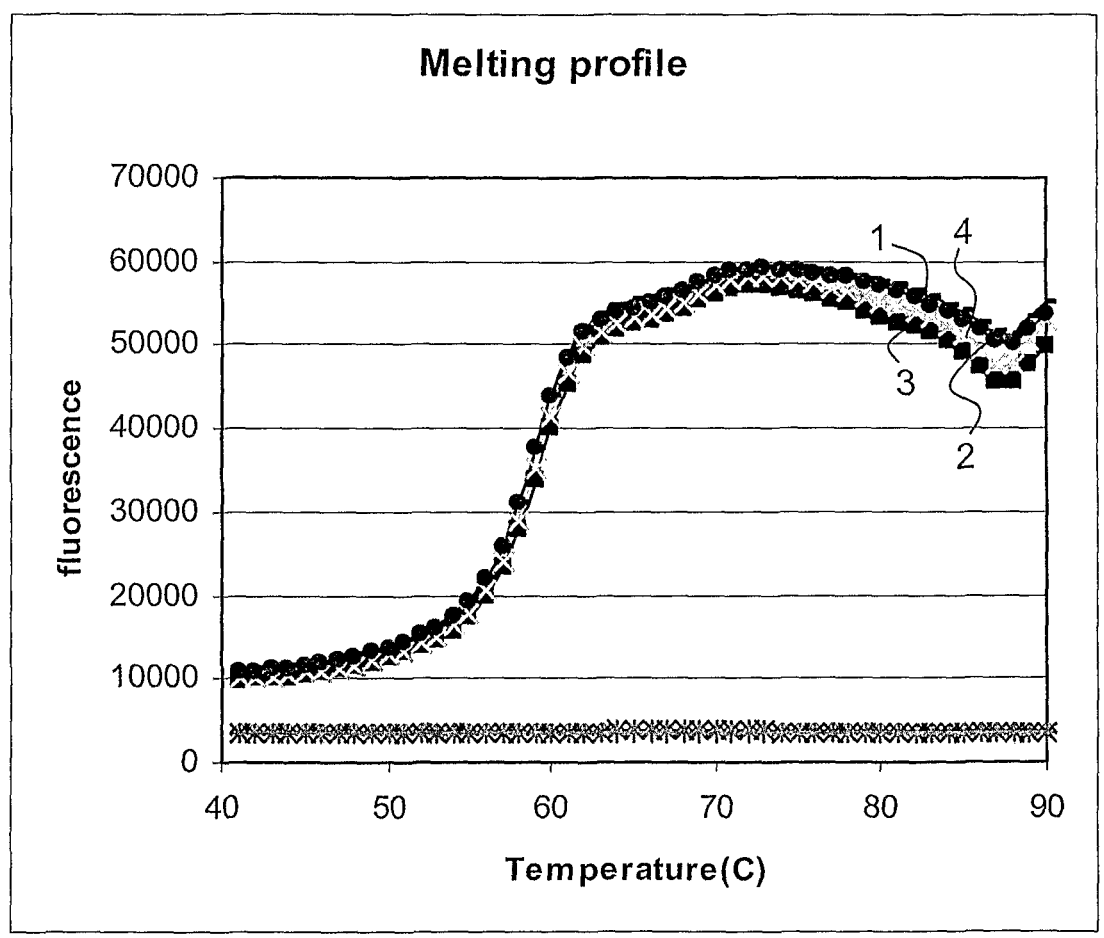
FIG. 10 graphically presents a melting profile of mixture of probes 1 and 2 in the 4 reactions before amplification.

The pre-amplification melting profiles for four reactions are shown in FIG. 10.

Figure 11:
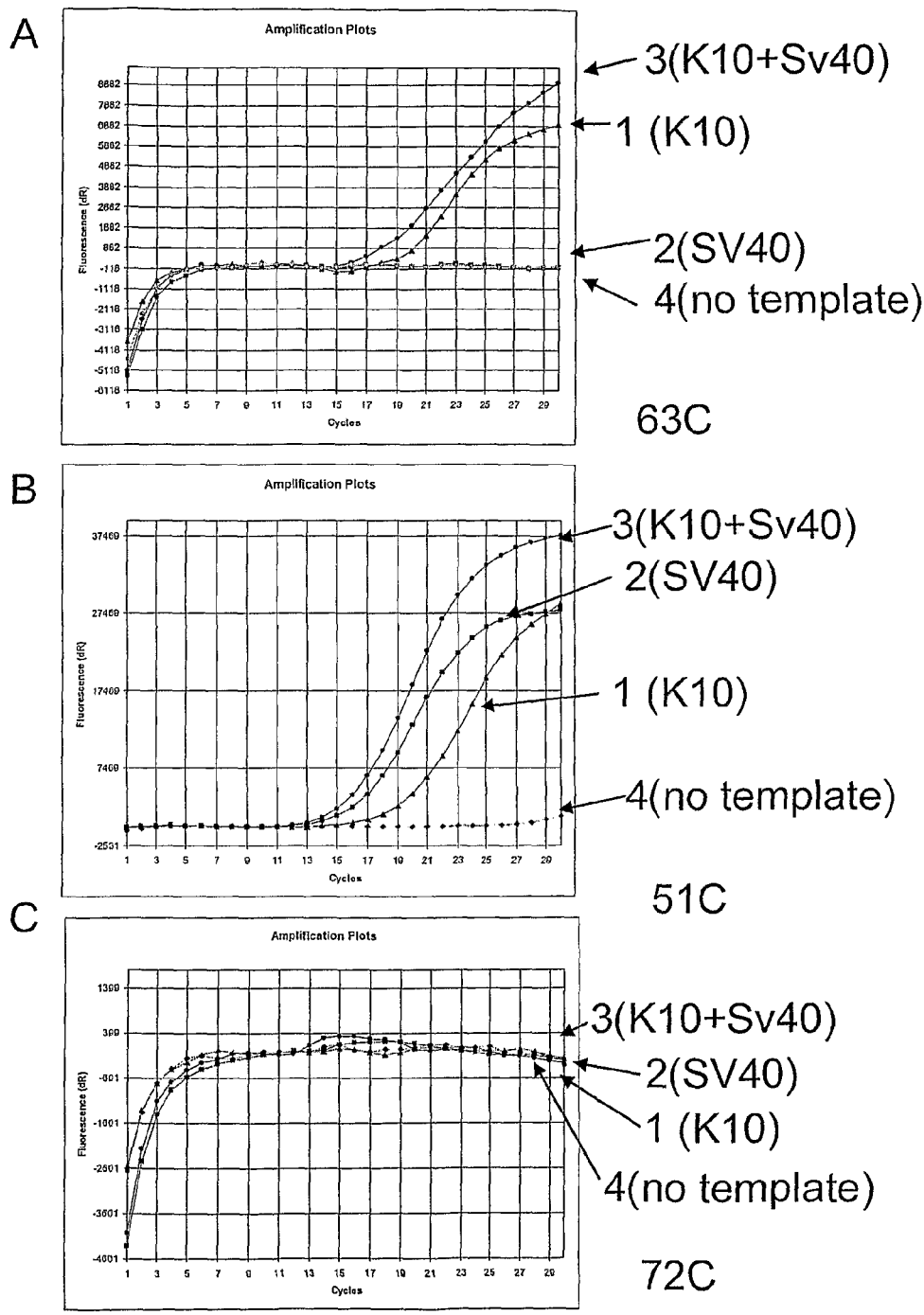
FIG. 11 graphically presents a real-time measurement of amplicon synthesis at different temperatures in the Example.

Fluorescence emission was collected at 63° C. during amplification is shown in FIG. 11A.

Fluorescence emission was collected at 51° C. during amplification is shown in FIG. 11B.

Fluorescence emission was collected at 72° C. during amplification is shown in FIG. 11C.

Figure 12:
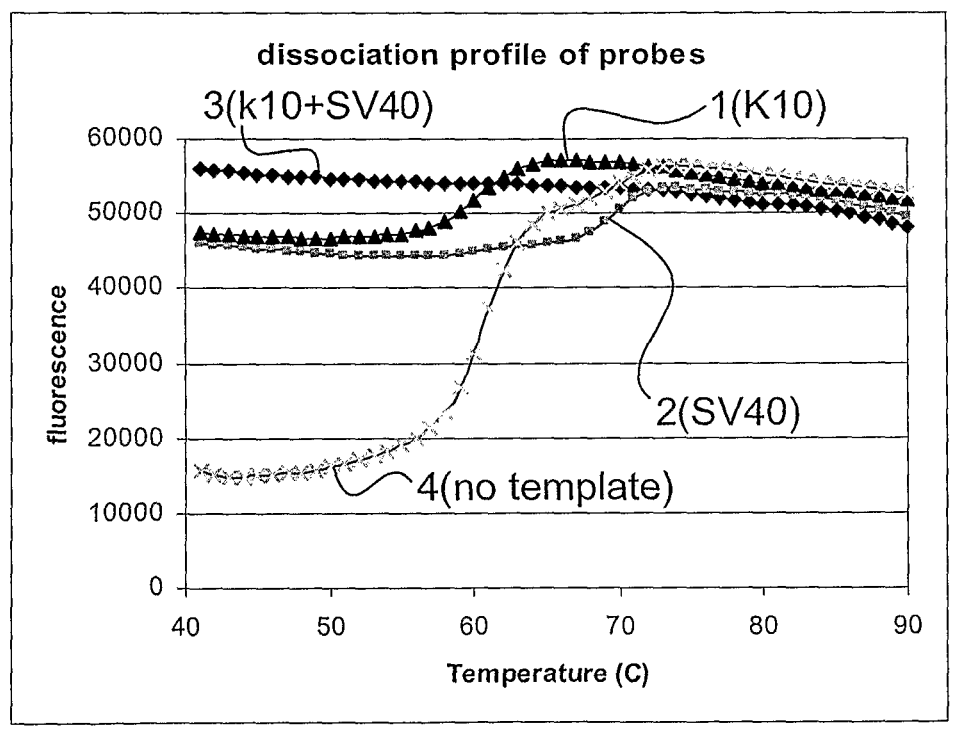
FIG. 12 graphically presents a melting profile of a mixture of probes 1 and 2 in the 4 reactions after amplification.

The post-amplification melting profiles for four reactions are shown in FIG. 12.

Comparison of the pre-amplification and post-amplification melting profiles indicated the following:

In reaction 1 the K10R266 probe is consumed and the profile is the signature of SV40R1F3 probe.

In reaction 2 the SV40R1F3 probe is consumed.

In reaction 3, both K10R266 and SV40R1F3 probes are consumed.

In reaction 4, no probe is consumed and the pre- and post-amplification profiles are similar.

Cycle by cycle fluorescence emissions FE were obtained at three measuring temperatures: MT 72° C., 63° C. and 51° C.

A first fluorescence emission FE1 is obtained at a measuring temperature 63° C., at which no more than 10% of second probe (SV40R1F3) is in duplex form (the internal double-stranded form of the probe); second fluorescence emission FE2 is obtained at a measuring temperature 51° C., at which more than 95% of two probes are in duplex form, and optionally a fluorescence emission FE0 is obtained at a measuring temperature 72° C., at which no more than 10% of first probe (K10R266) is in duplex form.

In the amplification reactions there are two probes for two target sequences K10 and SV40. At temperature 72° C., 10% of the K10R266 probe is in duplex form, 0% of the SV40R1F3 probe is in duplex form. At 63° C., 90% of the K10R266 probe is in duplex form, 5% of SV40R1F3 probe is in duplex form. At 51° C., more than 98% of all probes are in duplex form.

The first fluorescence emission is collected at 63° C., which is FE1; the second fluorescence emission is collected at 51° C., which is FE2.

|  | Probe1(K10) | | Probe2(SV40) | | fluorescence |
|---|---|---|---|---|---|
|  | ds % | ACA1 | ds % | ACA2 | emission |
| 72° C. | 10 | 10% ACA1 | 0 | 0% ACA2 |  |
| 63° C. | 90 | 90% ACA1 | 5 | 5% ACA2 | FE1 |
| 51° C. | 98 | 98% ACA1 | 98 | 98% ACA2 | FE2 |

FE1 = 90%*ACA1 + 5%*ACA2
FE2 = 98%*ACA1 + 98%*ACA2

Assuming 5%*ACA2 is neglectable, ACA1=FE1/90%; ACA2=FE2/98%-FE1/90%. ACA1 is the actual consumed amount of probe 1; ACA2 is the actual consumed amount of probe 2.

Figure 13:
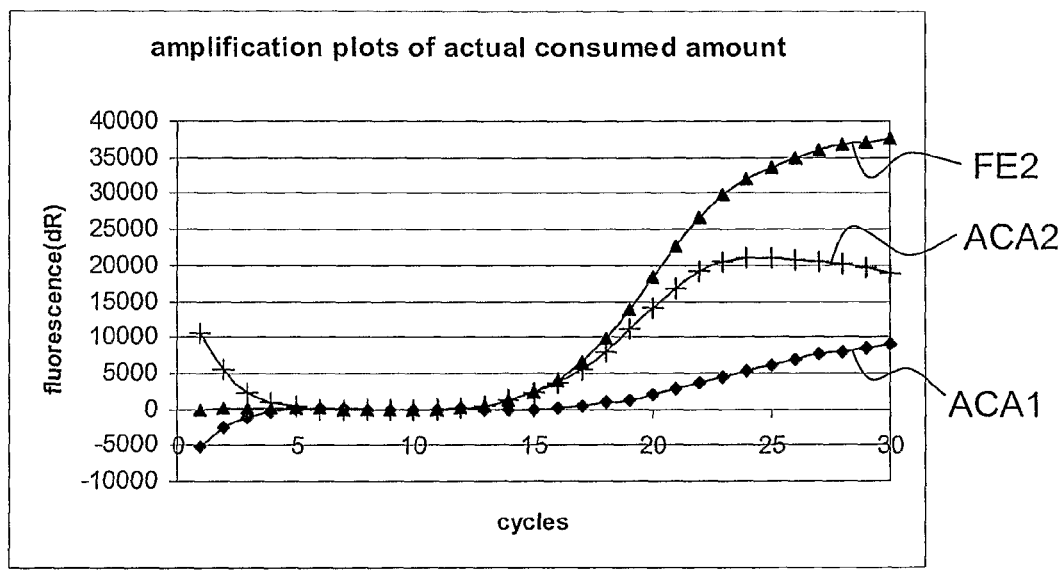
FIG. 13 illustrates the amplification plot where the emission amount of the first probe (K10) is drawn as FE1. The calculated FE1×P plot is drawn as FE1×P. The amplification plot for the emission amount of the second probe (SV40) is shown as FE2−(FE1×P).
Figure 14:
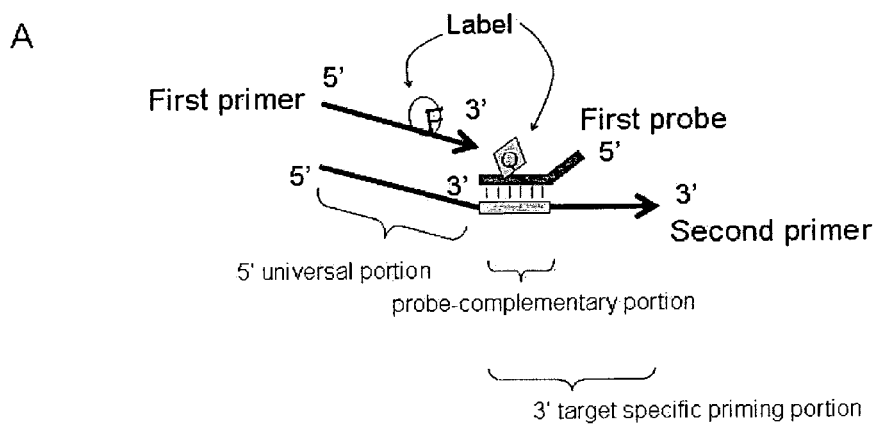
FIG. 14 illustrates a combination of primers and probes (A) and a set of combinations of primers and probes (B).
Figure 14:
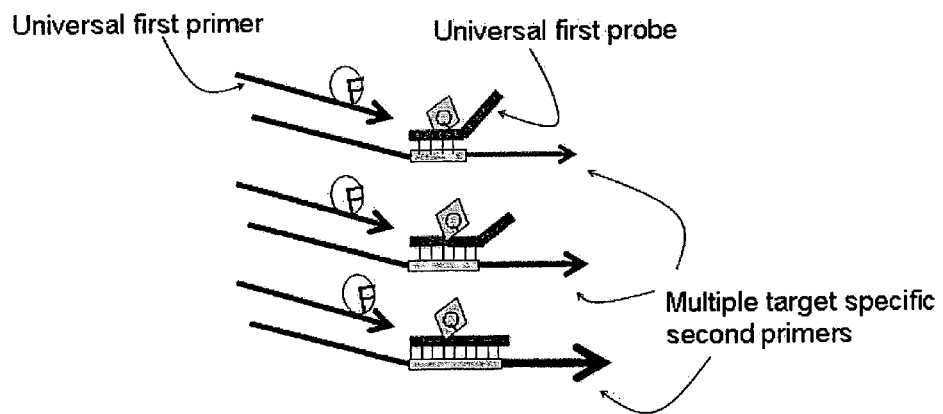
Figure 15:
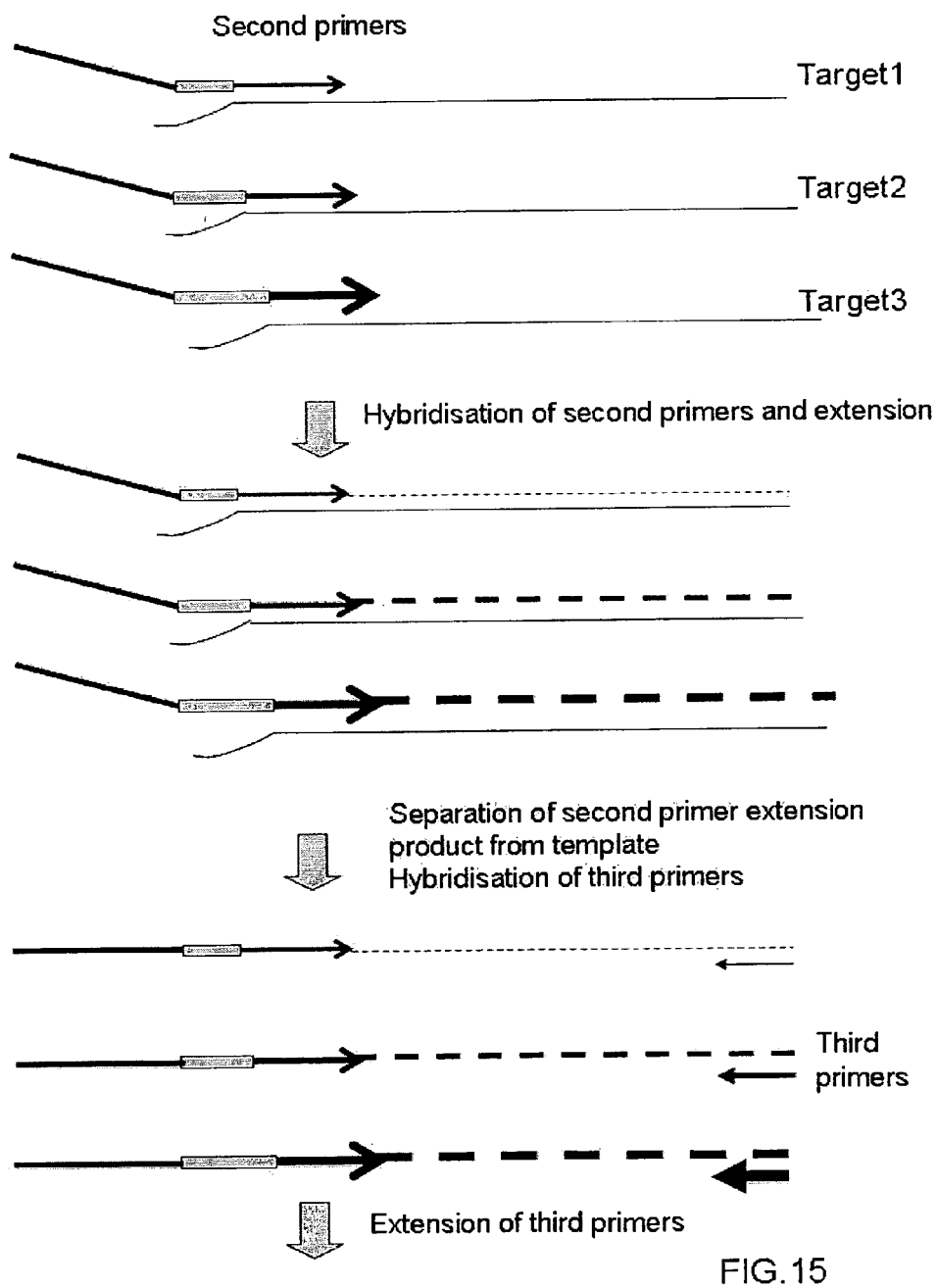
FIG. 15 illustrates a method for detecting and quantifying 3 target nucleic acids using a set of combinations of primers and probes.
Figure 15:
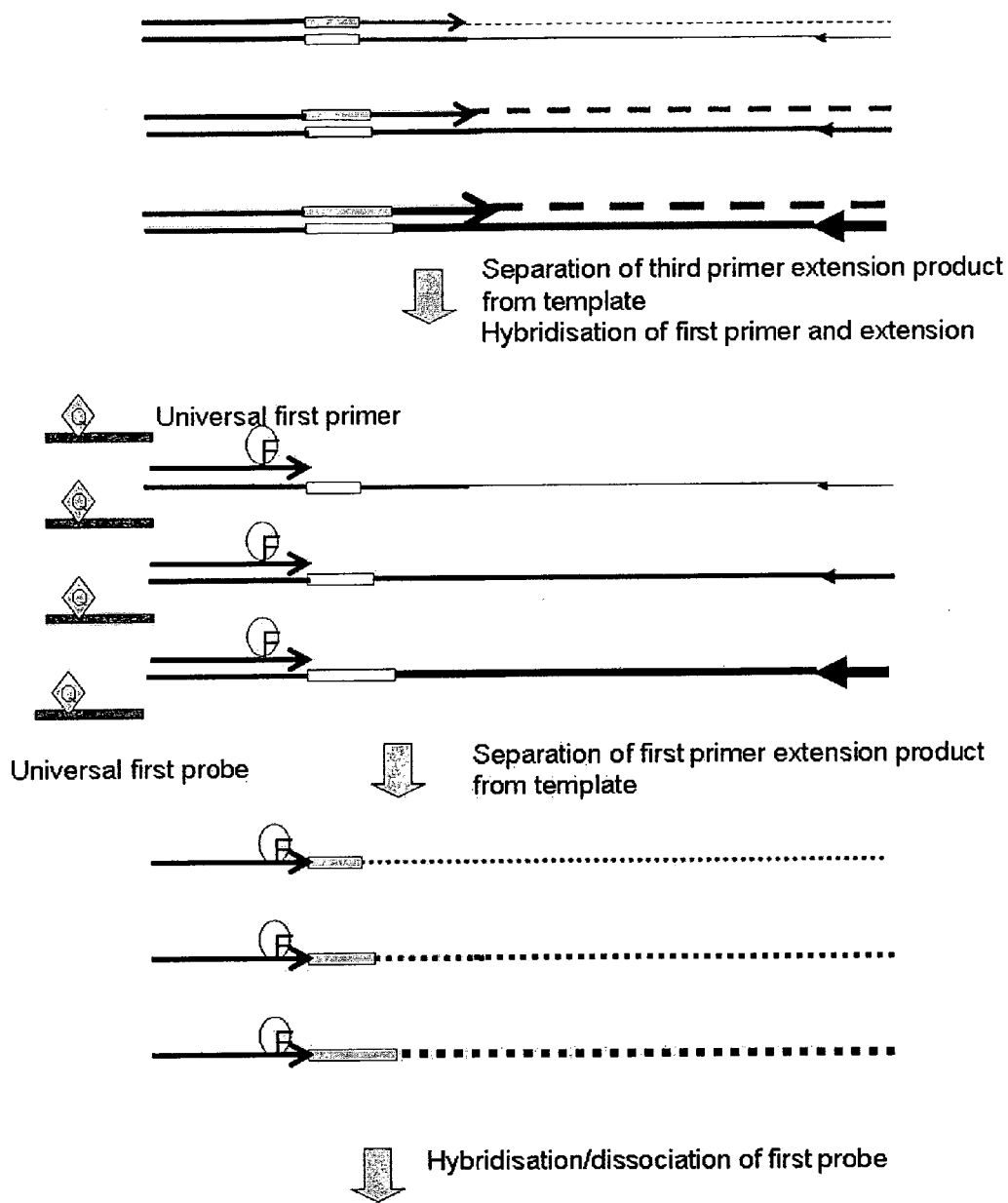
Figure 15:
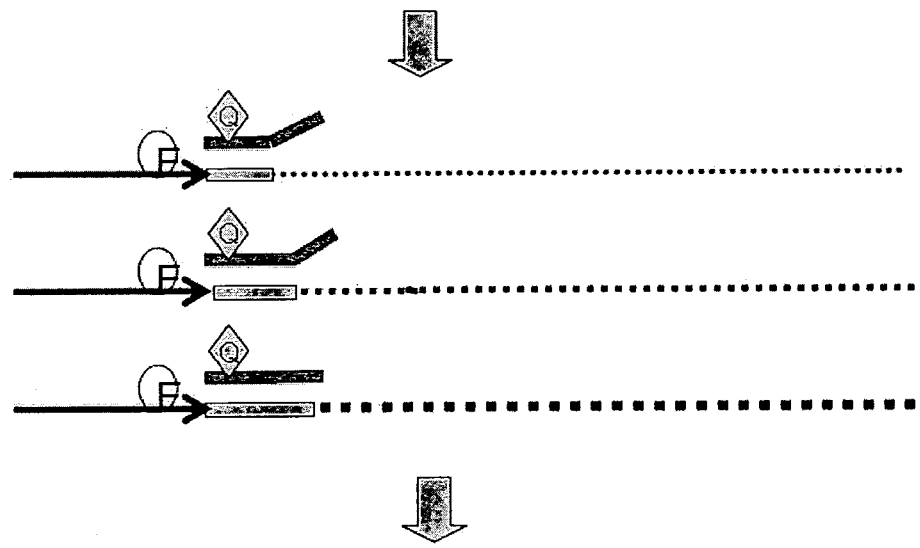
Figure 16:
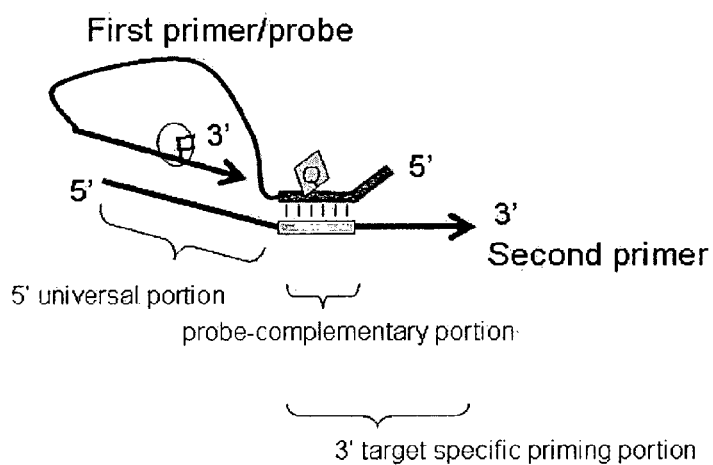
FIG. 16 illustrates a modified form of the combination of primers and probes, wherein the first primer and probe are linked together.
Figure 16:
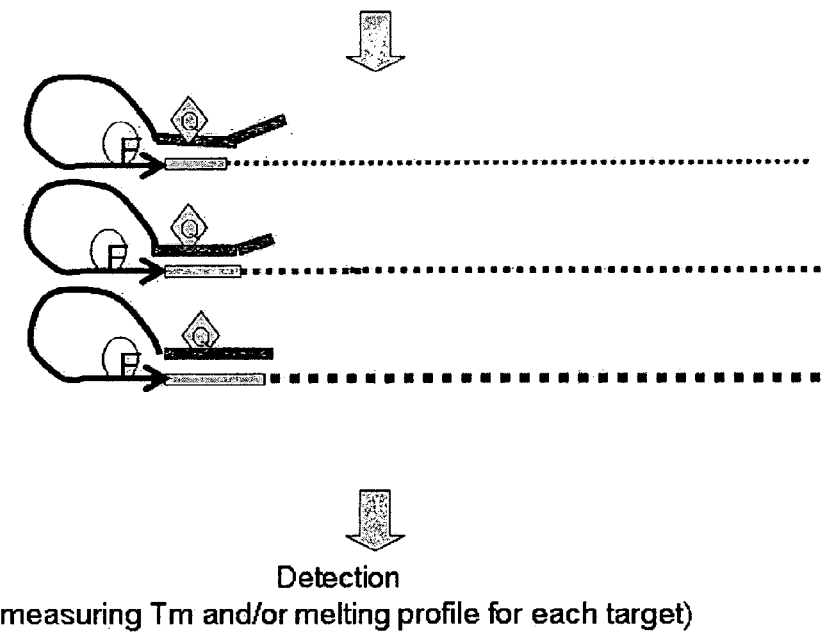
Figure 17:
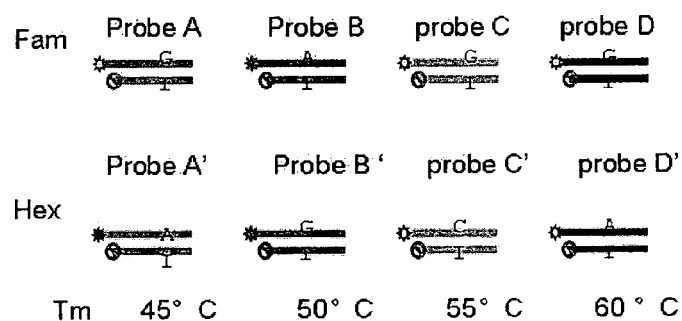
FIG. 17 A set of probes labeled with Fam contain sequences complementary to the wild-type sequence, which have a different Tm; another set of probes labeled with Hex contains sequences complementary to the variant sequence of the same target nucleic acid sequence.
Figure 17:
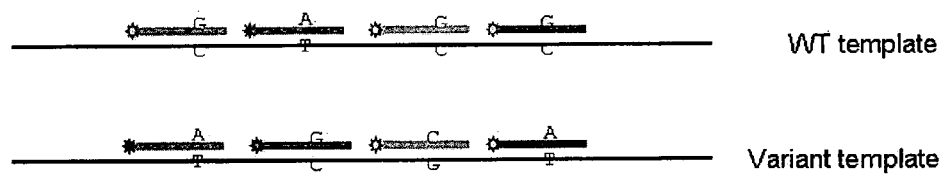
Figure 18:
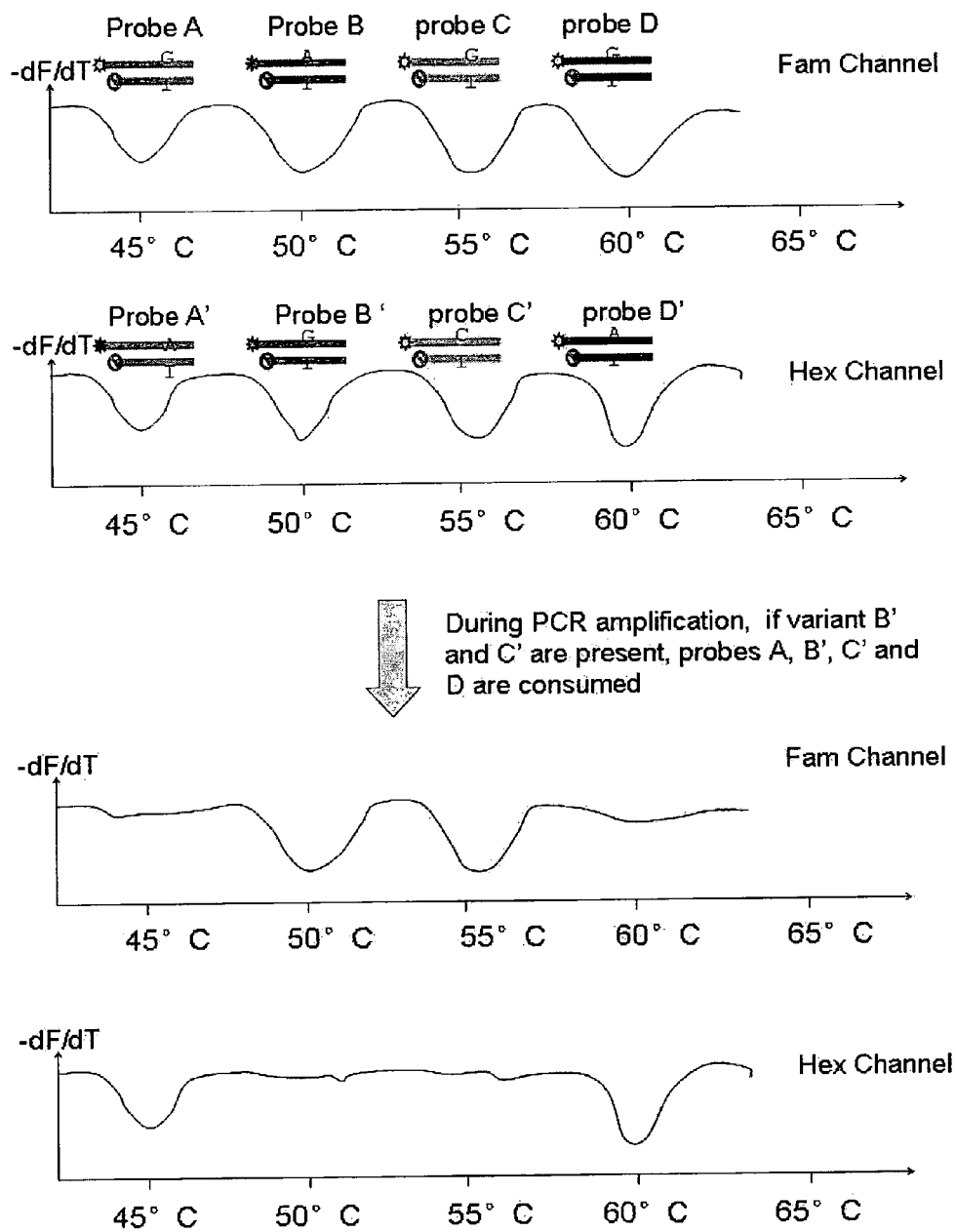
FIG. 18 illustrates a method using the set probes described in FIG. 17.

The amplification plot for the actual consumed amount of the first probe (K10) is drawn as ACA 1. The amplification plot for the actual consumed amount of the second probe (SV40R1F3) is shown as ACA2 (FIG. 13).

The calculation of the actual consumed amount can be performed manually. The calculation can also be performed through a computer program or software. To expedite the quantification, software was designed to manage emission data from the multiplex real-time PCR and perform appropriate calculations. The software had other functions, such as manual selection of the Ct and subtraction of blanks.

The software was implemented in Visual Basic for applications (VBA) as an Addin for Microsoft Excel. The source code was organized in two main modules. One module contained all the "utility" functions such as mathematical functions, functions to generate arrays from emission data present in the Excel sheets, functions to print result data and labels, functions to handle errors or template and functions to generate charts of a certain types. The second module contained the functions to control the flow of the program. This module contained all the functions making possible the interaction with the user, such as menu selections, bar slicing, inclusion/exclusion of data in the standard curve.

Example 3

Amplification Primers and Probe are

```
For target 1 (K10)
K10R266Fam
                                 (SEQ ID NO: 1)
GttcaATTGGGTTTCACCGCGCTTAGTTACA;

K10R266Dab
                                 (SEQ ID NO: 2)
GCGCGGTGAAACCCAATTGAAC;

K10F155
                                 (SEQ ID NO: 5)
CTCTGCTGACTTCAAAACGAGAAGAG;

For target 2 (SV40)
SV40R1F3FAM
                                 (SEQ ID NO: 3)
ATCAGCCATACCACATTTGTAGAGGTTTTAC;

SV40R1F3Dab
                                 (SEQ ID NO: 4)
CAAATGTGGTATGGCTGAT;

SV40RealR
                                 (SEQ ID NO: 6)
CCATTATAAGCTGCAATAAACAAGTTAACAAC;

For target 3 (Jak2)
JKR3Fam
                                 (SEQ ID NO: 11)
AACAGATGCTCTGAGAAAGGCATTAGA;

JKR3FDabF
                                 (SEQ ID NO: 12)
CTCAGAGCATCTGTT;

JKF2
                                 (SEQ ID NO: 13)
GCATCTTTATTATGGCAGAGAGAA.
```

The oligonucleotide K10R266Fam is an amplification primer, in the same time the oligonucleotide K10R266Fam is the first oligonucleotide of the probe 1. K10R266Fam (the first oligonucleotide) is labelled at the 5' end with FAM. K10R266Dab (the second oligonucleotide) contains DABCYL at the 3' end. K10R266Fam and K10R266Dab can form double-stranded portion. The hybrid of K10R266Fam and K10R266Dab is referred to as probe 1.

The oligonucleotide SV40R1F3FAM is an amplification primer, in the same time the oligonucleotide SV40R1F3FAM is the first oligonucleotide of the probe 2. SV40R1F3FAM (the first oligonucleotide) is labelled at the 5' end with FAM. SV40R1F3Dab (the second oligonucleotide) contains DABCYL at the 3' end. SV40R1F3FAM and SV40R1F3Dab can form double-stranded portion. The hybrid of SV40R1F3FAM and SV40R1F3Dab is referred to as probe 2.

The oligonucleotide JKR3Fam is an amplification primer, in the same time the oligonucleotide JKR3Fam is the first oligonucleotide of the probe 3. JKR3Fam (the first oligonucleotide) is labelled at the 5' end with FAM. JKR3FDabF (the second oligonucleotide) contains DABCYL at the 3' end. JKR3Fam and JKR3FDabF can form double-stranded portion. The hybrid of JKR3Fam and JKR3FDabF is referred to as probe 3.

The first oligonucleotide and the second oligonucleotide were combined at various ratios, typically 1:2-1:4 to form a partially double-stranded linear DNA probe. In the absence of target, the formation of the first and the second oligonucleotide hybrid brings the quencher and the fluorophore into close proximity, efficiently quenching the fluorescent signal. In the presence of the target, the first oligonucleotide preferentially hybridises to the target sequence and incorporates into the amplicon. As a result, the quencher is separated from the fluorophore resulting in an increase in fluorescence emission.

Primer pair K10R266Fam and K10F155 amplifies a 110 bp product in the presence of a K10 target sequence. SV40R1F3FAM and SV40RealR amplifies a 125 bp product in the presence of an SV40 target sequence. Primers JKR3Fam and JKF2 amplifies a 222 bp product in the presence of Jak2 target sequence.

Figure 19:
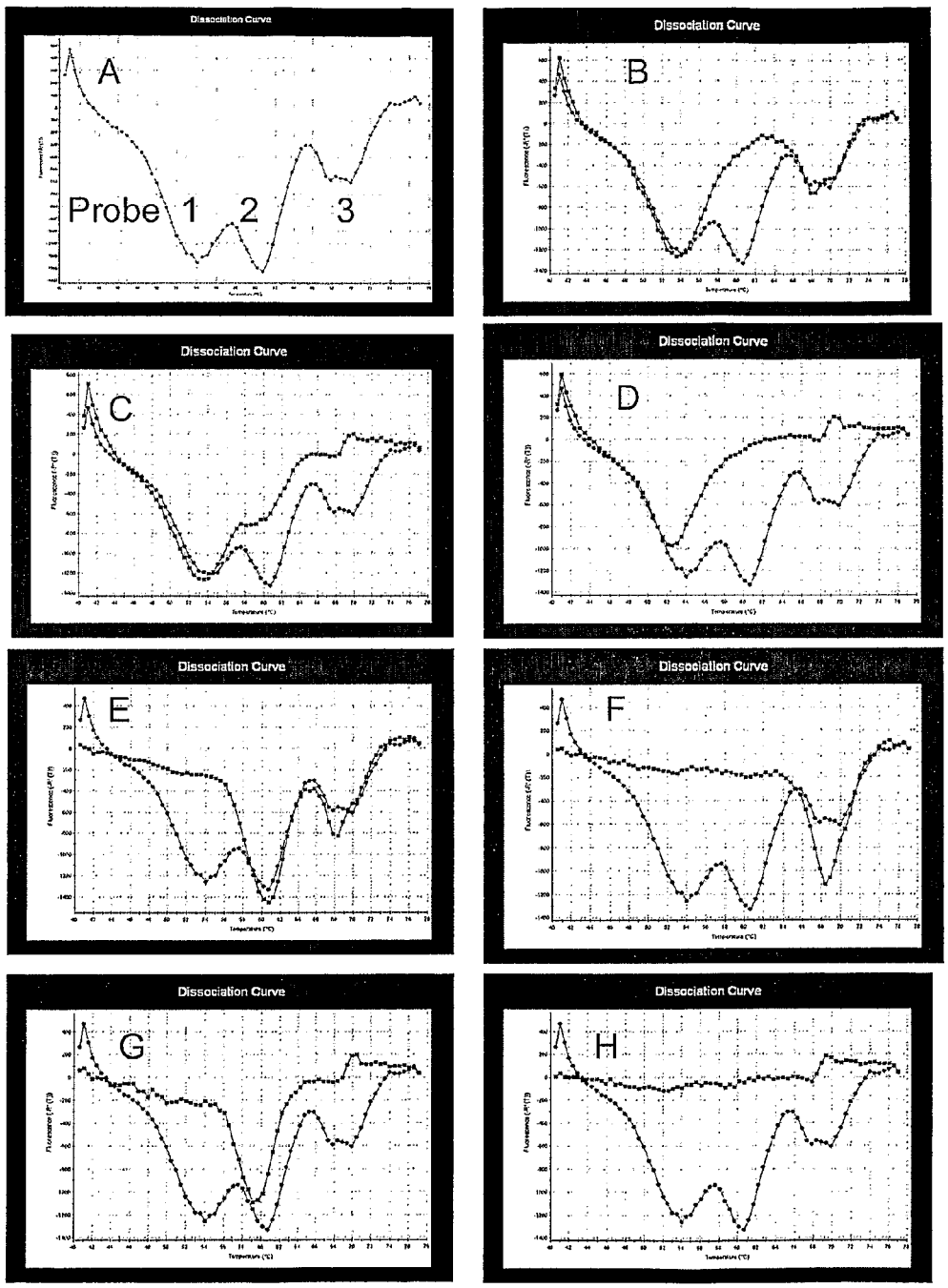
FIG. 19 shows results of an example of triplex amplification. Three probes with different Tms are labeled with Fam dye. (A) shows a melting profile generated in a tube without adding target DNA. The following figures show comparison of melting profile generated in a tube without adding target DNA and melting profile generated in a tube with adding target DNA. (B) melting profiles generated in a tube with target 2 present in the sample. (C) melting profile generated in a tube with target 3 present in the sample. (D) melting profile generated in a tube with targets 2 and 3 present in the sample. (E) melting profile generated in a tube with target 1 present in the sample. (F) melting profile generated in a tube with targets 1 and 2 present in the sample. (G) melting profile generated in a tube with target 1 and 3 present in the sample. (H) melting profile generated in a tube with targets 1, 2 and 3 present in the sample.

Melting profile analysis of probe 1, probe 2, probe 3 and mixed probe 1, 2 and 3 were performed using the Stratagene Mx3005 real-time PCR machine (FIG. 19). The thermal profile was based on the dissociation curve analysis software parameters: heat at 70° C. for 30 sec, cool to 40° C. hold for 30 second, and then slowly increase the temperature to 94° C., the fluorescence emission data is continually collected during the rising temperatures. The first negative derivative of the emission reading with respect to temperature is plotted against temperature to form curves, and each peak of the curve corresponds to the actual $T_m$ of the probe.

Singleplex, doubleplex and triplex amplifications were performed using the same reaction master mix, but in the presence of one target, or two targets or all three targets.

A master reaction mixture was made containing 0.1 µM of first oligonucleotides of each of the three probes, 0.4 µM of second oligonucleotides of each of the three probes, 0.2 µM of primers (not the first oligonucleotide of probe) of each target, and standard PCR ingredients (NEB). Amplification reactions were performed in Stratagene Mx3005 real-time PCR system with the following cycling conditions:

1. Amplification: 40 cycles of 94° C. 15 s; 63° C. 20 s; 50° C. 20 s; 55° C. 20 s 63° C. 20 s; 68° C. 20 s; 72° C. 20 s; fluorescence measurements were recorded during the read steps 50° C., 55° C., 63° C., 68° C., and 72° C.
3. Post-amplification melting profile: after last cycle at 72° C. for 20 sec, cool to 40° C. hold for 30 second, and then slowly increase the temperature to 78° C., the fluorescence emission data is continually collected during the rising temperatures.

Eight reactions were set up: reaction (A) contains no template; reaction (B) contains target 2 template; reaction (C) contains target 3 template; reaction (D) contains target 2 and 3; reaction (E) contains target 1; reaction (F) contains targets 1 and 2; reaction (G) contains targets 1 and 3; reaction (H) contains targets 1, 2 and 3. The post-amplification melting profiles for eight reactions are shown in FIG. 19.

Comparison of the post-amplification melting profiles in the presence of targets and without target indicated the following (FIG. 19):
In reaction A the no probe is consumed and the melting profile is the signature of the mixture of all three probes.
In reaction B the probe 2 is consumed.
In reaction C, probe 3 is consumed.
In reaction D, probes 2 and 3 are consumed.
In reaction E, probe 1 consumed.
In reaction F, probes 1 and 2 are consumed.
In reaction G, probes 1 and 3 are consumed.
In reaction D, probes 1, 2 and 3 are consumed.

Cycle by cycle fluorescence emissions FE were obtained at five measuring temperatures: MT 50° C., 55° C., 63° C., 68° C., and 72° C. The Actual Consumed Amount for each probe may be calculated by the formula FEa=(ACA1)*(ds1a)%+ (ACA2)*(ds2a)%+(ACA3)*(ds3a)% . . . +(ACAn)*(dsna)%.

Example 4

Amplification Primers for Target 1 (K10)

```
K10F155
                                      (SEQ ID NO: 5)
CTCTGCTGACTTCAAAACGAGAAGAG;

K10R14
                                      (SEQ ID NO: 21)
CCTGAGGGTTAAATCTTCCCCATTGA
```

Probe for target 1 (referred to as probe1) includes: first oligonucleotide K10R266Famph GTTCAATTGGGTTTCACCGCGCT-TAGTTACA (SEQ ID NO: 7), which 5' end is attached with Fam; 3' end is attached with a phosphate group instead of 3'—OH; and second oligonucleotide K10R266Dab GCGCGGTGAAACCCAATTGAAC (SEQ ID NO: 2), which 3' end is attached with DABCYL.

Amplification primers for target 2 (SV40):

```
dsredendF2
                                      (SEQ ID NO: 8)
GTAAGATCCACCGGATCTAGATAAC;

sv40testR
                                      (SEQ ID NO: 9)
GGGAGGTGTGGGAGGTTTTTTAAAG.
```

Probe for target 2 (referred to as probe 2) includes: first oligonucleotide SV40R1F3FAPh ATCAGCCATACCACATTGTAGAG-GTTTTAC (SEQ ID NO: 10), which 5' end is attached with Fam; 3' end is attached with a phosphate group instead of 3'—OH; and second oligonucleotide SV40R1F3Dab CAAATGTGGTATGGCTGAT (SEQ ID NO: 4), which 3' end is attached with DABCYL.

The first oligonucleotide and the second oligonucleotide were combined at various ratios, typically 1:2-1:4 to form a partially double-stranded linear DNA probe. In the absence of target, the formation of the first and the second oligonucleotide hybrid brings the quencher and the fluorophore into close proximity, efficiently quenching the fluorescent signal. In the presence of the target, the first oligonucleotide preferentially hybridises to the target sequence. As a result, the quencher is separated from the fluorophore resulting in an increase in fluorescence emission.

The first oligonucleotides in probe 1 and 2 are modified to contain blocked 3' end, so that it cannot be extended. However, when the first oligonucleotide binds to the target sequence, it can be degraded by the 5' nuclease activity of a polymerase. The degradation of the first oligonucleotide of the probe (the consumed probes) results in decrease of the number of first oligonucleotide available to bind with the second oligonucleotides of probe, thereby increasing the fluorescence signal when measured at appropriate temperature.

Figure 20:
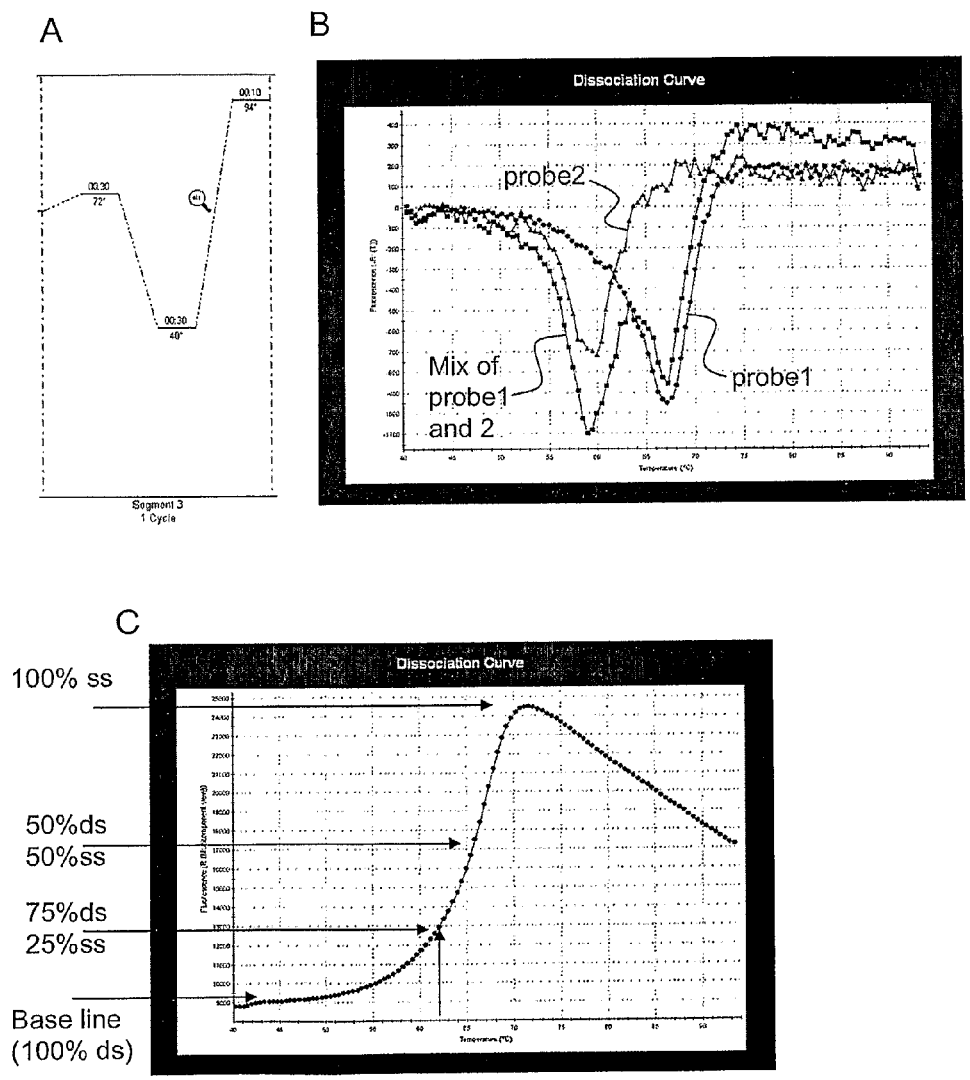
FIG. 20 (A) shows the melting temperature and collection setting up profile. (B) is melting profiles of probe 1, 2 and the mix of probe 1 and 2. (C) is the multicomponent view of the dissociation curve showing how to estimate of the percentage of the double-stranded form of a probe.

Melting profile analysis of probe 1, probe 2, and mixed probe 1 and 2 was performed using the Stratagene Mx3005 real-time PCR machine (FIG. 20). The thermal profile was based on the dissociation curve analysis software parameters (FIG. 20A): heat at 72° C. for 30 sec, cool to 40° C. hold for 30 second, and then slowly increase the temperature to 94° C., the fluorescence emission data is continually collected during the rising temperatures. The first negative derivative of the emission reading with respect to temperature is plotted against temperature to form curves, and each peak of the curve corresponds to the actual $T_m$ of the probe. The probe 1 has a peak at 67° C. as Tm; the probe 2 has a peak at 59° C. as Tm (FIG. 20B).

The percentages of double stranded form and single stranded form of each probe were estimated in the following table. The actual calculation can also be done by computer software.

|  | probe 1 | | probe 2 | |
| --- | --- | --- | --- | --- |
|  | ds % | ss % | ds % | ss % |
| 71° C. | 30 | 70 | 0 | 100 |
| 69° C. | 40 | 60 | 0 | 100 |
| 67° C. | 50 | 50 | 1 | 99 |
| 65° C. | 65 | 35 | 3 | 97 |
| 62° C. | 75 | 25 | 5 | 95 |
| 61° C. | 85 | 15 | 25 | 75 |
| 59° C. | 95 | 5 | 50 | 50 |
| 57° C. | 97 | 3 | 65 | 35 |
| 55° C. | 98 | 2 | 75 | 25 |
| 54° C. | 100 | 0 | 85 | 15 |
| 52° C. | 100 | 0 | 100 | 0 |

The estimation (calculation) can be done based on the multi-component view of the dissociation curve (the Fluorescence R versus temperature, FIG. 20C). The base line was assumed as 100% double-stranded, which has a R as 9000. The R at a temperature (100% single-stranded) is 24500. At temperature 62° C., the R is 13000. The difference of the fluorescence values between 62° C. and base line dR=13000−9000=4000. The percentage of double-stranded probe at 62° C. is estimated as 4000/(24500−9000) which is 25.8%.

Multiplex Real-Time PCR and Standard Curve Analysis

Primer-probe master mix was set up as follows: the primers and probes were mixed to a final concentration 0.4 µM of probes and 0.6 µM of primers, which creates a 2× primer-probe master mix.

The reaction mix was created by combining equal amount of 2×primer-probe master mix and 2×TaqMan® Gene Expression Master Mix (Applied Biosystem, cat. No 4369514).

Template DNAs containing target 1, target 2, and mixed target 1 and 2 were serially diluted as follows: 1, 0.1, 0.01, 0.001, 0.0001, 0.00001, 0.000001.

The singleplex PCRs were performed using DNA sample containing target 1 (k10) or target 2 (SV40). Doubleplex PCR was performed using DNA sample containing mixture of target 1 (k10) and target 2 (SV40).

The thermal profile was: 95° C. for 8 min 30 sec; 40 cycles of 94° C. 10 s; 66° C. 20 s; 63° C. 20 sec; 54° C. 30 s; 52° C. 20 s; 61° C. 20 s; 62° C. 20 s; 68° C. 20 s; fluorescence measurements were recoded during the read steps 66° C., 63° C., 54° C.; 52° C.; 61° C.; 62° C.; 68° C.

Fluorescence emission (dR) at 62° C. was chosen as FE1; Fluorescence emission (dR) at 52° C. was chosen as FE2. Based on the table above and the formula for calculation of Actual Consumed Amount (ACA) in the description and claims, we had followings:

$$\text{At } 62° \text{ C., } FE1=0.75*(ACA1)+0.05*ACA2 \quad (1)$$

$$\text{At } 52° \text{ C., } FE2=100\%*ACA1+100\%*ACA2 \quad (2)$$

According to (1) and (2), $$ACA1=(FE1-0.05*FE2)/0.7$$

$$ACA2=(0.75*FE2-FE1)/0.7$$

For the doubleplex reaction where both targets are present, The FE1 and FE2 were obtained as follows:

| | FE1: | | | | | | |
| --- | --- | --- | --- | --- | --- | --- | --- |
| DNA Cycles | 1 Fluorescence (dR) | 0.1 Fluorescence (dR) | 0.01 Fluorescence (dR) | 0.001 Fluorescence (dR) | 0.0001 Fluorescence (dR) | 0.00001 Fluorescence (dR) | 0.000001 Fluorescence (dR) |
| 1 | 221.8519 | 592.1771 | 466.8143 | 570.415 | 633.3002 | 1036.42 | 421.2163 |
| 2 | 78.16296 | 358.3926 | 225.5527 | 329.063 | 377.0944 | 719.6661 | 242.6808 |
| 3 | −92.1926 | 86.34888 | 14.51325 | 45.78511 | 74.59224 | 416.5415 | −6.11397 |
| 4 | −50.1037 | −12.7813 | 41.21457 | −10.1348 | −30.6753 | 276.2934 | −85.6618 |
| 5 | 64.13333 | 14.05972 | −1.8372 | −40.602 | 15.13533 | 123.0042 | −63.1274 |
| 6 | 201.4198 | 10.22446 | −41.4733 | −53.2517 | 82.6387 | 36.36786 | 44.4345 |
| 7 | 377.3893 | −11.5029 | −35.6376 | −28.9621 | −14.2937 | −1.71745 | 48.67219 |
| 8 | 603.2532 | −2.52759 | −35.6445 | 72.64048 | −95.038 | −19.6191 | 10.80182 |
| 9 | 937.7486 | 37.68192 | 4.40094 | 56.68076 | −41.7196 | −22.7929 | 55.5621 |
| 10 | 1438.121 | 267.6362 | 54.46389 | −16.4664 | −0.047 | 5.60935 | 69.53259 |
| 11 | 1912.119 | 515.172 | 80.866 | −8.3427 | 25.41037 | −23.7965 | 73.90648 |
| 12 | 2478.326 | 746.9017 | 174.0478 | −19.1287 | −25.8707 | −48.8049 | 9.74818 |
| 13 | 3092.269 | 1166.696 | 420.1562 | 1.78202 | −86.7312 | 9.31902 | −13.5875 |
| 14 | 3609.791 | 1705.178 | 759.2402 | 28.25835 | −59.7849 | 10.1538 | −2.64903 |
| 15 | 4192.506 | 2276.224 | 1071.983 | 81.25654 | 5.76368 | 57.22552 | −0.2858 |
| 16 | 4766.951 | 2836.79 | 1433.611 | 167.0954 | 87.84637 | 69.04288 | −7.78099 |
| 17 | 5317.307 | 3430.196 | 1859.535 | 343.2144 | 62.77375 | −24.8912 | −85.5623 |
| 18 | 5864.633 | 4030.883 | 2451.891 | 642.0935 | 29.9827 | −35.4091 | −71.1057 |
| 19 | 6371.949 | 4558.996 | 3146.391 | 1035.559 | 102.6188 | 4.87837 | −54.5698 |
| 20 | 6808.262 | 5074.252 | 3798.272 | 1409.887 | 256.3974 | −15.5657 | −64.6741 |
| 21 | 7188.24 | 5633.888 | 4425.947 | 1861.169 | 432.2234 | −59.9202 | 16.67492 |
| 22 | 7615.441 | 6064.984 | 5029.553 | 2489.103 | 739.0652 | 28.08837 | 39.50831 |
| 23 | 8014.048 | 6434.568 | 5640.136 | 3107.587 | 1285.579 | 186.218 | 25.16984 |
| 24 | 8365.791 | 6845.646 | 6207.045 | 3699.587 | 1822.317 | 301.388 | 61.10741 |
| 25 | 8736.58 | 7257.224 | 6784.729 | 4176.094 | 2328.129 | 483.2382 | 96.137 |
| 26 | 9026.05 | 7652.967 | 7387.671 | 4613.769 | 2908.966 | 836.6483 | 145.8639 |
| 27 | 9241.081 | 7934.433 | 7890.366 | 5104.5 | 3553.812 | 1367.912 | 282.49 |
| 28 | 9454.632 | 8185.806 | 8268.313 | 5596.249 | 4202.327 | 1961.793 | 465.7491 |
| 29 | 9667.69 | 8492.481 | 8646.676 | 6044.339 | 4731.732 | 2518.214 | 688.2191 |
| 30 | 9851.583 | 8824.257 | 8953.845 | 6525.541 | 5146.767 | 3114.147 | 997.4262 |

-continued

| FE1: | | | | | | | |
|---|---|---|---|---|---|---|---|
| DNA Cycles | 1 Fluorescence (dR) | 0.1 Fluorescence (dR) | 0.01 Fluorescence (dR) | 0.001 Fluorescence (dR) | 0.0001 Fluorescence (dR) | 0.00001 Fluorescence (dR) | 0.000001 Fluorescence (dR) |
| 31 | 10081.42 | 9017.401 | 9232.615 | 6913.781 | 5628.011 | 3785.585 | 1400.212 |
| 32 | 10292.91 | 9159.333 | 9552.92 | 7172.034 | 6098.659 | 4475.191 | 1954.525 |
| 33 | 10403.28 | 9320.528 | 9898.736 | 7505.291 | 6576.109 | 5118.187 | 2599.346 |
| 34 | 10514.61 | 9401.811 | 10201.06 | 7778.55 | 7015.158 | 5748.646 | 3245.67 |
| 35 | 10611.93 | 9523.123 | 10353.21 | 7965.142 | 7308.741 | 6347.592 | 3873.495 |
| 36 | 10640.24 | 9682.444 | 10468.31 | 8154.512 | 7596.835 | 6862.701 | 4481.487 |
| 37 | 10704.55 | 9664.769 | 10654.39 | 8367.142 | 7799.1 | 7291.197 | 5006.868 |
| 38 | 10781.86 | 9608.762 | 10868.13 | 8504.858 | 7997.755 | 7619.823 | 5543.046 |
| 39 | 10833.84 | 9651.977 | 10982.09 | 8637.936 | 8213.206 | 7987.825 | 6035.822 |
| 40 | 10911.49 | 9675.693 | 11063.72 | 8819.347 | 8397.157 | 8380.493 | 6459.098 |

| FE2: | | | | | | | |
|---|---|---|---|---|---|---|---|
| DNA Cycles | 1 Fluorescence (dR) | 0.1 Fluorescence (dR) | 0.01 Fluorescence (dR) | 0.001 Fluorescence (dR) | 0.0001 Fluorescence (dR) | 0.00001 Fluorescence (dR) | 0.000001 Fluorescence (dR) |
| 1 | 251.4671 | 205.968 | 310.1105 | 43.54564 | 382.2339 | 312.4356 | 256.8311 |
| 2 | 55.8251 | 87.68861 | 218.6788 | 27.16047 | 275.7769 | 193.1356 | 172.3411 |
| 3 | −49.5206 | −4.1834 | 109.6545 | 25.47901 | 225.5422 | 99.35408 | 102.8511 |
| 4 | −68.4342 | −5.91962 | 23.09933 | −18.3012 | 166.0481 | 38.41212 | 46.69446 |
| 5 | 62.12963 | 24.38944 | −16.2994 | −56.781 | 108.1344 | 46.41665 | 10.31559 |
| 6 | 415.1859 | −14.2864 | −25.6461 | −9.82739 | 101.7474 | 35.07002 | 22.19599 |
| 7 | 903.4063 | 3.04275 | 6.69132 | 35.93742 | 40.86928 | −2.06033 | 18.49614 |
| 8 | 1567.348 | 170.0403 | 13.25673 | 20.63928 | −8.83917 | 6.54807 | −22.3971 |
| 9 | 2529.197 | 501.5939 | −1.10185 | −22.6798 | 7.50892 | −11.5973 | −44.0215 |
| 10 | 3752.015 | 982.6662 | 29.5649 | −23.006 | −13.4575 | −55.6605 | 15.77702 |
| 11 | 5171.823 | 1695.911 | 138.5734 | −8.00106 | −23.5287 | −74.0298 | 26.04988 |
| 12 | 6558.96 | 2707.548 | 399.3626 | −8.88584 | −13.6349 | −86.1676 | −25.1858 |
| 13 | 7836.874 | 3920.648 | 860.0785 | 38.26616 | −16.4193 | −67.5617 | −18.591 |
| 14 | 9129.714 | 5321.902 | 1511.437 | 144.7638 | −20.7633 | −61.3746 | −20.3861 |
| 15 | 10335.2 | 6915.875 | 2471.009 | 310.3765 | −5.96032 | −51.9937 | −13.3111 |
| 16 | 11419.56 | 8566.42 | 3724.986 | 633.3611 | 54.22491 | −27.5482 | −0.61273 |
| 17 | 12463.55 | 10027.49 | 5220.098 | 1150.136 | 114.5376 | −31.0812 | −9.03993 |
| 18 | 13343.41 | 11328.73 | 6908.922 | 1950.175 | 243.226 | −26.9403 | −27.509 |
| 19 | 14056.57 | 12656.7 | 8570.649 | 3099.635 | 520.0398 | 20.75852 | −12.992 |
| 20 | 14700.82 | 13829.58 | 10210.68 | 4441.901 | 985.5619 | 84.30999 | −1.81296 |
| 21 | 15160.44 | 14812.09 | 11791.47 | 5899.104 | 1636.987 | 165.1457 | −30.7466 |
| 22 | 15500.18 | 15700.82 | 13229.19 | 7446.952 | 2533.379 | 292.7428 | −35.3845 |
| 23 | 15882.3 | 16474.95 | 14480.55 | 8935.681 | 3752.761 | 531.2603 | 4.74292 |
| 24 | 16224.54 | 17109.88 | 15546.79 | 10263.7 | 5190.473 | 992.7513 | 27.12541 |
| 25 | 16511.15 | 17676.08 | 16537.66 | 11545.83 | 6745.627 | 1711.567 | 90.59292 |
| 26 | 16779.23 | 18230.03 | 17359.4 | 12765.31 | 8268.93 | 2691.491 | 222.7554 |
| 27 | 16974.12 | 18690.57 | 18075.1 | 13756.26 | 9666.282 | 4042.45 | 514.8163 |
| 28 | 16980.95 | 19057.31 | 18772.45 | 14598.35 | 11033.65 | 5713.422 | 1022.177 |
| 29 | 17028.43 | 19398.44 | 19303.02 | 15325.5 | 12286.02 | 7498.065 | 1731.637 |
| 30 | 17115.79 | 19590.37 | 19730.33 | 15961.32 | 13248.73 | 9328.264 | 2795.13 |
| 31 | 17137.45 | 19764.9 | 20228.55 | 16577.71 | 14156.22 | 11036.98 | 4243.635 |
| 32 | 17161.87 | 20071.3 | 20558.75 | 17061.62 | 15000.3 | 12520.54 | 5867.809 |
| 33 | 17179.21 | 20321.65 | 20749.6 | 17509.04 | 15713.24 | 13969.38 | 7541.208 |
| 34 | 17161.53 | 20504.66 | 21095.34 | 18035.63 | 16353.48 | 15241.98 | 9240.014 |
| 35 | 17091.17 | 20524.22 | 21345.03 | 18399.94 | 16909.47 | 16322.83 | 10855.29 |
| 36 | 17034.91 | 20487.29 | 21421.39 | 18585.82 | 17293.39 | 17336.1 | 12288.72 |
| 37 | 16877.36 | 20519.2 | 21450.29 | 18810.89 | 17550.28 | 18050.5 | 13425.21 |
| 38 | 16677.05 | 20515.39 | 21532.38 | 19083.03 | 17903.49 | 18608.29 | 14431.37 |
| 39 | 16547.15 | 20532.68 | 21645.86 | 19238.86 | 18119.48 | 19175.54 | 15425.44 |
| 40 | 16436.08 | 20571.96 | 21712.84 | 19343.85 | 18238.97 | 19721.29 | 16388.67 |

The calculated ACAs for the target 1 are listed in the following table:

| | ACA1 = (FE1 − 0.05 * FE2)/0.7 | | | | | | |
|---|---|---|---|---|---|---|---|
| DNA Cycles | 1 Fluorescence (dR) | 0.1 Fluorescence (dR) | 0.01 Fluorescence (dR) | 0.001 Fluorescence (dR) | 0.0001 Fluorescence (dR) | 0.00001 Fluorescence (dR) | 0.000001 Fluorescence (dR) |
| 1 | 298.9693 | 831.2553 | 644.7269 | 811.7682 | 877.4121 | 1458.284 | 583.3925 |
| 2 | 107.6739 | 505.726 | 306.5982 | 468.15 | 519.0079 | 1014.299 | 334.3768 |
| 3 | −128.167 | 123.6544 | 12.90075 | 63.58737 | 90.45019 | 587.9625 | −16.0808 |
| 4 | −66.6886 | −17.8362 | 57.22801 | −13.171 | −55.6825 | 391.9611 | −125.709 |
| 5 | 87.18121 | 18.34321 | −1.46033 | −53.9471 | 13.89802 | 172.4047 | −90.9188 |
| 6 | 258.0864 | 15.62683 | −57.4158 | −75.3718 | 110.7876 | 49.44908 | 61.89243 |
| 7 | 474.5986 | −16.65 | −51.3888 | −43.9414 | −23.3388 | −2.30633 | 68.21055 |
| 8 | 749.8369 | −15.7566 | −51.8677 | 102.2979 | −135.137 | −28.495 | 17.03097 |
| 9 | 1158.984 | 18.00318 | 6.365761 | 82.5925 | −60.1358 | −31.7328 | 82.51882 |
| 10 | 1786.458 | 312.1469 | 75.69378 | −21.8801 | 0.894105 | 11.98911 | 98.20534 |
| 11 | 2362.183 | 614.8234 | 105.6248 | −11.3466 | 37.98115 | −28.7071 | 103.72 |
| 12 | 3071.969 | 873.6061 | 220.1138 | −26.692 | −35.9842 | −63.5665 | 15.72496 |
| 13 | 3857.751 | 1386.662 | 538.789 | −0.18755 | −122.729 | 18.13872 | −18.0828 |
| 14 | 4504.722 | 2055.833 | 976.669 | 30.0288 | −83.9239 | 18.88933 | −2.32818 |
| 15 | 5251.066 | 2757.757 | 1354.903 | 93.91102 | 8.659566 | 85.46458 | 0.542506 |
| 16 | 5994.248 | 3440.67 | 1781.946 | 193.4676 | 121.6216 | 100.6004 | −11.0719 |
| 17 | 6705.9 | 4184.031 | 2283.615 | 408.1537 | 81.49553 | −33.3388 | −121.586 |
| 18 | 7424.947 | 4949.209 | 3009.207 | 777.9782 | 25.45914 | −48.6602 | −99.6146 |
| 19 | 8098.744 | 5608.801 | 3882.655 | 1257.968 | 109.4526 | 5.486349 | −77.0288 |
| 20 | 8676.03 | 6261.104 | 4696.768 | 1696.846 | 295.8847 | −28.2588 | −92.262 |
| 21 | 9186.026 | 6990.405 | 5480.533 | 2237.449 | 500.5343 | −97.3964 | 26.0175 |
| 22 | 9772.045 | 7542.776 | 6240.133 | 3023.936 | 874.8518 | 19.21605 | 58.96791 |
| 23 | 10314.19 | 8015.457 | 7023.012 | 3801.147 | 1568.487 | 228.0786 | 35.61813 |
| 24 | 10792.23 | 8557.361 | 7756.722 | 4552.003 | 2232.562 | 359.6435 | 85.35877 |
| 25 | 11301.46 | 9104.886 | 8511.208 | 5141.146 | 2844.068 | 568.0855 | 130.8676 |
| 26 | 11695.84 | 9630.665 | 9313.859 | 5679.29 | 3565.028 | 1002.963 | 192.4659 |
| 27 | 11989.11 | 9999.863 | 9980.874 | 6309.553 | 4386.426 | 1665.413 | 366.7845 |
| 28 | 12293.69 | 10332.77 | 10470.99 | 6951.903 | 5215.206 | 2394.46 | 592.3432 |
| 29 | 12594.67 | 10746.51 | 10973.61 | 7540.091 | 5882.044 | 3061.872 | 859.4819 |
| 30 | 12851.13 | 11206.77 | 11381.9 | 8182.107 | 6406.186 | 3782.477 | 1225.242 |
| 31 | 13177.93 | 11470.22 | 11744.55 | 8692.708 | 7028.858 | 4619.623 | 1697.187 |
| 32 | 13478.31 | 11651.1 | 12178.55 | 9027.076 | 7640.921 | 5498.806 | 2373.049 |
| 33 | 13634.74 | 11863.49 | 12658.94 | 9471.199 | 8272.066 | 6313.883 | 3174.694 |
| 34 | 13795.05 | 11966.54 | 13066.13 | 9823.955 | 8853.549 | 7123.638 | 3976.671 |
| 35 | 13939.1 | 12138.45 | 13265.66 | 10064.49 | 9233.239 | 7902.072 | 4758.187 |
| 36 | 13983.56 | 12368.69 | 13424.63 | 10321.74 | 9617.38 | 8565.566 | 5524.359 |
| 37 | 14086.69 | 12341.16 | 13688.39 | 10609.42 | 9887.98 | 9126.674 | 6193.726 |
| 38 | 14211.44 | 12261.42 | 13987.88 | 10786.72 | 10146.65 | 9556.297 | 6887.825 |
| 39 | 14294.98 | 12321.92 | 14142.57 | 10965.7 | 10438.9 | 10041.5 | 7520.786 |
| 40 | 14413.83 | 12352.99 | 14254.4 | 11217.36 | 10693.16 | 10563.47 | 8056.664 |

Figure 21:
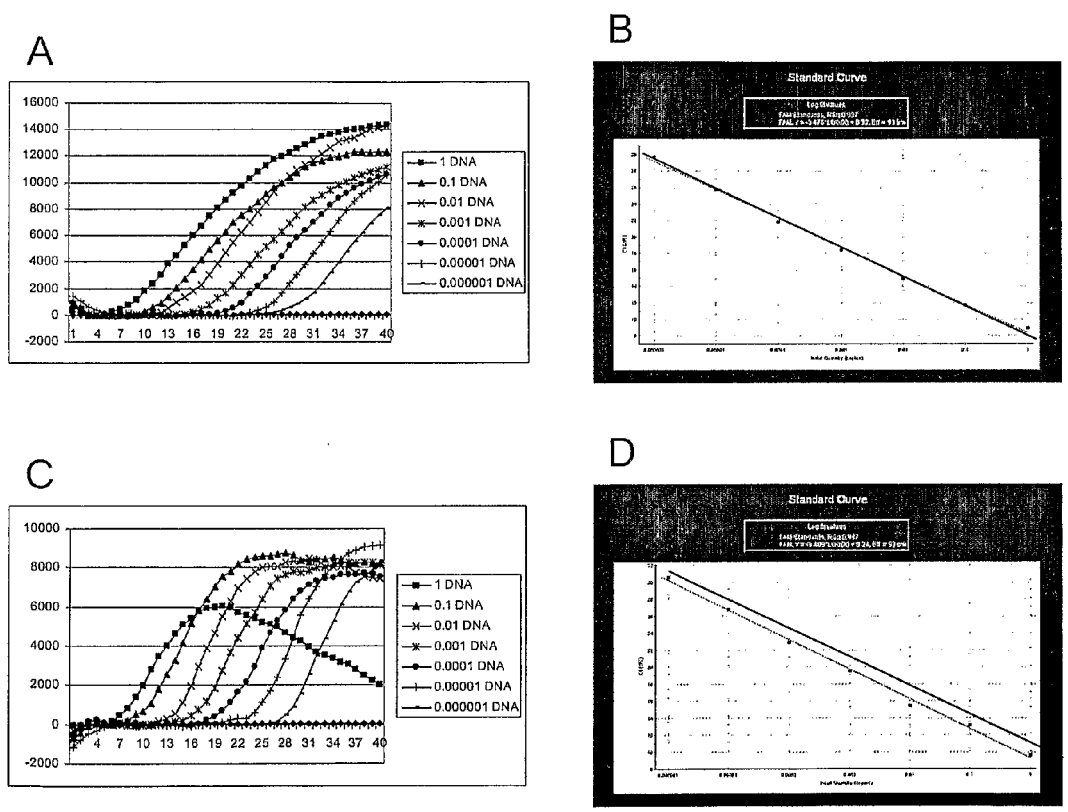
FIG. 21 is the graphic presentations of the amplification plots for Actual Consumed amount and standard curves (Example 4).
Figure 21:
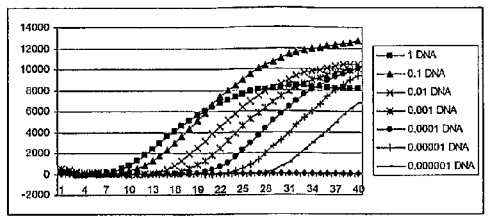
Figure 21:
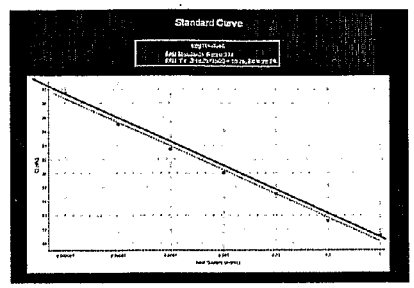
Figure 21:
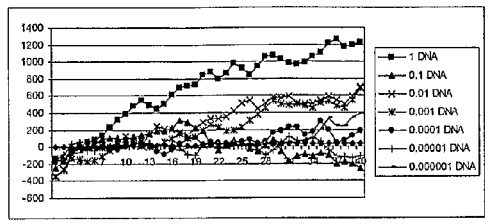
Figure 21:
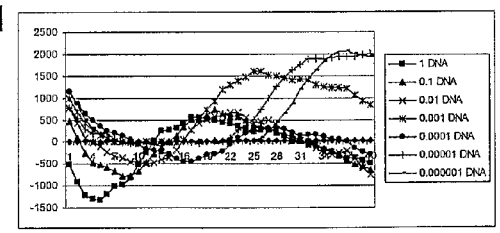
Figure 21:
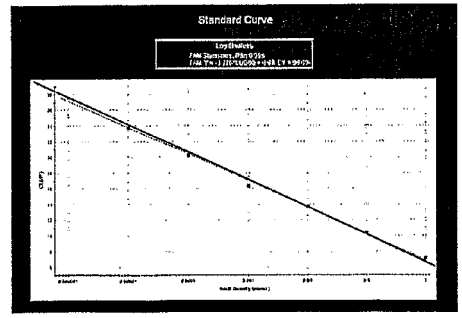

The graphic presentation of the amplification plots for ACA1 is shown in FIG. 21A. The standard curve is shown in FIG. 21B.

The calculated ACAs for the target 2 are listed in the following table:

| | ACA2 = (0.75 * FE2 − FE1)/0.7 | | | | | | |
|---|---|---|---|---|---|---|---|
| DNA Cycles | 1 Fluorescence (dR) | 0.1 Fluorescence (dR) | 0.01 Fluorescence (dR) | 0.001 Fluorescence (dR) | 0.0001 Fluorescence (dR) | 0.00001 Fluorescence (dR) | 0.000001 Fluorescence (dR) |
| 1 | −47.5022 | −625.287 | −334.616 | −768.223 | −495.178 | −1145.85 | −326.561 |
| 2 | −51.8488 | −418.037 | −87.9194 | −440.99 | −243.231 | −821.163 | −162.036 |
| 3 | 78.64594 | −127.838 | 96.75373 | −38.1084 | 135.092 | −488.608 | 118.9319 |
| 4 | −1.7456 | 11.91655 | −34.1287 | −5.13019 | 221.7306 | −353.549 | 172.4038 |
| 5 | −25.0516 | 6.046229 | −14.8391 | −2.83399 | 94.23638 | −125.988 | 101.2344 |
| 6 | 157.0995 | −29.9133 | 31.76967 | 65.54444 | −9.04024 | −14.3791 | −39.6964 |
| 7 | 428.8077 | 19.69278 | 58.0801 | 79.87884 | 64.20807 | 0.246004 | −49.7144 |
| 8 | 817.5112 | 185.7968 | 65.12441 | −81.6586 | 126.298 | 35.04308 | −39.4281 |
| 9 | 1370.213 | 483.5907 | −7.46761 | −105.272 | 67.64471 | 20.13557 | −126.54 |
| 10 | 1965.557 | 670.5193 | −46.1289 | −1.1258 | −14.3516 | −67.6496 | −82.4283 |
| 11 | 2809.639 | 1081.088 | 32.94868 | 3.345579 | −61.5099 | −45.3226 | −77.6701 |
| 12 | 3486.991 | 1833.942 | 179.2487 | 17.8062 | 22.34935 | −22.6011 | −40.9108 |
| 13 | 3979.123 | 2533.985 | 321.2895 | 38.45371 | 106.3096 | −85.7005 | −0.50822 |
| 14 | 4624.992 | 3266.069 | 534.7678 | 114.7349 | 63.16068 | −80.2639 | −18.0579 |
| 15 | 5084.13 | 4158.117 | 1116.106 | 216.4655 | −14.6199 | −137.458 | −13.8536 |

-continued

| | | | ACA2 = (0.75 * FE2 − FE1)/0.7 | | | | |
|---|---|---|---|---|---|---|---|
| DNA Cycles | 1 Fluorescence (dR) | 0.1 Fluorescence (dR) | 0.01 Fluorescence (dR) | 0.001 Fluorescence (dR) | 0.0001 Fluorescence (dR) | 0.00001 Fluorescence (dR) | 0.000001 Fluorescence (dR) |
| 16 | 5425.31 | 5125.75 | 1943.041 | 439.8935 | −67.3967 | −128.149 | 10.4592 |
| 17 | 5757.647 | 5843.458 | 2936.484 | 741.9825 | 33.04203 | 2.257639 | 112.5462 |
| 18 | 5918.465 | 6379.525 | 3899.715 | 1172.197 | 217.7669 | 21.71986 | 72.10566 |
| 19 | 5957.824 | 7047.902 | 4687.995 | 1841.667 | 410.5871 | 15.27217 | 64.03682 |
| 20 | 6024.792 | 7568.477 | 5513.91 | 2745.055 | 689.6772 | 112.5688 | 90.44904 |
| 21 | 5974.415 | 7821.69 | 6310.941 | 3661.655 | 1136.453 | 262.5421 | −56.7641 |
| 22 | 5728.138 | 8158.044 | 6989.059 | 4423.016 | 1658.528 | 273.5267 | −94.3524 |
| 23 | 5568.108 | 8459.492 | 7457.54 | 5134.535 | 2184.274 | 303.1817 | −30.8752 |
| 24 | 5432.303 | 8552.52 | 7790.069 | 5711.702 | 2957.911 | 633.1078 | −58.2334 |
| 25 | 5209.693 | 8571.193 | 8026.448 | 6404.68 | 3901.559 | 1143.481 | −40.2747 |
| 26 | 5083.386 | 8599.367 | 8045.539 | 7086.024 | 4703.901 | 1688.528 | 30.2895 |
| 27 | 4985.012 | 8690.708 | 8094.225 | 7446.704 | 5279.856 | 2377.037 | 148.0318 |
| 28 | 4687.26 | 8724.533 | 8301.466 | 7646.448 | 5818.443 | 3318.962 | 429.8334 |
| 29 | 4433.763 | 8651.925 | 8329.415 | 7785.405 | 6403.98 | 4436.192 | 872.1549 |
| 30 | 4264.659 | 8383.6 | 8348.434 | 7779.217 | 6842.547 | 5545.787 | 1569.888 |
| 31 | 3959.521 | 8294.68 | 8484.001 | 7885.006 | 7127.362 | 6417.359 | 2546.448 |
| 32 | 3683.561 | 8420.204 | 8380.202 | 8034.549 | 7359.379 | 7021.734 | 3494.76 |
| 33 | 3544.47 | 8458.161 | 8090.662 | 8037.842 | 7441.177 | 7655.495 | 4366.514 |
| 34 | 3366.479 | 8538.121 | 8029.209 | 8211.672 | 7499.927 | 8118.338 | 5263.343 |
| 35 | 3152.068 | 8385.771 | 8079.379 | 8335.443 | 7676.232 | 8420.755 | 6097.102 |
| 36 | 3051.351 | 8118.604 | 7996.758 | 8264.075 | 7676.007 | 8770.53 | 6764.362 |
| 37 | 2790.675 | 8178.046 | 7761.896 | 8201.47 | 7662.296 | 8923.83 | 7231.479 |
| 38 | 2465.607 | 8253.976 | 7544.503 | 8296.31 | 7756.948 | 9051.994 | 7543.548 |
| 39 | 2252.171 | 8210.76 | 7503.288 | 8273.155 | 7680.577 | 9134.043 | 7904.65 |
| 40 | 2022.247 | 8218.972 | 7458.443 | 8126.489 | 7545.813 | 9157.817 | 8332.001 |

The graphic presentation of the amplification plots for ACA2 is shown in FIG. 21C. The standard curve is shown in FIG. 21D.

If only target 1 is present in the reaction, the graphic presentation of the amplification plots for ACA1 is shown in FIG. 21E, the amplification plots for ACA2 is shown in FIG. 21G. The results show that because only target 1 is present in the reaction, the ACA1 reveal the normal amplification curve and normal standard curve (FIG. 21F), whereas the ACA2 reveal the background curve which demonstrates there is no signal for target 2.

If only target 2 is present in the reaction, the graphic presentation of the amplification plots for ACA 1 is shown in FIG. 21H, the amplification plots for ACA2 is shown in FIG. 21I. The results show that because only target 2 is present in the reaction, the ACA2 reveal the normal amplification curve and normal standard curve (FIG. 21J), whereas the ACA1 reveal the background curve which demonstrates there is no signal for target 1.

Example 5

Amplification Primers for Target 1 (K10)

```
K10F155
                              (SEQ ID NO: 5)
CTCTGCTGACTTCAAAACGAGAAGAG;

K10R14
                              (SEQ ID NO: 21)
CCTGAGGGTTAAATCTTCCCCATTGA
```

Probe for target 1 (referred to as probe 1) includes: first oligonucleotide
K10R266Famph GTTCAATTGGGTTTCACCGCGCT-TAGTTACA (SEQ ID NO: 7), which 5' end is attached with Fam; 3' end is attached with a phosphate group instead of 3' —OH; and second oligonucleotide
K10R266Dab GCGCGGTGAAACCCAATTGAAC (SEQ ID NO: 2), which 3' end is attached with DABCYL.

Amplification primers for target 2 (SV40):

```
dsredendF2
                              (SEQ ID NO: 8)
GTAAGATCCACCGGATCTAGATAAC;

sv40testR
                              (SEQ ID NO: 9)
GGGAGGTGTGGGAGGTTTTTTAAAG.
```

Probe for target 2 (referred to as probe 2) includes: first oligonucleotide
SV40R1F3FAPh ATCAGCCATACCACATTTGTAGAG-GTTTTAC (SEQ ID NO: 10), which 5' end is attached with Fam; 3' end is attached with a phosphate group instead of 3' —OH; and second oligonucleotide
SV40R1F3Dab CAAATGTGGTATGGCTGAT (SEQ ID NO: 4), which 3' end is attached with DABCYL.

Amplification primers for target 3 (Jak2):

```
JknewF8
                              (SEQ ID NO: 14)
GTGGAGACGAGAGTAAGTAAAACTACA;

JKnewR8
                              (SEQ ID NO: 15)
CTCCTGTTAAATTATAGTTTACACTGACA;
```

Probe for target 3 (referred to as probe 3) includes: first oligonucleotide
JKR3FamPh AACAGATGCTCTGAGAAAGGCATTAGA (SEQ ID NO: 16), which 5' end is attached with Fam; 3' end is attached with a phosphate group instead of 3' —OH; and second oligonucleotide
JKR3FDabF CTCAGAGCATCTGTT (SEQ ID NO: 12), which 3' end is attached with DABCYL.

Amplification primers for target 4 (Kras):

```
KR12GVF1B
                                         (SEQ ID NO: 17)
GTCACATTTTCATTATTTTTATTATAAGGCCTGC;

KR12GVR12As
                                         (SEQ ID NO: 18)
GATCATATTCGTCCACAAAATGATTC.
```

Probe for target 4 (referred to as probe 4) includes: first oligonucleotide KR12GVFamPh GAATATAAACTTGTGGTAGTTG-GAGCTGT (SEQ ID NO: 19), which 5' end is attached with Fam; 3' end is attached with a phosphate group instead of 3'—OH; and second oligonucleotide KR12GVFamDab CACAAGTTTATATTC (SEQ ID NO: 20), which 3' end is attached with DABCYL.

The first oligonucleotide and the second oligonucleotide were combined at various ratios, typically 1:2-1:4 to form a partially double-stranded linear DNA probe. In the absence of target, the formation of the first and the second oligonucleotide hybrid brings the quencher and the fluorophore into close proximity, efficiently quenching the fluorescent signal. In the presence of the target, the first oligonucleotide preferentially hybridises to the target sequence. As a result, the quencher is separated from the fluorophore resulting in an increase in fluorescence emission.

The first oligonucleotides in all probes are modified to contain blocked 3' end, so that it cannot be extended. However, when the first oligonucleotide binds to the target sequence, it can be degraded by the 5' nuclease activity of a polymerase. The degradation of the first oligonucleotide of the probe (the consumed probes) results in decrease of the number of first oligonucleotide available to bind with the second oligonucleotides of probe, thereby increasing the fluorescence signal when measured at appropriate temperature.

Multiplex Real-Time PCR and Standard Curve Analysis

Primer-probe master mix was set up as follows: the primers and probes were mixed to a final concentration 0.4 μM of probes and 0.6 μM of primers, which creates a 2× primer-probe master mix.

The reaction mix was created by combining equal amount of 2× primer-probe master mix and 2× TaqMan® Gene Expression Master Mix (Applied Biosystem, cat. No 4369514).

The thermal profile was: 95° C. for 8 min 30 sec; 40 cycles of 94° C. 10 s; 66° C. 20 s; 63° C. 20 sec; 54° C. 30 s; 49° C. 20 s; 55° C. 20 s; 61° C. 20 s; 68° C. 20 s; fluorescence measurements were recoded during the read steps 66° C., 63° C., 54° C.; 49° C.; 55° C.; 61° C.; 68° C.

Figure 22:
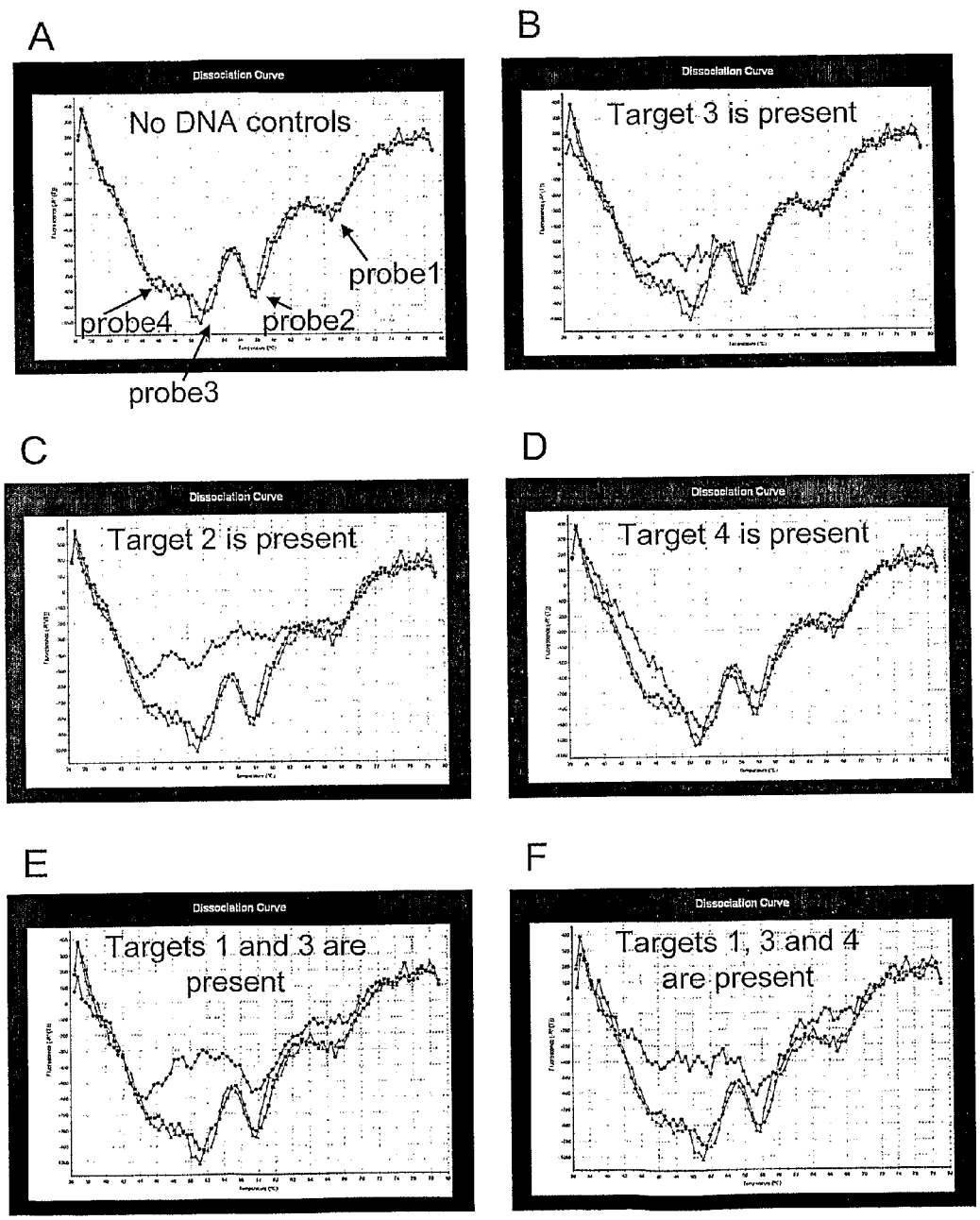
FIG. 22 results of an example of quadruplex amplification. Various combinations of targets present in the reaction were used: reaction (A) contains no template; reaction (B) contains target 3 template; reaction (C) contains target 2 template; reaction (D) contains target 4; reaction (E) contains target 1 and 3; reaction (F) contains targets 1, 3 and 4.

Various combinations of targets present in the reaction were used. FIG. 22 show some of the results: reaction (A) contains no template; reaction (B) contains target 3 template; reaction (C) contains target 2 template; reaction (D) contains target 4; reaction (E) contains target 1 and 3; reaction (F) contains targets 1, 3 and 4.

SEQUENCE LISTING FREE TEXT

SEQ ID NOs: 1, 2, 5, 7 and 21 <223> K10 derived PCR primer
SEQ ID NOs: 3, 4, 6 and 8-10 <223> SV40 derived PCR primer
SEQ ID NOs: 11-16 <223> Jak2 derived PCR primer
SEQ ID NOs: 17-20 <223> Kras derived PCR primer

The invention claimed is:

1. A method for assaying a sample for one or more target nucleic acids, said method comprising:
   (a) contacting a sample comprising one or more target nucleic acids with an amplification reaction mixture comprising:
      (i) one or more pairs of forward/reverse oligonucleotide primers, wherein the primer pairs are capable of amplifying one or more target nucleic acids, if present in the sample,
      (ii) two or more probes, wherein each probe comprises a first oligonucleotide which comprises a first region which is substantially complementary to part of its target nucleic acid and a second region, and at least one second oligonucleotide which comprises a region which is substantially complementary to the second region of the first oligonucleotide, such that the first and second oligonucleotides are capable of forming a double-stranded portion,
      wherein each probe comprises a detectable label or detectable combination of labels which is/are capable of producing a changeable signal which is characteristic of the presence or absence of the double-stranded portion between the first and second oligonucleotides of that probe, and
      wherein at least two of the probes comprise the same detectable label (including different detectable labels with undistinguishable emission spectra) and wherein the melting characteristics of the double-stranded portions between the first and second oligonucleotides of each of such probes are different;

(b) performing an amplification reaction on the sample/reaction mixture under amplification conditions, wherein, when a target nucleic acid is present, the first oligonucleotides of probes which are substantially complementary to part of that target nucleic acid are hybridised with the target nucleic acid, therefore being consumed, wherein the consumed oligonucleotides of probes are no longer able to participate in forming the double stranded portion (the duplex) of the probe; and (c) measuring, at least once, the melting profile of the double-stranded portions between the first and second oligonucleotides of unconsumed probes in the reaction mixture by detecting the signal(s) from the labels in those probes as a function of temperature, wherein the melting profile provides an indication of whether or not at least one target nucleic acid is present in said sample, wherein a first probe of said at least two of the probes has a melting temperature $T_m1$ in terms of its double-stranded portion, wherein a second probe of said at least two of the probes has a melting temperature $T_m2$ in terms of its double-stranded portion, wherein $T_m1 > T_m2$, wherein the same labels are independently attached to the first and second probes, wherein a reduction of any melting peak at $T_m1$ and/or $T_m2$ provides indication of consumption of the first and/or second probe(s).

2. A method according to claim 1, wherein said amplification is PCR, wherein said melting profile GP is measured after completion of reaction/amplification (post-amplification melting profile), and/or is measured during reaction/amplification at each cycle or selected cycles (mid amplification melting profile), and optionally is additionally measured before reaction/amplification takes place (pre-amplification profile), wherein said method additionally comprises step (d):
(i) comparing at least two melting profiles obtained in (c) and/or
(ii) comparing a melting profile obtained in step (c) with a previously-obtained melting profile of the same probes or with a melting profile of the same probes obtained in parallel at the same time in control reactions, or with a theoretical melting profile of the same probes;

wherein a change in the melting profile observed in (i) and/or (ii) provides an indication of whether or not at least one target nucleic acid is present in said sample/reaction mixture.

3. A method according to claim 2, wherein said pre-amplification melting profile is measured in the same reaction vessel before the start of reaction/amplification, or is measured in a separate reaction vessel where no amplification takes place due to that reaction mixture lacking one or more ingredients necessary for the reaction/amplification, wherein in step (d) the post-amplification or mid-amplification melting profile is compared with the pre-amplification melting profile of the duplex of probes to determine whether a particular probe is consumed, this being indicative of the presence of the corresponding target in the sample.

4. A method according to claim 1, wherein said amplification is PCR, wherein at least one detectable label is a fluorescent label, wherein step (b) further comprises the step (b1) obtaining cycle by cycle fluorescence emissions (FE) at various measuring temperatures (MT), wherein said fluorescence emissions (FE) are a baseline corrected fluorescence (dR).

5. A method according to claim 4, wherein said amplification reaction mixture comprises "n" probes ($k_1$-$k_n$) for multiplex detection of "n" nucleic acid targets, wherein each probe in any group of probes having indistinguishable labels has a different melting temperature $T_mk$ in terms of its double stranded portion, wherein $T_mk_1 > T_mk_n$, wherein the percentages of the double-stranded form of each probe at a particular temperature or different temperatures are determined experimentally or are calculated in theory by a computer program, wherein for each probe k a fluorescence emission FEa is obtained at a measuring temperature MT, at which more than 50% of that probe is in double-stranded form, with the exception of probe $k_n$ for which fluorescence emission FE is obtained at a measuring temperature MT at which more than 80% of that probe is in double-stranded form, and wherein optionally a fluorescence emission FE is obtained at a measuring temperature MT, at which no more than 10% of probe $k_1$ is in double-stranded form.

6. A method according to claim 4, wherein the step (b) further comprises the step (b2) determining cycle by cycle the Actual Consumed Amount (ACA) of fluorescence emission for each probe ($k_1$-$k_n$), wherein the Actual Consumed Amount of fluorescence emission of k is depicted as ACAk, wherein at a particular measuring temperature (MT) k has percentage (dsk)% in ds (double-stranded) form, the fluorescence emission FE at this measuring temperature MT contributed by probe k will be (dsk)%*(ACAk), wherein the calculation of Actual Consumed Amount (ACA) uses the following formula:

at measuring temperature MTa, the total fluorescence emission will be, for i=1 to n, FEa=Σ(ACAk$_i$a)*(dsk$_i$a)%, at measuring temperature MTb, the total fluorescence emission will be, for i=1 to n, FEb=Σ(ACAk$_i$b)*(dsk$_i$b)%, at measuring temperature MTc, the total fluorescence emission will be, for i=1 to n, FEc=Σ(ACAk$_i$c)*(dsk$_i$c)%, and so on, wherein the ACA for each probe can be calculated from the above formulas, wherein "*" denotes "multiply by", "Σ" is the standard mathematical symbol for summation, and "n" is the number of probes, wherein n≥2.

7. A method according to claim 6, wherein the Actual Consumed Amount of fluorescence emission of each probe is obtained through a computer program which performs the calculation at each measuring temperature at each cycle.

8. A method according to claim 1, wherein said amplification is an isothermal amplification or a thermal cycling amplification reaction comprising two or more denaturing, annealing, and primer extension steps.

9. A method according to claim 1, wherein said consumption of probes is achieved through hybridisation of the first oligonucleotide of the probe to the target sequence, which is followed by the incorporation of the first oligonucleotide of the probe into the amplified product, wherein when the first oligonucleotide of the probe can be incorporated into the amplified product, the first oligonucleotide is an extendable primer.

10. A method according to claim 1, wherein said consumption of probes is achieved through hybridisation of the first oligonucleotide of the probe to the target sequence, which is followed by degradation of the first and/or second oligonucleotide of the probe, wherein when the first oligonucleotide of the probe is degraded during the reaction, the reaction mixture comprises double-strand dependent nuclease activity.

11. A method according to claim 1, wherein the probe comprises a first label and a second label, wherein the first label is a fluorophore and the second label is a quencher, or vice versa.

12. A method according to claim 11, wherein the first label is attached to the first oligonucleotide and the second label is attached to the second oligonucleotide such that said first label and second label are in close proximity when the probe's internal duplex is formed.

13. A method according to claim 11, wherein labels are on one oligonucleotide of the probe, either the first oligonucleotide or the second oligonucleotide.

14. A method according to claim 13, wherein the first oligonucleotide of the probe does not comprises a label and wherein the probe comprises two second oligonucleotides which are capable of hybridising adjacently or substantially adjacently to different parts of the second region of the first oligonucleotide, wherein one of the second oligonucleotides is attached with a first label, and the other second oligonucleotide is attached with a second label, such that when the two second oligonucleotides are hybridised to the first oligonucleotide, the two labels are brought into close proximity and one label affects the signal from the other.

15. A method according to claim 11, wherein the first and second oligonucleotides of a probe are joined by a linker moiety which comprises nucleotides or a non-nucleotide chemical linker, allowing the first oligonucleotide and second oligonucleotide to form a stem-loop structure, wherein the first and second oligonucleotides are labelled with a first and second label, respectively, such that, when the probe forms an internal stem-loop structure, the labels are brought into close proximity and one label affects the signal from the other.

16. A method according to claim 1, wherein the first oligonucleotide does not comprise a label and the second oligonucleotide comprises at least one label wherein, when the second oligonucleotide hybridises to the first oligonucleotide to form the doublestranded portion of the probe, the label is capable of changing the signal emission relative to the emission of the single-stranded form of the second oligonucleotide.

17. A method according to claim 1, wherein said first region of said first oligonucleotide is substantially overlapping with the second region of said first oligonucleotide or the second region is embedded in the first region, wherein the $T_m$ of the duplex of said first oligonucleotide hybridised with the target sequence is higher than the $T_m$ of the duplex of said first oligonucleotide hybridised with the second oligonucleotide such that if a target is present, the first oligonucleotide forms stronger hybrids with the target and consequently melts at a higher temperature than the first/second oligonucleotide duplex.

18. A method according to claim 1, wherein said first oligonucleotide is blocked at the 3' end, and wherein said second oligonucleotide is blocked at the 3' end.

19. A computer software product comprising a tangible, non-transitory storage medium which when run on suitable data processing means, performs the calculation of Actual Consumed Amount (ACA) as recited in claim 6.

20. A computer system comprising a computer memory having a computer software program of claim 19 stored therein.

21. A method for monitoring a PCR amplification of at least two nucleic acid targets, said method comprising:
(a) contacting a sample comprising two or more target nucleic acids with an amplification reaction mixture comprising:
    (i) one or more pairs of forward/reverse oligonucleotide primers, wherein the primer pairs are capable of amplifying one or more target nucleic acids, if present in the sample,
    (ii) two or more probes, wherein each probe comprises a first oligonucleotide which comprises a first region which is substantially complementary to part of one target nucleic acid and a second region, and at least one second oligonucleotide which comprises a region which is substantially complementary to a second region of the first oligonucleotide, such that the first and second oligonucleotides are capable of forming a double-stranded portion,
    wherein each probe comprises a fluorescent label or fluorescent label/quencher pair which is capable of producing a changeable signal which is characteristic of the presence or absence of a double-stranded portion between the first and second oligonucleotides of that probe, and wherein at least two of the probes comprise the same detectable label or different detectable labels with undistinguishable emissions spectra and wherein the melting characteristics of the double-stranded portions between the first and second oligonucleotides of each of such probes are different;
(b) performing an amplification reaction which comprises thermal cycling of the sample/amplification reaction mixture wherein, when a target nucleic acid is present, the first oligonucleotides of probes which are substantially complementary to part of that target nucleic acid are consumed during the amplification reaction; and wherein the step (b) further comprises the step (b1) obtaining cycle by cycle fluorescence emissions (FE) at various measuring temperatures (MT), wherein said fluorescence emissions (FE) are baseline corrected fluorescence (dR),
    wherein said amplification reaction mixture comprises "n" probes ($k_1$-$k_n$) for multiplex detection of "n" nucleic acid targets, wherein each probe in any group of probes having indistinguishable labels has a different melting temperature $T_m k$ for its double-stranded portion, wherein $T_m k_1 > T_m k_n$,
    wherein the percentages of the double-stranded form of each probe at a particular temperature or different temperatures are determined experimentally or are calculated in theory by a computer program,
    wherein for each probe k a fluorescence emission FE is obtained at a measuring temperature MT, at which more than 50% of that probe is in double-stranded form, with the exception of probe $k_n$ for which fluorescence emission FE is obtained at a measuring temperature MT, at which more than 80% of that probe is in double-stranded form, and wherein optionally a fluorescence emission FE is obtained at a measuring temperature MT at which no more than 10% of probe $k_1$ is in double-stranded form,
    wherein the step (b) further comprises the step (b2) determining cycle by cycle the Actual Consumed Amount of fluorescence emission for each probe ($k_1$-$k_n$), wherein the Actual Consumed Amount of fluorescence emission of k is depicted as ACAk, wherein at a particular measuring temperature (MT) k has percentage (dsk)% in ds (double-stranded) form, the fluorescence emission FE at this measuring temperature MT contributed by k will be (dsk)%*(ACAk),
wherein the calculation of Actual Consumed Amount (ACA) uses the following formula:

at measuring temperature MTa, the total fluorescence emission will be, for i=1 to n, $FEa=\Sigma(ACAk_ia)*(dsk_ia)\%$, at measuring temperature MTb, the total fluorescence emission will be, for i=1 to n, $FEb=\Sigma(ACAk_ib)*(dsk_ib)\%$, at measuring temperature MTc, the total fluorescence emission will be, for i=1 to n, $FEc=\Sigma(ACAk_ic)*(dsk_ic)\%$, and so on, wherein the individual ACA can be calculated from the above formulas, wherein "*" denotes "multiply by", "$\Sigma$" is the standard mathematical symbol for summation, and "n" is the number of probes, wherein $n\geq 2$, wherein the Actual Consumed Amount of fluorescence emission of each probe is obtained through a computer program which performs the calculation at each measuring temperature at each cycle.

* * * * *